(12) United States Patent
Furukawa et al.

(10) Patent No.: US 8,268,755 B2
(45) Date of Patent: Sep. 18, 2012

(54) OXIME ETHER DERIVATIVE AND FUNGICIDE FOR AGRICULTURAL AND HORTICULTURAL USE

(75) Inventors: Hironori Furukawa, Minamiashigara (JP); Raito Kuwahara, Naka-gun (JP); Hiroyasu Hosokawa, Fujieda (JP); Kazuya Shimizu, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 358 days.

(21) Appl. No.: 12/746,892

(22) PCT Filed: Dec. 11, 2008

(86) PCT No.: PCT/JP2008/003717
§ 371 (c)(1),
(2), (4) Date: Jun. 8, 2010

(87) PCT Pub. No.: WO2009/075112
PCT Pub. Date: Jun. 18, 2009

(65) Prior Publication Data
US 2010/0273836 A1    Oct. 28, 2010

(30) Foreign Application Priority Data
Dec. 11, 2007   (JP) .................................. 2007-319111

(51) Int. Cl.
*A01N 35/10*   (2006.01)
*C07C 249/00*   (2006.01)
*C07C 251/00*   (2006.01)
*C07C 291/00*   (2006.01)
*C07C 259/00*   (2006.01)
*C07C 239/00*   (2006.01)

(52) U.S. Cl. .................. 504/344; 564/256; 564/300

(58) Field of Classification Search .................. 504/344; 564/256, 300
See application file for complete search history.

(56) References Cited

U.S. PATENT DOCUMENTS
2008/0153701 A1   6/2008  Gewehr et al.

FOREIGN PATENT DOCUMENTS

| JP | 2003-231672 | | 8/2003 |
| JP | 2003-528866 | | 9/2003 |
| JP | 2004-168683 | | 6/2004 |
| JP | 2004168683 A | * | 6/2004 |
| WO | WO 01/72726 | | 10/2001 |
| WO | WO 2006/069716 | | 7/2006 |
| WO | WO-2010/018676 A1 | | 2/2010 |

OTHER PUBLICATIONS

Japanese Patent Office, International Search Report (translated) mailed Jan. 27, 2009, from related International Patent Application No. PCT/JP2008/003717.
European Patent Office, European Search Report mailed Nov. 25, 2010, from related EP Patent Application No. 08860790.8.

* cited by examiner

*Primary Examiner* — Sreeni Padmanabhan
*Assistant Examiner* — Sarah Pihonak
(74) *Attorney, Agent, or Firm* — Kenyon & Kenyon LLP

(57) ABSTRACT

The present invention provides a novel oxime ether derivative represented by the following formula (I), or salt thereof, that can be industrially produced advantageously, and can function as a fungicide for agricultural and horticultural use that has reliable effects and can be used safely, and a fungicide for agricultural and horticultural use that contains at least one of these compounds as an active ingredient thereof. In addition, the present invention provides a novel ketone derivative that is a production intermediate of the oxime ether derivative.

[CHEMICAL 1]

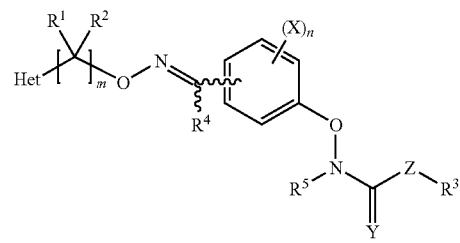

(I)

3 Claims, No Drawings

OXIME ETHER DERIVATIVE AND FUNGICIDE FOR AGRICULTURAL AND HORTICULTURAL USE

This application is a national phase application of PCT/JP2008/003717, filed on Dec. 11, 2008, which claims priority under 35 U.S.C. 119 to Japanese Patent Application Nos. 2007-319111 filed Dec. 11, 2007.

TECHNICAL FIELD

The present invention relates to a novel oxime ether derivative and salt thereof, and to a fungicide for agricultural and horticultural use that contains at least one of these compounds as an active ingredient thereof.

The present application claims priority on Japanese Patent Application No. 2007-319111, filed in Japan on Dec. 11, 2007, the content of which is incorporated herein by reference.

BACKGROUND ART

Patent Document 1 described below discloses, in relation to the present invention, an oxime ether derivative (A), which has a chemical structure as indicated below that resembles the oxime ether derivative compound of the present invention, and a fungicide for agricultural and horticultural use that contains that oxime ether derivative (A) as an active ingredient thereof.

[CHEMICAL 1]

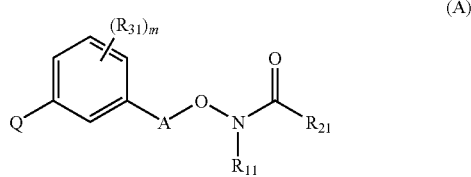

(A)

[wherein, $R_{11}$ represents a hydrogen atom, $C_{1-6}$ alkyl group, $C_{1-6}$ alkylcarbonyl group or $C_{1-6}$ alkylsulfonyl group; $R_{21}$ represents a $C_{1-6}$ alkyl group or $C_{1-6}$ alkoxy group; $R_{31}$ represents a halogen atom, $C_{1-6}$ alkyl group or $C_{1-6}$ alkoxy group; A represents an optionally branched $C_{1-6}$ alkylene group or a bond; Q represents a phenyl group which may be substituted with G, a group represented by formula (A1) or a group represented by formula (A2); and m represents 0 or an integer of 1 to 4:

[CHEMICAL 2]

(A1)

[CHEMICAL 3]

(A2)

(wherein, $R_{41}$ represents a hydrogen atom, $C_{1-6}$ alkyl group, $C_{2-6}$ alkenyl group or $SiR_{51}R_{61}R_{71}$, $R_{51}$ to $R_{71}$ each independently represent a $C_{1-6}$ alkyl group; $R_{81}$ represents a hydrogen atom, $C_{1-6}$ alkyl group, $C_{1-6}$ haloalkyl group, or phenyl group which may be substituted with G; $Y_1$ represents a hydrogen atom, $C_{1-6}$ alkyl group, $C_{3-6}$ cycloalkyl group, $C_{3-6}$ cycloalkyl-$C_{1-6}$ alkyl group, $C_{2-6}$ alkenyl group, $C_{2-6}$ alkynyl group, or phenyl $C_{1-6}$ alkyl group which may be substituted with G, and G represents a halogen atom, $C_{1-6}$ alkyl group, $C_{1-6}$ alkoxy group, $C_{1-6}$ haloalkyl group or $C_{1-6}$ haloalkoxy group, and these G may be the same or different and substitute at 2 to 5 locations)].

[Patent Document 1] Japanese Unexamined Patent Application, First Publication No. 2004-168683

DISCLOSURE OF THE INVENTION

Problems to be Solved by the Invention

Although examples of a compound related to the present invention in which Q is represented by formula (A2) have been cited, examples thereof have not been described, and the biological activity of that compound has been unknown.

With the foregoing in view, an object of the present invention is to provide a novel oxime ether derivative or salt thereof that can be industrially produced advantageously and can be an active ingredient of a fungicide for agricultural and horticultural use that demonstrates reliable effects and can be used safety, and to provide a fungicide for agricultural and horticultural use that contains at least one of these compounds as an active ingredient thereof.

Means for Solving the Problems

As a result of conducting extensive studies to solve the aforementioned problems, the inventors of the present invention found that a novel compound represented by formula (I) can actually be produced and that such compounds have superior bactericidal activity, thereby leading to completion of the present invention. Namely, the present invention relates to an oxime ether derivative represented by the following formula (I), or a salt thereof:

[CHEMICAL 4]

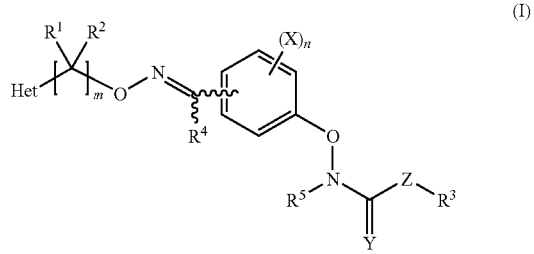

(I)

[wherein, X represents a halogen atom, $C_{1-20}$ alkyl group, $C_{1-20}$ alkoxy group, $C_{1-20}$ haloalkyl group or $C_{1-20}$ haloalkoxy group, $R^1$ and $R^2$ each independently represent a hydrogen atom, halogen atom, $C_{1-20}$ alkyl group, $C_{1-20}$ haloalkyl group, optionally substituted $C_{3-10}$ cycloalkyl group, or $R^1$ and $R^2$ may bond together to form a ring, $R^3$ represents a hydrogen atom, $C_{1-20}$ alkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group or optionally substituted $C_{3-10}$ cycloalkyl group, $R^4$ represents a hydrogen atom, $C_{1-20}$ alkyl group, optionally substituted $C_{3-10}$ cycloalkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group, cyano group, nitro group or optionally substituted amino group, $R^5$ represents a hydrogen atom, $C_{1-20}$ alkyl group, acyl group, formyl group, $C_{1-20}$ alkoxy-$C_{1-20}$ alkyl group, $C_{2-20}$ acyloxy-$C_{1-20}$ alkyl group, $C_{1-20}$ alkoxycarbonyl group, $C_{1-20}$ alkylsulfonyl group or optionally substituted phenylsulfonyl group, Y represents an oxygen atom or sulfur atom, Z represents a single bond, oxygen atom, sulfur atom or $NR^6$ (wherein, $R^6$ represents a hydrogen atom or $C_{1-30}$ alkyl group), Het represents an optionally substituted heterocyclic group, m represents an integer of 1 to 8, and $R^1$ and $R^2$ may be the same or different in the case m is 2 or more, and n represents an integer of 0 to 4, and X may be the same or different in the case n is 2 or more].

In a second aspect thereof, the present invention relates to a fungicide for agricultural and horticultural use that contains at least one of the oxime ether derivative of the present invention, or salt thereof, as an active ingredient thereof.

In a third aspect thereof, the present invention relates to a ketone derivative represented by the following formula (II). This ketone derivative is a production intermediate of the oxime ether derivative represented by formula (I).

[CHEMICAL 5]

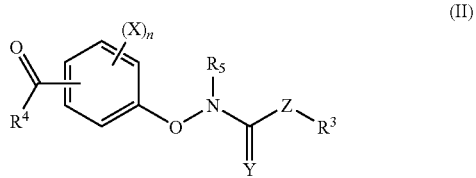

(II)

[wherein, X represents a halogen atom, $C_{1-20}$ alkyl group, $C_{1-20}$ alkoxy group, $C_{1-20}$ haloalkyl group or $C_{1-20}$ haloalkoxy group, $R^3$ represents a hydrogen atom, $C_{1-20}$ alkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group or optionally substituted $C_{3-10}$ cycloalkyl group, $R^4$ represents a hydrogen atom, $C_{1-20}$ alkyl group, optionally substituted $C_{3-10}$ cycloalkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group, cyano group, nitro group or optionally substituted amino group, $R^5$ represents a hydrogen atom, $C_{1-20}$ alkyl group, acyl group, formyl group, $C_{1-20}$ alkoxy-$C_{1-20}$ alkyl group, $C_{2-20}$ acyloxy-$C_{1-20}$ alkyl group, $C_{1-20}$ alkoxycarbonyl group, $C_{1-20}$ alkylsulfonyl group or optionally substituted phenylsulfonyl group, Y represents an oxygen atom or sulfur atom, Z represents a single bond, oxygen atom, sulfur atom or $NR^6$ (wherein, $R^6$ represents a hydrogen atom or $C_{1-30}$ alkyl group), and n represents an integer of 0 to 4, and X may be the same or different in the case n is 2 or more].

Effects of the Invention

The oxime ether derivative of the present invention, or salt thereof, is a novel compound, can be industrially produced advantageously, and is useful as an active ingredient of a fungicide for agricultural and horticultural use that has reliable effects and can be used safely.

The fungicide for agricultural and horticultural use of the present invention is a chemical agent that has superior control effects, does not cause chemical damage or contamination of plants, and has less toxicity to humans, animals and fish as well as little effect on the environment.

Furthermore, the ketone derivative of the present invention is a novel compound, and is an important key intermediate for producing the oxime ether derivative compound of the present invention.

BEST MODE FOR CARRYING OUT THE INVENTION

The following provides a detailed explanation of the present invention.
1) Oxime Ether Derivatives Represented by Formula (I) or Salt Thereof In a first aspect thereof, the present invention is an oxime ether derivative represented by the aforementioned formula (I), or a salt thereof.

In formula (I), X represents a halogen atom, $C_{1-20}$ alkyl group, $C_{1-20}$ alkoxy group, $C_{1-20}$ haloalkyl group or $C_{1-20}$ haloalkoxy group.

Examples of halogen atoms of X include a fluorine atom, chlorine atom and bromine atom.

$C_{1-20}$ alkyl groups may be linear or branched, and examples include a methyl group, ethyl group, n-propyl group, i-propyl group, n-butyl group, i-butyl group, s-butyl group, t-butyl group, n-pentyl group, n-hexyl group, n-heptyl group, n-octyl group and n-decyl group.

$C_{1-20}$ alkoxy groups may be linear or branched, and examples include a methoxy group, ethoxy group, n-propoxy group, i-propoxy group, n-butoxy group, i-butoxy group, s-butoxy group, t-butoxy group, n-pentyloxy group and n-hexyloxy group.

There are no particular limitations on the $C_{1-20}$ haloalkyl groups provided they are alkyl groups substituted with a halogen atom, specific examples of which include a fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group and pentafluoroethyl group.

There are no particular limitations on the $C_{1-20}$ haloalkoxy groups provided they are alkoxy groups substituted with a halogen atom, specific examples of which include a chloromethoxy group, dichloromethoxy group, trichloromethoxy group, trifluoromethoxy group, 1-fluoroethoxy group, 1,1-difluoroethoxy group, 2,2,2-trifluoroethoxy group and pentafluoroethoxy group.

$R^1$ and $R^2$ each independently represent a hydrogen atom, halogen atom, $C_{1-20}$ alkyl group, $C_{1-20}$ haloalkyl group or optionally substituted $C_{3-10}$ cycloalkyl group.

Specific examples of halogen atoms, $C_{1-20}$ alkyl groups and $C_{1-20}$ haloalkyl groups of $R^1$ and $R^2$ are the same as those listed as specific examples of the halogen atoms, $C_{1-20}$ alkyl groups and $C_{1-20}$ haloalkyl groups of X.

Examples of $C_{3-10}$ cycloalkyl groups of optionally substituted $C_{3-10}$ cycloalkyl groups of $R^1$ and $R^2$ include a cyclopropyl group, cyclobutyl group, cyclopentyl group, cyclohexyl group, cycloheptyl group and cyclooctyl group.

Examples of substituents of the $C_{3-10}$ cycloalkyl groups include a halogen atom such as a fluorine atom, chlorine atom or bromine atom; $C_{1-6}$ alkyl group such as a methyl group or ethyl group; $C_{1-6}$ alkoxy group such as a methoxy group or ethoxy group; nitro group; and, cyano group.

In addition, $R^1$ and $R^2$ may bond together to form a ring, and a heteroatom such as an oxygen atom, sulfur atom or nitrogen atom may be contained in the ring. Examples of such rings include a cyclopropane ring, cyclopentane ring, cyclohexane ring and tetrahydropyran ring.

$R^3$ represents a hydrogen atom, $C_{1-20}$ alkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group and optionally substituted $C_{3-10}$ cycloalkyl group.

Specific examples of $C_{1-20}$ alkyl groups, $C_{1-20}$ haloalkyl groups and optionally substituted $C_{3-10}$ cycloalkyl groups of $R^3$ are the same as those listed as specific examples of $C_{1-20}$ alkyl groups, $C_{1-20}$ haloalkyl groups and optionally substituted $C_{3-10}$ cycloalkyl groups of X, $R^1$ and $R^2$.

Examples of $C_{2-20}$ alkenyl groups of $R^3$ include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

Examples of $C_{2-20}$ alkynyl groups include an ethynyl group, 1-propynyl group, propargyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

Examples of $C_{2-20}$ haloalkenyl groups include a 3-chloro-2-propenyl group, 4-chloro-2-butenyl group, 4,4-dichloro-3-butenyl group, 4,4-difluoro-3-butenyl group and 3,3-dichloro-2-propenyl group.

Examples of $C_{2-20}$ haloalkynyl groups include a 3-chloro-1-propynyl group, 3-chloro-1-butynyl group, 3-bromo-1-butynyl group, 3-bromo-2-propynyl group and 3-iodo-2-propynyl group.

$R^4$ represents a hydrogen atom, $C_{1-20}$ alkyl group, optionally substituted $C_{3-10}$ cycloalkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group, cyano group, nitro group or optionally substituted amino group.

Specific examples of $C_{1-20}$ alkyl groups of $R^4$ are the same as those listed as specific examples of $C_{1-20}$ alkyl groups of X.

Specific examples of optionally substituted $C_{3-10}$ cycloalkyl groups of $R^4$ are the same as those listed as specific examples of optionally substituted $C_{3-10}$ cycloalkyl groups of $R^1$.

Specific examples of $C_{2-20}$ alkenyl groups, $C_{2-20}$ alkynyl groups, $C_{1-20}$ haloalkyl groups, $C_{2-20}$ haloalkenyl groups and $C_{2-20}$ haloalkynyl groups of $R^4$ are the same as those listed as specific examples of $C_{2-20}$ alkenyl groups, $C_{2-20}$ alkynyl groups, $C_{1-20}$ haloalkyl groups, $C_{2-20}$ haloalkenyl groups and $C_{2-20}$ haloalkynyl groups of $R^3$.

Examples of optionally substituted amino groups of $R^4$ include an amino group; mono ($C_{1-6}$) alkylamino groups such as a methylamino group, ethylamino group or i-propylamino group; di($C_{1-6}$) alkylamino groups such as a dimethylamino group or diethylamino group; acylamino groups such as an acetylamino group or benzoylamino group; and, optionally substituted phenylamino groups such as a phenylamino group or 4-methylphenylamino group.

$R^5$ represents a hydrogen atom, $C_{1-20}$ alkyl group, acyl group, formyl group, $C_{1-20}$ alkoxy-$C_{1-20}$ alkyl group, $C_{2-20}$ acyloxy-$C_{1-20}$ alkyl group, $C_{1-20}$ alkoxycarbonyl group, $C_{1-20}$ alkylsulfonyl group or optionally substituted phenylsulfonyl group.

Specific examples of $C_{1-20}$ alkyl groups of $R^5$ are the same as those listed as specific examples of $C_{1-20}$ alkyl groups of X.

Examples of acyl groups include an acetyl group, propionyl group, pivaloyl group, trifluoroacetyl group, trichloroacetyl group, benzoyl group, 4-methylbenzoyl group and 2-chlorobenzoyl group.

Examples of $C_{1-20}$ alkoxy-$C_{1-20}$ alkyl groups of $R^5$ include a methoxymethyl group, ethoxymethyl group, i-propoxymethyl group, 1-methoxyethyl group, 2-methoxyethyl group, 1-ethoxyethyl group, 2-ethoxyethyl group, 1-methoxy-n-propyl group, 2-methoxy-n-propyl group and 3-methoxy-n-propyl group.

Examples of $C_{2-20}$ acyloxy-$C_{1-20}$ alkyl groups of $R^5$ include an acetoxymethyl group, acetoxyethyl group, propionyloxymethyl group, pivaloyloxymethyl group, 1-acetoxyethyl group, 2-acetoxyethyl group and 1-acetoxy-n-propyl group.

Examples of $C_{1-20}$ alkoxycarbonyl groups of $R^5$ include a methoxycarbonyl group, ethoxycarbonyl group, isopropoxycarbonyl group, n-butoxycarbonyl group and t-butoxycarbonyl group.

Examples of $C_{1-20}$ alkylsulfonyl groups include a methylsulfonyl group, ethylsulfonyl group, n-propylsulfonyl group and i-propylsulfonyl group.

Examples of optionally substituted phenylsulfonyl groups include a phenylsulfonyl group, 4-methylphenylsulfonyl group, 2-chlorophenylsulfonyl group and 2,4-dimethylphenylsulfonyl group.

Y represents an oxygen atom or sulfur atom.

Z represents a single bond, oxygen atom, sulfur atom or group represented by $NR^6$.

$R^6$ represents a hydrogen atom or a $C_{1-30}$ alkyl group such as methyl group, ethyl group, n-propyl group, i-propyl group, n-butyl group or t-butyl group.

Het represents an optionally substituted heterocyclic group. The heterocyclic group is a saturated or unsaturated heterocyclic group containing 1 to 4 N, O or S atoms in the ring thereof, and is preferably a 5-member or 6-member heterocyclic group.

Specific examples of heterocyclic groups include unsaturated 5-member heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group; unsaturated 6-member heterocyclic groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; and saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, piperazino group, N-methylpiperazino group, aziridino group, azetidino group, pyrrolidino group, or oxazolin-2-yl group.

Examples of substituents of the above-mentioned heterocyclic groups include halogen atoms such as a fluorine atom, chlorine atom or bromine atom; $C_{1-6}$ alkyl groups such as a methyl group, ethyl group, n-propyl group, i-propyl group, n-butyl group, s-butyl group, i-butyl group or t-butyl group; $C_{1-6}$ alkoxy groups such as a methoxy group, ethoxy group, propoxy group, i-propoxy group, n-butoxy group, s-butoxy group, i-butoxy group or t-butoxy group; $C_{1-6}$ haloalkoxy groups such as a chloromethoxy group or trifluoromethoxy group; $C_{1-6}$ alkylthio groups such as a methylthio group, ethylthio group, n-propylthio group, i-propylthio group, n-butylthio group, i-butylthio group, s-butylthio group or t-butylthio group; $C_{1-6}$ alkylsulfonyl groups such as a methylsulfonyl group, ethylsulfonyl group, i-propylsulfonyl group or n-butylsulfonyl group; $C_{1-6}$ haloalkyl groups such as a chloromethyl group, fluoromethyl group or trifluoromethyl group; and, $C_{1-6}$ alkylsulfonyloxy groups such as a methylsulfonyloxy group, ethylsulfonyloxy group, i-propylsulfonyloxy group or n-butylsulfonyloxy group.

m represents an integer of 1 to 8 and is preferably an integer of 1 to 3.

n represents an integer of 0 to 4 and is preferably an integer of 0 to 2.

In the present invention, an oxime ether derivative represented by the aforementioned formula (I) is preferably a compound represented by the following formula (I-1):

[CHEMICAL 6]

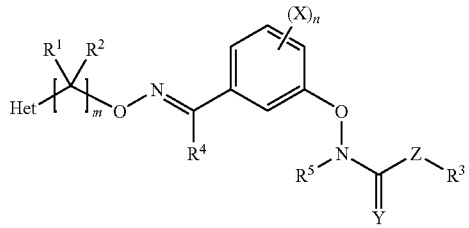

(I-1)

(wherein, $R^1$ to $R^5$, X, Y, Z, Het, m and n are the same as previously defined), and more preferably a compound represented by the following formula (I-1a):

[CHEMICAL 7]

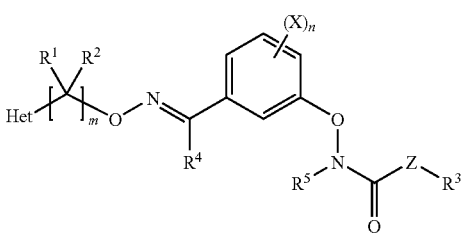

(I-1a)

(wherein, $R^1$ to $R^5$, X, Z, Het, m and n are the same as previously defined).

(Production Method)

An oxime ether derivative compound of the present invention can be produced, for example, in the manner described below:

[CHEMICAL 8]

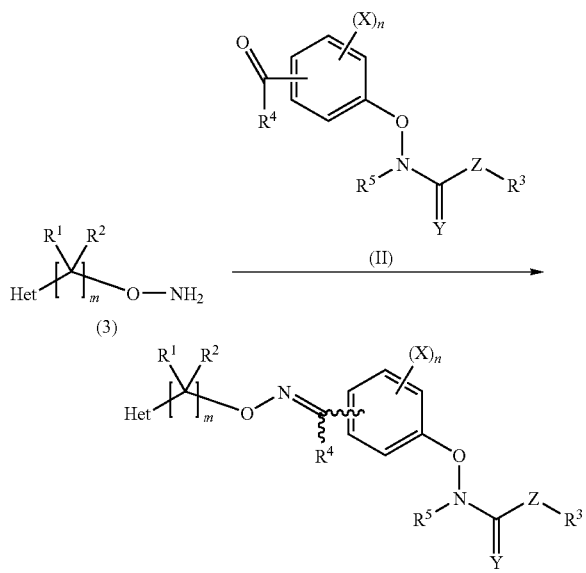

(wherein, $R^1$ to $R^5$, X, Z, Het, Y, m and n are the same as previously defined).

Namely, a compound represented by formula (I) can be obtained by reacting an oxyamine compound represented by formula (3) with a ketone compound represented by formula (II) (to also be referred to as "compound (II)").

Furthermore, compound (II) is a novel compound that is an important key intermediate in the production of a compound represented by formula (I) of the present invention. A third aspect of the present invention is a ketone derivative represented by this compound (II).

The amount of the compound (II) used is normally 0.5 to 2 times moles and preferably 0.7 to 1.5 times moles the oxyamine compound represented by formula (3).

Although the reaction can also be carried out in the absence of a catalyst, it is preferably carried out in the presence of an acid catalyst or basic catalyst, and is more preferably carried out in the presence of an acid catalyst.

Examples of acid catalysts used include trifluoroacetic acid, benzenesulfonic acid, p-toluenesulfonic acid, p-toluenesulfonic acid monohydrate, methanesulfonic acid, pyridinium p-toluenesulfonate, hydrochloric acid and sulfuric acid. Examples of basic catalysts include pyridine, triethylamine and potassium hydroxide.

The amount of catalyst used is normally 0.0001 to 1 times moles the oxyamine compound represented by formula (3).

In addition, a dehydrating agent such as anhydrous sodium sulfate or molecular sieve may also be added to the reaction system.

The reaction can be carried out in a suitable solvent. There are no particular limitations on the solvent used provided it is inert in the reaction. Examples of solvents include ether-based solvents such as dioxane, 1,2-dimethoxyethane or tetrahydrofuran; aromatic hydrocarbon-based solvents such as toluene, benzene or xylene; aliphatic hydrocarbon-based solvents such as n-pentane, n-hexane or n-heptane; halogenated hydrocarbon-based solvents such as dichloromethane, chloroform, carbon tetrachloride or 1,2-dichloroethane; amide-based solvents such as N,N-dimethylformamide, N,N-dimethylacetamide or N-methylpyrrolidone; nitrile-based solvents such as acetonitrile or benzonitrile; alcohol-based solvents such as methanol, ethanol or n-propanol; and mixed solvents composed of two more of these solvents.

Although there are no particular limitations on the amount of solvent used, it is normally 1 to 100 ml based on 1 g of the oxyamine compound represented by formula (3).

The reaction temperature is within a temperature range from room temperature to the boiling point of the solvent used. The reaction time is normally from several minutes to several tens of hours.

The oxyamine compound represented by formula (3) can be produced by a conventionally known method for producing oxyamine compounds. For example, as indicated below, an oxyamine compound represented by formula (3) can be obtained by reacting carbon tetrabromide and triphenylphosphine with a compound represented by formula (1) to obtain a compound represented by formula (2), reacting N-t-butoxy-carbonylhydroxylamine therewith in the presence of base to obtain an oxyamine compound represented by formula (9), and allowing an acid to act thereon:

[CHEMICAL 9]

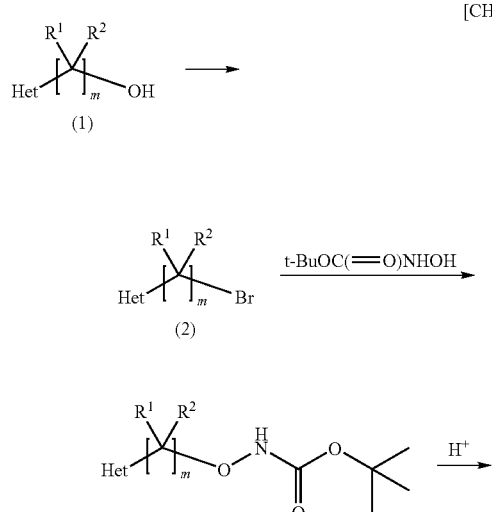

(wherein, $R^1$, $R^2$, Het and m are the same as previously defined).

In addition, in the case of reacting an oxyamine compound represented by formula (3) with compound (4), the reaction may be carried out by mixing compound (II) with an oxyamine compound represented by formula (9) followed by adding an acid such as trifluoroacetic acid to form a compound represented by formula (3) within the reaction system.

Compound (II) can be produced, for example, in the manner indicated below:

[CHEMICAL 10]

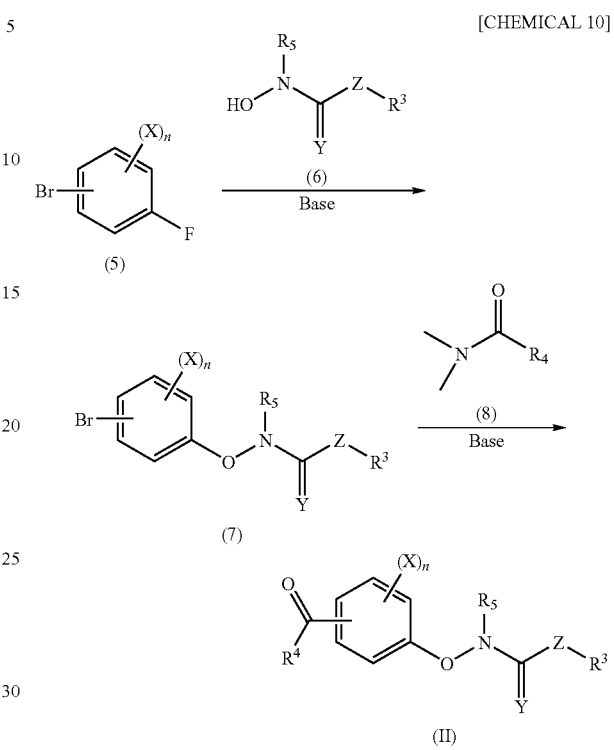

(wherein, X, n, $R^3$ to $R^5$, Y and Z are the same as previously defined).

Namely, a hydroxycarbamic acid compound represented by formula (7) (to also be referred to as "compound (7)") is obtained by reacting a compound represented by formula (6) (to also be referred to as "compound (6)") with a fluoride compound represented by formula (5) (to also be referred to as "compound (5)") in the presence of base. Next, the target compound (II) is obtained by reacting an amide compound represented by formula (8) (to also be referred to as "compound (8)") with compound (7) in the presence of base.

In the reaction for obtaining compound (7), the amount of compound (6) used is normally 0.8 to 5 times moles and preferably 1 to 3 times moles based on 1 mole of compound (5).

Examples of base used in the reaction for obtaining compound (7) include metal hydroxides such as lithium hydroxide, sodium hydroxide, potassium hydroxide, magnesium hydroxide or calcium hydroxide; metal alkoxides such as sodium methoxide, sodium ethoxide, potassium methoxide, potassium ethoxide or potassium t-butoxide; metal hydrides such as sodium hydride, potassium hydride or calcium hydride; and organic bases such as triethylamine, diisopropylethylamine, pyridine, 1,8-diazabicylo[5.4.0]undec-7-ene (DBU) or 1,4-diazabicylo[2.2.2]octane.

The amount of base used is normally 1 to 20 times moles based on 1 mole of compound (5).

This reaction can be carried out in a suitable organic solvent. There are no particular limitations on the organic solvent used provided it is inert in the reaction. Examples of organic solvents include sulfur-containing solvents such as dimethylsulfoxide or diethylsulfoxide; ether-based solvents such as dioxane, 1,2-dimethoxyethane or tetrahydrofuran;

aromatic hydrocarbon-based solvents such as toluene, benzene or xylene; aliphatic hydrocarbon-based solvents such as n-pentane, n-hexane or n-heptane; amide-based solvents such as N,N-dimethylformamide, N,N-dimethylacetamide or N-methylpyrrolidone; nitrile-based solvents such as acetonitrile or benzonitrile; and mixed solvents composed of two or more of these solvents.

Although there are no particular limitations on the amount of organic solvent used, it is normally 1 to 100 ml based on 1 g of compound (5).

The reaction for obtaining compound (7) proceeds smoothly within a temperature range from 0° C. to the boiling point of the solvent.

Specific examples of compound (8) used in the reaction for obtaining compound (II) include N,N-dimethylacetamide and N,N-dimethylpropionamide.

The amount of compound (8) used is normally 0.8 to 5 times moles and preferably 1 to 3 times moles based on 1 mole of compound (7).

Examples of base used in the reaction for obtaining compound (II) include organic lithium compounds such as n-butyllithium, sec-butyllithium, t-butyllithium or lithium diisopropylamide; alkaline metals such as sodium metal or potassium metal; and metal hydrides such as sodium hydride, potassium hydride or calcium hydride.

The amount of base used is normally 1 to 20 times moles based on 1 mole of compound (7).

This reaction can be carried out in a suitable organic solvent. There are no particular limitations on the solvent used provided it is inert in the reaction. Examples of organic solvents include ether-based solvents such as dioxane, 1,2-dimethoxyethane or tetrahydrofuran; aromatic hydrocarbon-based solvents such as toluene, benzene or xylene; and aliphatic hydrocarbon-based solvents such as n-pentane, n-hexane or n-heptane.

The reaction for obtaining compound (II) proceeds smoothly within a temperature range from −100° C. to the boiling point of the solvent used.

Among compounds represented by formula (II), a compound (II-a), in which $R^3$ is a t-butyl group, $R^5$ is a hydrogen atom and Y and Z are oxygen atoms, can be derived to a compound (II-c), in which the t-butyl group is replaced with another substituent $R^{3'}$ (wherein, $R^{3'}$ is the same as the previously defined $R^3$ except for a t-butyl group) according to a known method as indicated below:

[CHEMICAL 11]

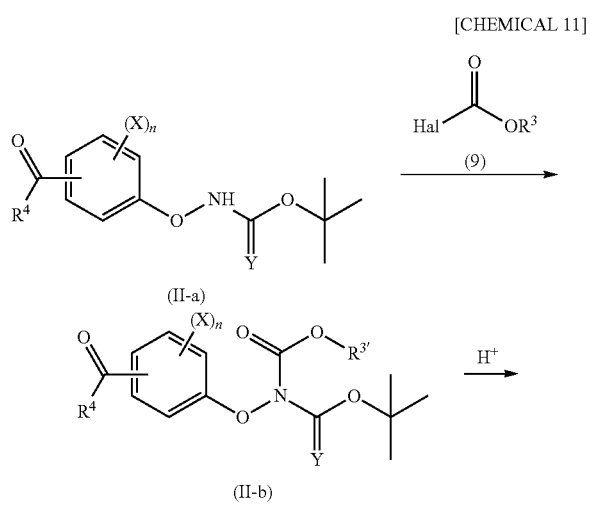

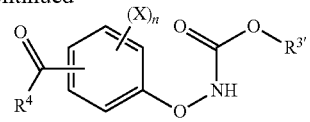

(II-c)

(wherein, X, n, $R^4$ are the same as previously defined, and Hal represents a halogen atom such as a chlorine atom or bromine atom).

Namely, a compound represented by formula (II-b) is first obtained by reacting a halogenoxy acid ester compound represented by formula (9) with a carbamic acid t-butyl ester compound represented by formula (II-a) in the presence of base. Next, a compound represented by formula (II-c) can be obtained by allowing an acid to act thereon.

Examples of base used in the reaction for reacting the halogenoxy acid ester compound represented by formula (9) include metal hydroxides such as lithium hydroxide, sodium hydroxide, potassium hydroxide, magnesium hydroxide or calcium hydroxide; metal alkoxides such as sodium methoxide, sodium ethoxide, potassium methoxide, potassium ethoxide or potassium t-butoxide; metal hydrides such as sodium hydride, potassium hydride or calcium hydride; and organic bases such as triethylamine, diisopropylethylamine, pyridine, 1,8-diazabicylo[5.4.0]undec-7-ene (DBU) or 1,4-diazabicylo[2.2.2]octane.

The amount of base used is normally 1 to 20 times moles based on 1 mole of compound (II-a).

The reaction for reacting the halogenoxy acid ester compound represented by formula (9) is carried out in a suitable organic solvent. There are no particular limitations on the organic solvent used provided it is inert in the reaction. Examples of organic solvents include halogenated hydrocarbons such as methylene chloride, chloroform, carbon tetrachloride or 1,2-dichloroethane; sulfur-containing solvents such as dimethylsulfoxide or diethylsulfoxide; ether-based solvents such as dioxane, 1,2-dimethoxyethane or tetrahydrofuran; aromatic hydrocarbon-based solvents such as toluene, benzene or xylene; aliphatic hydrocarbon-based solvents such as n-pentane, n-hexane or n-heptane; amide-based solvents such as N,N-dimethylformamide, N,N-dimethylacetamide or N-methylpyrrolidone; nitrile-based solvents such as acetonitrile or benzonitrile; and mixed solvents composed of two or more of these solvents.

Although there are no particular limitations on the amount of organic solvent used, it is normally 1 to 100 ml based on 1 g of compound (II-b).

The reaction for reacting the halogenoxy acid ester compound represented by formula (9) proceeds smoothly within a temperature range from −20° C. to the boiling point of the solvent used.

Although varying according to the reaction scale, the reaction time is normally from several minutes to several tens of hours.

Examples of acids used in the reaction for obtaining a compound represented by formula (II-c) from a compound represented by formula (II-b) include inorganic acids such as hydrochloric acid, sulfuric acid or nitric acid; acetic acid, trifluoroacetic acid, methanesulfonic acid and p-toluenesulfonic acid.

The amount of acid used is normally 1 to 20 times moles based on 1 mole of compound (II-b).

The reaction for obtaining a compound represented by formula (II-c) from a compound represented by formula (II-b) is carried out in a suitable organic solvent.

There are no particular limitations on the organic solvent used provided it is inert in the reaction, and examples of organic solvents used include the same organic solvents listed as examples of solvents able to be used in the reaction for reacting the halogenoxy acid ester compound represented by formula (9).

The reaction for obtaining a compound represented by formula (II-c) from a compound represented by formula (II-b) proceeds smoothly within a temperature range from −20° C. to the boiling point of the solvent used.

Although varying according to the reaction scale, the reaction time is normally from several minutes to several tens of hours.

In addition, among compounds represented by formula (II), compound (II-d), in which Y and Z are oxygen atoms, can be derived to compound (II-e), in which substituent $R^3$ is converted to another substituent $R^{3'''}$, by a known transesterification method (as indicated by the following reaction formula):

[CHEMICAL 12]

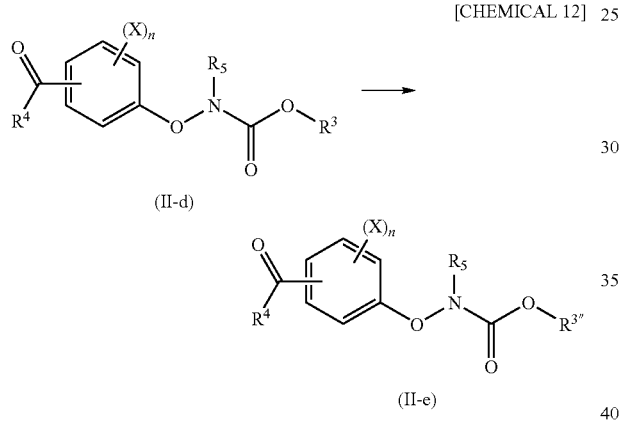

(wherein, X, n and $R^3$ to $R^5$ are the same as previously defined, and $R^{3'''}$ is defined in the same manner as $R^3$, provided that $R^3$ and $R^{3'''}$ are not the same).

There are no particular limitations on salts of the oxime ether derivative compound of the present invention provided it is an agriculturally and horticulturally acceptable salt. Examples of salts include salts of inorganic acids such as hydrochlorides or sulfates; and salts of organic acids such as acetates or lactates.

These salts can be produced in accordance with conventionally known methods using an oxime ether derivative represented by the aforementioned formula (I) and a corresponding acid.

In any of the reactions, a target compound can be isolated by carrying out an ordinary post-treatment procedure following completion of the reaction and purifying by known, commonly used purification means such as distillation, recrystallization or column chromatography as desired.

The structure of a target compound can be identified and confirmed by known analysis means such as IR spectroscopy, NMR spectroscopy, mass spectrometry or elementary analysis.

Although geometrical isomers (cis and trans isomers) based on carbon-nitrogen double bonds exist for the oxime ether derivative of the present invention, all of these isomers are included in the present invention.

Examples of the oxime ether derivative of the present invention obtained in the manner described above are shown in the following first tables (Tables 1 to 33). In the first tables, although only one of the geometrical isomers of the oxime ether derivatives are shown, the other geometrical isomer can be similarly exemplified.

In the following chemical formulas, r represents a $C_{1-6}$ alkyl group such as a methyl group or ethyl group; $C_{1-6}$ haloalkyl group such as a trifluoromethyl group; $C_{1-6}$ alkoxy group such as a methoxy group or ethoxy group; $C_{1-6}$ haloalkoxy group such as a trifluoromethoxy group; or halogen atom such as a fluorine atom, chlorine atom or bromine atom. t1 represents an integer of 0 to 2, t2 represents an integer of 0 to 3, and t3 represents an integer of 0 to 4. In the case t1 is 2 or in the case t2 or t3 is 2 or more, r may be the same or different.

In addition, in the following first tables, Et represents an ethyl group, Ph a phenyl group, c-Pr a cyclopropyl group, and di indicates di-substitution, while an asterisk (*) indicates the location of a bond. In addition, in the tables, numbers indicated in the r and X columns represent their respective substituted locations.

In addition, only one of the stereoisomers in a C═N double bond is assumed to not be represented.

[CHEMICAL 13]

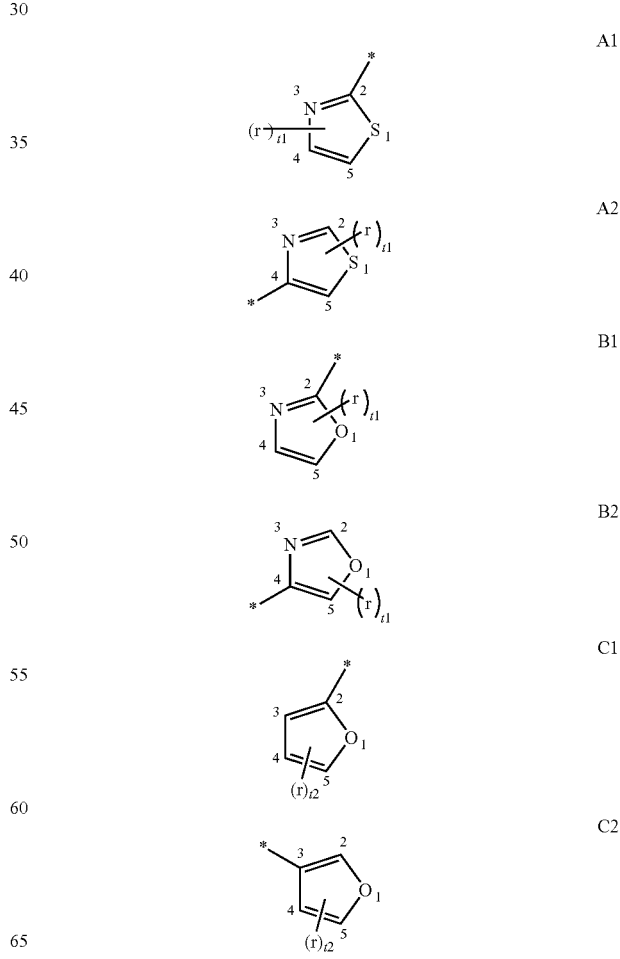

-continued

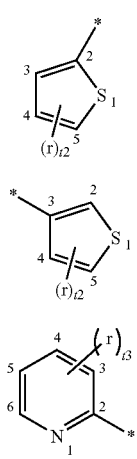

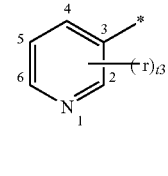

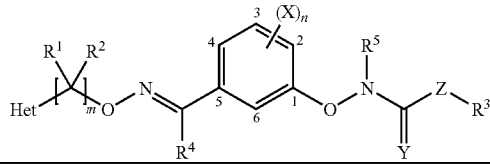

(First Tables)

TABLE 1

(I-1)

| No | Het | r | R¹ | R² | m | R⁴ | R⁵ | X | n | Y | Z | R³ |
|---|---|---|---|---|---|---|---|---|---|---|---|---|
| 1 | A1 | — | H | H | 1 | CH₃ | H | — | 0 | O | O | CH₃ |
| 2 | A1 | — | H | H | 1 | CH₃ | H | 2-Cl | 1 | O | O | CH₃ |
| 3 | A1 | 4-CH₃ | H | H | 1 | CH₃ | H | 2-Cl | 1 | O | O | CH₃ |
| 4 | A1 | 4-Et | H | H | 1 | CH₃ | H | 2-Cl | 1 | O | O | CH₃ |
| 5 | A1 | 4-CF₃ | H | H | 1 | CH₃ | H | 2-Cl | 1 | O | O | CH₃ |
| 6 | A1 | 4-F | H | H | 1 | CH₃ | H | 2-Cl | 1 | O | O | CH₃ |
| 7 | A1 | 4-Cl | H | H | 1 | CH₃ | H | 2-Cl | 1 | O | O | CH₃ |
| 8 | A1 | 4-OCH₃ | H | H | 1 | CH₃ | H | 2-Cl | 1 | O | O | CH₃ |
| 9 | A1 | 4-OEt | H | H | 1 | CH₃ | H | 2-Cl | 1 | O | O | CH₃ |
| 10 | A1 | 4-OCF₃ | H | H | 1 | CH₃ | H | 2-Cl | 1 | O | O | CH₃ |
| 11 | A1 | 5-CH₃ | H | H | 1 | CH₃ | H | 2-Cl | 1 | O | O | CH₃ |
| 12 | A1 | 5-Et | H | H | 1 | CH₃ | H | 2-Cl | 1 | O | O | CH₃ |
| 13 | A1 | 5-CF₃ | H | H | 1 | CH₃ | H | 2-Cl | 1 | O | O | CH₃ |
| 14 | A1 | 5-F | H | H | 1 | CH₃ | H | 2-Cl | 1 | O | O | CH₃ |
| 15 | A1 | 5-Cl | H | H | 1 | CH₃ | H | 2-Cl | 1 | O | O | CH₃ |
| 16 | A1 | 5-OCH₃ | H | H | 1 | CH₃ | H | 2-Cl | 1 | O | O | CH₃ |
| 17 | A1 | 5-OEt | H | H | 1 | CH₃ | H | 2-Cl | 1 | O | O | CH₃ |
| 18 | A1 | 5-OCF₃ | H | H | 1 | CH₃ | H | 2-Cl | 1 | O | O | CH₃ |
| 19 | A1 | 4,5-diCH₃ | H | H | 1 | CH₃ | H | 2-Cl | 1 | O | O | CH₃ |
| 20 | A1 | 4-Et-5-OH₃ | H | H | 1 | CH₃ | H | 2-Cl | 1 | O | O | CH₃ |
| 21 | A1 | 4-CF₃-5-F | H | H | 1 | CH₃ | H | 2-Cl | 1 | O | O | CH₃ |
| 22 | A1 | 4,5-diF | H | H | 1 | CH₃ | H | 2-Cl | 1 | O | O | CH₃ |
| 23 | A1 | 4-Cl-5-F | H | H | 1 | CH₃ | H | 2-Cl | 1 | O | O | CH₃ |
| 24 | A1 | 4,5-diOCH₃ | H | H | 1 | CH₃ | H | 2-Cl | 1 | O | O | CH₃ |
| 25 | A1 | 4-OEt-5-CH₃ | H | H | 1 | CH₃ | H | 2-Cl | 1 | O | O | CH₃ |
| 26 | A1 | 4-OCF₃-5-F | H | H | 1 | CH₃ | H | 2-Cl | 1 | O | O | CH₃ |
| 27 | A1 | 4-CH₃ | H | CH₃ | 1 | CH₃ | H | 2-Cl | 1 | O | O | CH₃ |
| 28 | A1 | 4-Et | H | CH₃ | 1 | CH₃ | H | 2-Cl | 1 | O | O | CH₃ |
| 29 | A1 | 4-CH₃ | H | Et | 1 | CH₃ | H | 2-Cl | 1 | O | O | CH₃ |
| 30 | A1 | 4-CH₃ | H | i-Pr | 1 | CH₃ | H | 2-Cl | 1 | O | O | CH₃ |
| 31 | A1 | 4-CH₃ | CH₃ | Et | 1 | CH₃ | H | 2-Cl | 1 | O | O | CH₃ |
| 32 | A1 | 4-CH₃ | H | F | 1 | CH₃ | H | 2-Cl | 1 | O | O | CH₃ |
| 33 | A1 | 4-CH₃ | F | F | 1 | CH₃ | H | 2-Cl | 1 | O | O | CH₃ |
| 34 | A1 | 4-CH₃ | H | CF3 | 1 | CH₃ | H | 2-Cl | 1 | O | O | CH₃ |
| 35 | A1 | 4-CH₃ | H | c-Pr | 1 | CH₃ | H | 2-Cl | 1 | O | O | CH₃ |
| 36 | A1 | 4-CH₃ | —CH₂CH₂— | | 1 | CH₃ | H | 2-Cl | 1 | O | O | CH₃ |
| 37 | A1 | 4-CH₃ | —CH₂CH₂CH₂— | | 1 | CH₃ | H | 2-Cl | 1 | O | O | CH₃ |
| 38 | A1 | 4-CH₃ | —CH₂CH(CH₃)— | | 1 | CH₃ | H | 2-Cl | 1 | O | O | CH₃ |
| 39 | A1 | 4-CH₃ | —CH₂C(CH₃)2— | | 1 | CH₃ | H | 2-Cl | 1 | O | O | CH₃ |
| 40 | A1 | 4-CH₃ | H | H | 1 | H | H | 2-Cl | 1 | O | O | CH₃ |
| 41 | A1 | 4-CH₃ | H | H | 1 | Et | H | 2-Cl | 1 | O | O | CH₃ |
| 42 | A1 | 4-CH₃ | H | H | 1 | c-Pr | H | 2-Cl | 1 | O | O | CH₃ |

TABLE 1-continued (I-1)

| No | Het | r | R¹ | R² | m | R⁴ | R⁵ | X | n | Y | Z | R³ |
|---|---|---|---|---|---|---|---|---|---|---|---|---|
| 43 | A1 | 4-CH₃ | H | H | 1 | CH=CH₂ | H | 2-Cl | 1 | O | O | CH₃ |
| 44 | A1 | 4-CH₃ | H | H | 1 | CH₂CH=CH₂ | H | 2-Cl | 1 | O | O | CH₃ |
| 45 | A1 | 4-CH₃ | H | H | 1 | ethynyl | H | 2-Cl | 1 | O | O | CH₃ |
| 46 | A1 | 4-CH₃ | H | H | 1 | Propargyl | H | 2-Cl | 1 | O | O | CH₃ |
| 47 | A1 | 4-CH₃ | H | H | 1 | CF₃ | H | 2-Cl | 1 | O | O | CH₃ |
| 48 | A1 | 4-CH₃ | H | H | 1 | CH=CHCl | H | 2-Cl | 1 | O | O | CH₃ |
| 49 | A1 | 4-CH₃ | H | H | 1 | 3,3,2-tri-Iodo-allyl | H | 2-Cl | 1 | O | O | CH₃ |
| 50 | A1 | 4-CH₃ | H | H | 1 | 3-Iodopropargyl | H | 2-Cl | 1 | O | O | CH₃ |
| 51 | A1 | 4-CH₃ | H | H | 1 | CN | H | 2-Cl | 1 | O | O | CH₃ |
| 52 | A1 | 4-CF₃ | H | H | 1 | CN | H | 2-Cl | 1 | O | O | CH₃ |

TABLE 2

| No | Het | r | R¹ | R² | m | R⁴ | R⁵ | X | n | Y | Z | R³ |
|---|---|---|---|---|---|---|---|---|---|---|---|---|
| 53 | A1 | 4-CH₃ | H | H | 1 | NO₂ | H | 2-Cl | 1 | O | O | CH₃ |
| 54 | A1 | 4-CH₃ | H | H | 1 | NH₂ | H | 2-Cl | 1 | O | O | CH₃ |
| 55 | A1 | 4-CH₃ | H | H | 1 | NHCH₃ | H | 2-Cl | 1 | O | O | CH₃ |
| 56 | A1 | 4-CH₃ | H | H | 1 | N(CH₃)₂ | H | 2-Cl | 1 | O | O | CH₃ |
| 57 | A1 | 4-CH₃ | H | H | 1 | CH₃ | CH₃ | 2-Cl | 1 | O | O | CH₃ |
| 58 | A1 | 4-CH₃ | H | H | 1 | CH₃ | Et | 2-Cl | 1 | O | O | CH₃ |
| 59 | A1 | 4-CH₃ | H | H | 1 | CH₃ | CH₃CO | 2-Cl | 1 | O | O | CH₃ |
| 60 | A1 | 4-CH₃ | H | H | 1 | CH₃ | CH₃CH₂CO | 2-Cl | 1 | O | O | CH₃ |
| 61 | A1 | 4-CH₃ | H | H | 1 | CH₃ | PhCO | 2-Cl | 1 | O | O | CH₃ |
| 62 | A1 | 4-CH₃ | H | H | 1 | CH₃ | 4-Cl-PhCO | 2-Cl | 1 | O | O | CH₃ |
| 63 | A1 | 4-CH₃ | H | H | 1 | CH₃ | PhCH₂CO | 2-Cl | 1 | O | O | CH₃ |
| 64 | A1 | 4-CH₃ | H | H | 1 | CH₃ | CHO | 2-Cl | 1 | O | O | CH₃ |
| 65 | A1 | 4-CH₃ | H | H | 1 | CH₃ | CH₃OCH₂ | 2-Cl | 1 | O | O | CH₃ |
| 66 | A1 | 4-CH₃ | H | H | 1 | CH₃ | CH₃CH(OCH₃) | 2-Cl | 1 | O | O | CH₃ |
| 67 | A1 | 4-CH₃ | H | H | 1 | CH₃ | CH₃SO₂ | 2-Cl | 1 | O | O | CH₃ |
| 68 | A1 | 4-CH₃ | H | H | 1 | CH₃ | PhSO₂ | 2-Cl | 1 | O | O | CH₃ |
| 69 | A1 | 4-CH₃ | H | H | 1 | CH₃ | 4-CH₃-PhSO₂ | 2-Cl | 1 | O | O | CH₃ |
| 70 | A1 | 4-CH₃ | H | H | 1 | CH₃ | H | 2-Cl | 1 | S | O | CH₃ |
| 71 | A1 | 4-CH₃ | H | H | 1 | CH₃ | H | 2-Cl | 1 | O | S | CH₃ |
| 72 | A1 | 4-CH₃ | H | H | 1 | CH₃ | H | 2-Cl | 1 | O | — | CH₃ |
| 73 | A1 | 4-CH₃ | H | H | 1 | CH₃ | H | 2-Cl | 1 | O | NH | CH₃ |
| 74 | A1 | 4-CH₃ | H | H | 1 | CH₃ | H | 2-Cl | 1 | O | NCH₃ | CH₃ |
| 75 | A1 | 4-CH₃ | H | H | 1 | CH₃ | H | 2-Cl | 1 | O | O | H |
| 76 | A1 | 4-CH₃ | H | H | 1 | CH₃ | H | 2-Cl | 1 | O | O | Et |
| 77 | A1 | 4-CH₃ | H | H | 1 | CH₃ | H | 2-Cl | 1 | O | O | n-Pr |
| 78 | A1 | 4-CH₃ | H | H | 1 | CH₃ | H | 2-Cl | 1 | O | O | CH₂CH=CH₂ |
| 79 | A1 | 4-CH₃ | H | H | 1 | CH₃ | H | 2-Cl | 1 | O | O | CH=CH₂ |
| 80 | A1 | 4-CH₃ | H | H | 1 | CH₃ | H | 2-Cl | 1 | O | O | Propargyl |
| 81 | A1 | 4-CH₃ | H | H | 1 | CH₃ | H | 2-Cl | 1 | O | O | ethynyl |
| 82 | A1 | 4-CH₃ | H | H | 1 | CH₃ | H | 2-Cl | 1 | O | O | CF₃ |
| 83 | A1 | 4-CH₃ | H | H | 1 | CH₃ | H | 2-Cl | 1 | O | O | CH₂CF₃ |
| 84 | A1 | 4-CH₃ | H | H | 1 | CH₃ | H | 2-Cl | 1 | O | O | CF₂CF₃ |
| 85 | A1 | 4-CH₃ | H | H | 1 | CH₃ | H | 2-Cl | 1 | O | O | CF₂CF₂H |
| 86 | A1 | 4-CH₃ | H | H | 1 | CH₃ | H | 2-Cl | 1 | O | O | CH₂CH=CHCl |
| 87 | A1 | 4-CH₃ | H | H | 1 | CH₃ | H | 2-Cl | 1 | O | O | 3-Iodo-propargyl |
| 88 | A1 | 4-CH₃ | H | H | 1 | CH₃ | H | 2-Cl | 1 | O | O | c-Pr |
| 89 | A1 | 4-CH₃ | H | H | 1 | CH₃ | H | 2-Cl | 1 | O | O | c-Hex |
| 90 | A1 | 4-CH₃ | H | H | 1 | CH₃ | H | 2-Cl | 1 | O | O | 2-CH₃-c-Pr |
| 91 | A1 | — | H | H | 1 | CH₃ | H | 2-CH₃ | 1 | O | O | CH₃ |
| 92 | A1 | 4-CH₃ | H | H | 1 | CH₃ | H | 2-CH₃ | 1 | O | O | CH₃ |
| 93 | A1 | 4-Et | H | H | 1 | CH₃ | H | 2-CH₃ | 1 | O | O | CH₃ |
| 94 | A1 | 4-CF₃ | H | H | 1 | CH₃ | H | 2-CH₃ | 1 | O | O | CH₃ |
| 95 | A1 | 4-F | H | H | 1 | CH₃ | H | 2-CH₃ | 1 | O | O | CH₃ |
| 96 | A1 | 4-Cl | H | H | 1 | CH₃ | H | 2-CH₃ | 1 | O | O | CH₃ |
| 97 | A1 | 4-OCH₃ | H | H | 1 | CH₃ | H | 2-CH₃ | 1 | O | O | CH₃ |
| 98 | A1 | 4-OEt | H | H | 1 | CH₃ | H | 2-CH₃ | 1 | O | O | CH₃ |
| 99 | A1 | 4-OCF₃ | H | H | 1 | CH₃ | H | 2-CH₃ | 1 | O | O | CH₃ |
| 100 | A1 | 5-CH₃ | H | H | 1 | CH₃ | H | 2-CH₃ | 1 | O | O | CH₃ |
| 101 | A1 | 5-Et | H | H | 1 | CH₃ | H | 2-CH₃ | 1 | O | O | CH₃ |
| 102 | A1 | 5-CF₃ | H | H | 1 | CH₃ | H | 2-CH₃ | 1 | O | O | CH₃ |
| 103 | A1 | 5-F | H | H | 1 | CH₃ | H | 2-CH₃ | 1 | O | O | CH₃ |
| 104 | A1 | 5-Cl | H | H | 1 | CH₃ | H | 2-CH₃ | 1 | O | O | CH₃ |

TABLE 2-continued

| | | | | | | | | | | | | |
|---|---|---|---|---|---|---|---|---|---|---|---|---|
| 105 | A1 | 5-OCH₃ | H | H | 1 | CH₃ | H | 2-CH₃ | 1 | O | O | CH₃ |
| 106 | A1 | 5-OEt | H | H | 1 | CH₃ | H | 2-CH₃ | 1 | O | O | CH₃ |
| 107 | A1 | 5-OCF₃ | H | H | 1 | CH₃ | H | 2-CH₃ | 1 | O | O | CH₃ |
| 108 | A1 | 4,5-diCH₃ | H | H | 1 | CH₃ | H | 2-CH₃ | 1 | O | O | CH₃ |
| 109 | A1 | 4-Et-5-CH₃ | H | H | 1 | CH₃ | H | 2-CH₃ | 1 | O | O | CH₃ |
| 110 | A1 | 4-CF₃-5-F | H | H | 1 | CH₃ | H | 2-CH₃ | 1 | O | O | CH₃ |
| 111 | A1 | 4,5-diF | H | H | 1 | CH₃ | H | 2-CH₃ | 1 | O | O | CH₃ |

TABLE 3

| | | | | | | | | | | | | |
|---|---|---|---|---|---|---|---|---|---|---|---|---|
| 112 | A1 | 4-Cl-5-F | H | H | 1 | CH₃ | H | 2-CH₃ | 1 | O | O | CH₃ |
| 113 | A1 | 4,5-diOCH₃ | H | H | 1 | CH₃ | H | 2-CH₃ | 1 | O | O | CH₃ |
| 114 | A1 | 4-OEt-5-CH₃ | H | H | 1 | CH₃ | H | 2-CH₃ | 1 | O | O | CH₃ |
| 115 | A1 | 4-OCF₃-5-F | H | H | 1 | CH₃ | H | 2-CH₃ | 1 | O | O | CH₃ |
| 116 | A1 | 4-CH₃ | H | CH₃ | 1 | CH₃ | H | 2-CH₃ | 1 | O | O | CH₃ |
| 117 | A1 | 4-Et | H | CH₃ | 1 | CH₃ | H | 2-CH₃ | 1 | O | O | CH₃ |
| 118 | A1 | 4-CH₃ | H | Et | 1 | CH₃ | H | 2-CH₃ | 1 | O | O | CH₃ |
| 119 | A1 | 4-CH₃ | H | i-Pr | 1 | CH₃ | H | 2-CH₃ | 1 | O | O | CH₃ |
| 120 | A1 | 4-CH₃ | CH₃ | Et | 1 | CH₃ | H | 2-CH₃ | 1 | O | O | CH₃ |
| 121 | A1 | 4-CH₃ | H | F | 1 | CH₃ | H | 2-CH₃ | 1 | O | O | CH₃ |
| 122 | A1 | 4-CH₃ | F | F | 1 | CH₃ | H | 2-CH₃ | 1 | O | O | CH₃ |
| 123 | A1 | 4-CH₃ | H | CF₃ | 1 | CH₃ | H | 2-CH₃ | 1 | O | O | CH₃ |
| 124 | A1 | 4-CH₃ | H | c-Pr | 1 | CH₃ | H | 2-CH₃ | 1 | O | O | CH₃ |
| 125 | A1 | 4-CH₃ | —CH2CH2— | | 1 | CH₃ | H | 2-CH₃ | 1 | O | O | CH₃ |
| 126 | A1 | 4-CH₃ | —CH2CH2CH2— | | 1 | CH₃ | H | 2-CH₃ | 1 | O | O | CH₃ |
| 127 | A1 | 4-CH₃ | —CH2CH(CH3)— | | 1 | CH₃ | H | 2-CH₃ | 1 | O | O | CH₃ |
| 128 | A1 | 4-CH₃ | —CH2C(CH3)2— | | 1 | CH₃ | H | 2-CH₃ | 1 | O | O | CH₃ |
| 129 | A1 | 4-CH₃ | H | H | 1 | H | H | 2-CH₃ | 1 | O | O | CH₃ |
| 130 | A1 | 4-CH₃ | H | H | 1 | Et | H | 2-CH₃ | 1 | O | O | CH₃ |
| 131 | A1 | 4-CH₃ | H | H | 1 | c-Pr | H | 2-CH₃ | 1 | O | O | CH₃ |
| 132 | A1 | 4-CH₃ | H | H | 1 | CH=CH₂ | H | 2-CH₃ | 1 | O | O | CH₃ |
| 133 | A1 | 4-CH₃ | H | H | 1 | CH₂CH=CH₂ | H | 2-CH₃ | 1 | O | O | CH₃ |
| 134 | A1 | 4-CH₃ | H | H | 1 | ethynyl | H | 2-CH₃ | 1 | O | O | CH₃ |
| 135 | A1 | 4-CH₃ | H | H | 1 | Propargyl | H | 2-CH₃ | 1 | O | O | CH₃ |
| 136 | A1 | 4-CH₃ | H | H | 1 | CF₃ | H | 2-CH₃ | 1 | O | O | CH₃ |
| 137 | A1 | 4-CH₃ | H | H | 1 | CH=CHCl | H | 2-CH₃ | 1 | O | O | CH₃ |
| 138 | A1 | 4-CH₃ | H | H | 1 | 3,3,2-tri-Iodo-allyl | H | 2-CH₃ | 1 | O | O | CH₃ |
| 139 | A1 | 4-CH₃ | H | H | 1 | 3-Iodopropargyl | H | 2-CH₃ | 1 | O | O | CH₃ |
| 140 | A1 | 4-CH₃ | H | H | 1 | CN | H | 2-CH₃ | 1 | O | O | CH₃ |
| 141 | A1 | 4-CF₃ | H | H | 1 | CN | H | 2-CH₃ | 1 | O | O | CH₃ |
| 142 | A1 | 4-CH₃ | H | H | 1 | NO₂ | H | 2-CH₃ | 1 | O | O | CH₃ |
| 143 | A1 | 4-CH₃ | H | H | 1 | NH₂ | H | 2-CH₃ | 1 | O | O | CH₃ |
| 144 | A1 | 4-CH₃ | H | H | 1 | NHOH₃ | H | 2-CH₃ | 1 | O | O | CH₃ |
| 145 | A1 | 4-CH₃ | H | H | 1 | N(CH₃)₂ | H | 2-CH₃ | 1 | O | O | CH₃ |
| 146 | A1 | 4-CH₃ | H | H | 1 | CH₃ | CH₃ | 2-CH₃ | 1 | O | O | CH₃ |
| 147 | A1 | 4-CH₃ | H | H | 1 | CH₃ | Et | 2-CH₃ | 1 | O | O | CH₃ |
| 148 | A1 | 4-CH₃ | H | H | 1 | CH₃ | CH₃CO | 2-CH₃ | 1 | O | O | CH₃ |
| 149 | A1 | 4-CH₃ | H | H | 1 | CH₃ | CH₃CH₂CO | 2-CH₃ | 1 | O | O | CH₃ |
| 150 | A1 | 4-CH₃ | H | H | 1 | CH₃ | PhCO | 2-CH₃ | 1 | O | O | CH₃ |
| 151 | A1 | 4-CH₃ | H | H | 1 | CH₃ | 4-Cl—PhCO | 2-CH₃ | 1 | O | O | CH₃ |
| 152 | A1 | 4-CH₃ | H | H | 1 | CH₃ | PhCH₂CO | 2-CH₃ | 1 | O | O | CH₃ |
| 153 | A1 | 4-CH₃ | H | H | 1 | CH₃ | CHO | 2-CH₃ | 1 | O | O | CH₃ |
| 154 | A1 | 4-CH₃ | H | H | 1 | CH₃ | CH₃OCH₂ | 2-CH₃ | 1 | O | O | CH₃ |
| 155 | A1 | 4-CH₃ | H | H | 1 | CH₃ | CH₃CH(OCH₃) | 2-CH₃ | 1 | O | O | CH₃ |
| 156 | A1 | 4-CH₃ | H | H | 1 | CH₃ | CH₃SO₂ | 2-CH₃ | 1 | O | O | CH₃ |
| 157 | A1 | 4-CH₃ | H | H | 1 | CH₃ | PhSO₂ | 2-CH₃ | 1 | O | O | CH₃ |
| 158 | A1 | 4-CH₃ | H | H | 1 | CH₃ | 4-CH₃—PhSO₂ | 2-CH₃ | 1 | O | O | CH₃ |
| 159 | A1 | 4-CH₃ | H | H | 1 | CH₃ | H | 2-CH₃ | 1 | S | O | CH₃ |
| 160 | A1 | 4-CH₃ | H | H | 1 | CH₃ | H | 2-CH₃ | 1 | O | S | CH₃ |
| 161 | A1 | 4-CH₃ | H | H | 1 | CH₃ | H | 2-CH₃ | 1 | O | — | CH₃ |
| 162 | A1 | 4-CH₃ | H | H | 1 | CH₃ | H | 2-CH₃ | 1 | O | NH | CH₃ |
| 163 | A1 | 4-CH₃ | H | H | 1 | CH₃ | H | 2-CH₃ | 1 | O | NCH₃ | CH₃ |
| 164 | A1 | 4-CH₃ | H | H | 1 | CH₃ | H | 2-CH₃ | 1 | O | O | H |
| 165 | A1 | 4-CH₃ | H | H | 1 | CH₃ | H | 2-CH₃ | 1 | O | O | Et |
| 166 | A1 | 4-CH₃ | H | H | 1 | CH₃ | H | 2-CH₃ | 1 | O | O | n-Pr |
| 167 | A1 | 4-CH₃ | H | H | 1 | CH₃ | H | 2-CH₃ | 1 | O | O | CH₂CH=CH₂ |
| 168 | A1 | 4-CH₃ | H | H | 1 | CH₃ | H | 2-CH₃ | 1 | O | O | CH=CH₂ |
| 169 | A1 | 4-CH₃ | H | H | 1 | CH₃ | H | 2-CH₃ | 1 | O | O | Propargyl |
| 170 | A1 | 4-CH₃ | H | H | 1 | CH₃ | H | 2-CH₃ | 1 | O | O | ethynyl |
| 171 | A1 | 4-CH₃ | H | H | 1 | CH₃ | H | 2-CH₃ | 1 | O | O | CF₃ |
| 172 | A1 | 4-CH₃ | H | H | 1 | CH₃ | H | 2-CH₃ | 1 | O | O | CH₂CF₃ |
| 173 | A1 | 4-CH₃ | H | H | 1 | CH₃ | H | 2-CH₃ | 1 | O | O | CF₂CF₃ |

TABLE 4

| | | | | | | | | | | | |
|---|---|---|---|---|---|---|---|---|---|---|---|
| 174 | A1 | 4-CH₃ | H | H | 1 | CH₃ | H | 2-CH₃ | 1 | O O | CF₂CF₂H |
| 175 | A1 | 4-CH₃ | H | H | 1 | CH₃ | H | 2-CH₃ | 1 | O O | CH₂CH=CHCl |
| 176 | A1 | 4-CH₃ | H | H | 1 | CH₃ | H | 2-CH₃ | 1 | O O | 3-Iodo-propargyl |
| 177 | A1 | 4-CH₃ | H | H | 1 | CH₃ | H | 2-CH₃ | 1 | O O | c-Pr |
| 178 | A1 | 4-CH₃ | H | H | 1 | CH₃ | H | 2-CH₃ | 1 | O O | c-Hex |
| 179 | A1 | 4-CH₃ | H | H | 1 | CH₃ | H | 2-CH₃ | 1 | O O | 2-CH₃-c-Pr |
| 180 | A2 | — | H | H | 1 | CH₃ | H | — | 1 | O O | CH₃ |
| 181 | A2 | — | H | H | 1 | CH₃ | H | 2-Cl | 1 | O O | CH₃ |
| 182 | A2 | 2-CH₃ | H | H | 1 | CH₃ | H | 2-Cl | 1 | O O | CH₃ |
| 183 | A2 | 2-Et | H | H | 1 | CH₃ | H | 2-Cl | 1 | O O | CH₃ |
| 184 | A2 | 2-CF₃ | H | H | 1 | CH₃ | H | 2-Cl | 1 | O O | CH₃ |
| 185 | A2 | 2-F | H | H | 1 | CH₃ | H | 2-Cl | 1 | O O | CH₃ |
| 186 | A2 | 2-Cl | H | H | 1 | CH₃ | H | 2-Cl | 1 | O O | CH₃ |
| 187 | A2 | 2-OCH₃ | H | H | 1 | CH₃ | H | 2-Cl | 1 | O O | CH₃ |
| 188 | A2 | 2-OEt | H | H | 1 | CH₃ | H | 2-Cl | 1 | O O | CH₃ |
| 189 | A2 | 2-OCF₃ | H | H | 1 | CH₃ | H | 2-Cl | 1 | O O | CH₃ |
| 190 | A2 | 5-CH₃ | H | H | 1 | CH₃ | H | 2-Cl | 1 | O O | CH₃ |
| 191 | A2 | 5-Et | H | H | 1 | CH₃ | H | 2-Cl | 1 | O O | CH₃ |
| 192 | A2 | 5-CF₃ | H | H | 1 | CH₃ | H | 2-Cl | 1 | O O | CH₃ |
| 193 | A2 | 5-F | H | H | 1 | CH₃ | H | 2-Cl | 1 | O O | CH₃ |
| 194 | A2 | 5-Cl | H | H | 1 | CH₃ | H | 2-Cl | 1 | O O | CH₃ |
| 195 | A2 | 5-OCH₃ | H | H | 1 | CH₃ | H | 2-Cl | 1 | O O | CH₃ |
| 196 | A2 | 5-OEt | H | H | 1 | CH₃ | H | 2-Cl | 1 | O O | CH₃ |
| 197 | A2 | 5-OCF₃ | H | H | 1 | CH₃ | H | 2-Cl | 1 | O O | CH₃ |
| 198 | A2 | 2,5-diCH₃ | H | H | 1 | CH₃ | H | 2-Cl | 1 | O O | CH₃ |
| 199 | A2 | 2-Et-5-CH₃ | H | H | 1 | CH₃ | H | 2-Cl | 1 | O O | CH₃ |
| 200 | A2 | 2-CF₃-5-F | H | H | 1 | CH₃ | H | 2-Cl | 1 | O O | CH₃ |
| 201 | A2 | 2,5-diF | H | H | 1 | CH₃ | H | 2-Cl | 1 | O O | CH₃ |
| 202 | A2 | 2-Cl-5-F | H | H | 1 | CH₃ | H | 2-Cl | 1 | O O | CH₃ |
| 203 | A2 | 2,5-diOCH₃ | H | H | 1 | CH₃ | H | 2-Cl | 1 | O O | CH₃ |
| 204 | A2 | 2-OEt-5-CH₃ | H | H | 1 | CH₃ | H | 2-Cl | 1 | O O | CH₃ |
| 205 | A2 | 2-OCF₃-5-F | H | H | 1 | CH₃ | H | 2-Cl | 1 | O O | CH₃ |
| 206 | A2 | 2-CH₃ | H | CH₃ | 1 | CH₃ | H | 2-Cl | 1 | O O | CH₃ |
| 207 | A2 | 2-Et | H | CH₃ | 1 | CH₃ | H | 2-Cl | 1 | O O | CH₃ |
| 208 | A2 | 2-CH₃ | H | Et | 1 | CH₃ | H | 2-Cl | 1 | O O | CH₃ |
| 209 | A2 | 2-CH₃ | H | i-Pr | 1 | CH₃ | H | 2-Cl | 1 | O O | CH₃ |
| 210 | A2 | 2-CH₃ | CH₃ | Et | 1 | CH₃ | H | 2-Cl | 1 | O O | CH₃ |
| 211 | A2 | 2-CH₃ | H | F | 1 | CH₃ | H | 2-Cl | 1 | O O | CH₃ |
| 212 | A2 | 2-CH₃ | F | F | 1 | CH₃ | H | 2-Cl | 1 | O O | CH₃ |
| 213 | A2 | 2-CH₃ | H | CF₃ | 1 | CH₃ | H | 2-Cl | 1 | O O | CH₃ |
| 214 | A2 | 2-CH₃ | H | c-Pr | 1 | CH₃ | H | 2-Cl | 1 | O O | CH₃ |
| 215 | A2 | 2-CH₃ | —CH2CH2— | | 1 | CH₃ | H | 2-Cl | 1 | O O | CH₃ |
| 216 | A2 | 2-CH₃ | —CH2CH2CH2— | | 1 | CH₃ | H | 2-Cl | 1 | O O | CH₃ |
| 217 | A2 | 2-CH₃ | —CH2CH(CH3)— | | 1 | CH₃ | H | 2-Cl | 1 | O O | CH₃ |
| 218 | A2 | 2-CH₃ | —CH2C(CH3)2— | | 1 | CH₃ | H | 2-Cl | 1 | O O | CH₃ |
| 219 | A2 | 2-CH₃ | H | H | 1 | H | H | 2-Cl | 1 | O O | CH₃ |
| 220 | A2 | 2-CH₃ | H | H | 1 | Et | H | 2-Cl | 1 | O O | CH₃ |
| 221 | A2 | 2-CH₃ | H | H | 1 | c-Pr | H | 2-Cl | 1 | O O | CH₃ |
| 222 | A2 | 2-CH₃ | H | H | 1 | CH=CH₂ | H | 2-Cl | 1 | O O | CH₃ |
| 223 | A2 | 2-CH₃ | H | H | 1 | CH₂CH=CH₂ | H | 2-Cl | 1 | O O | CH₃ |
| 224 | A2 | 2-CH₃ | H | H | 1 | ethynyl | H | 2-Cl | 1 | O O | CH₃ |
| 225 | A2 | 2-CH₃ | H | H | 1 | Propargyl | H | 2-Cl | 1 | O O | CH₃ |
| 226 | A2 | 2-CH₃ | H | H | 1 | CF₃ | H | 2-Cl | 1 | O O | CH₃ |
| 227 | A2 | 2-CH₃ | H | H | 1 | CH=CHCl | H | 2-Cl | 1 | O O | CH₃ |
| 228 | A2 | 2-CH₃ | H | H | 1 | 3,3,2-tri-Iodo-allyl | H | 2-Cl | 1 | O O | CH₃ |
| 229 | A2 | 2-CH₃ | H | H | 1 | 3-Iodopropargyl | H | 2-Cl | 1 | O O | CH₃ |
| 230 | A2 | 2-CH₃ | H | H | 1 | CN | H | 2-Cl | 1 | O O | CH₃ |
| 231 | A2 | 2-CF₃ | H | H | 1 | CN | H | 2-Cl | 1 | O O | CH₃ |
| 232 | A2 | 2-CH₃ | H | H | 1 | NO₂ | H | 2-Cl | 1 | O O | CH₃ |
| 233 | A2 | 2-CH₃ | H | H | 1 | NH₂ | H | 2-Cl | 1 | O O | CH₃ |
| 234 | A2 | 2-CH₃ | H | H | 1 | NHCH₃ | H | 2-Cl | 1 | O O | CH₃ |
| 235 | A2 | 2-CH₃ | H | H | 1 | N(CH₃)₂ | H | 2-Cl | 1 | O O | CH₃ |

TABLE 5

| | | | | | | | | | | | |
|---|---|---|---|---|---|---|---|---|---|---|---|
| 236 | A2 | 2-CH₃ | H | H | 1 | CH₃ | CH₃ | 2-Cl | 1 | O O | CH₃ |
| 237 | A2 | 2-CH₃ | H | H | 1 | CH₃ | Et | 2-Cl | 1 | O O | CH₃ |
| 238 | A2 | 2-CH₃ | H | H | 1 | CH₃ | CH₃CO | 2-Cl | 1 | O O | CH₃ |
| 239 | A2 | 2-CH₃ | H | H | 1 | CH₃ | CH₃CH₂CO | 2-Cl | 1 | O O | CH₃ |
| 240 | A2 | 2-CH₃ | H | H | 1 | CH₃ | PhCO | 2-Cl | 1 | O O | CH₃ |
| 241 | A2 | 2-CH₃ | H | H | 1 | CH₃ | 4-Cl—PhCO | 2-Cl | 1 | O O | CH₃ |
| 242 | A2 | 2-CH₃ | H | H | 1 | CH₃ | PhCH₂CO | 2-Cl | 1 | O O | CH₃ |
| 243 | A2 | 2-CH₃ | H | H | 1 | CH₃ | CHO | 2-Cl | 1 | O O | CH₃ |
| 244 | A2 | 2-CH₃ | H | H | 1 | CH₃ | CH₃OCH₂ | 2-Cl | 1 | O O | CH₃ |
| 245 | A2 | 2-CH₃ | H | H | 1 | CH₃ | CH₃CH(OCH₃) | 2-Cl | 1 | O O | CH₃ |
| 246 | A2 | 2-CH₃ | H | H | 1 | CH₃ | CH₃SO₂ | 2-Cl | 1 | O O | CH₃ |
| 247 | A2 | 2-CH₃ | H | H | 1 | CH₃ | PhSO₂ | 2-Cl | 1 | O O | CH₃ |

TABLE 5-continued

| | | | | | | | | | | | | |
|---|---|---|---|---|---|---|---|---|---|---|---|---|
| 248 | A2 | 2-CH$_3$ | H | H | 1 | CH$_3$ | 4-CH$_3$—PhSO$_2$ | 2-Cl | 1 | O | O | CH$_3$ |
| 249 | A2 | 2-CH$_3$ | H | H | 1 | CH$_3$ | H | 2-Cl | 1 | S | O | CH$_3$ |
| 250 | A2 | 2-CH$_3$ | H | H | 1 | CH$_3$ | H | 2-Cl | 1 | O | S | CH$_3$ |
| 251 | A2 | 2-CH$_3$ | H | H | 1 | CH$_3$ | H | 2-Cl | 1 | O | — | CH$_3$ |
| 252 | A2 | 2-CH$_3$ | H | H | 1 | CH$_3$ | H | 2-Cl | 1 | O | NH | CH$_3$ |
| 253 | A2 | 2-CH$_3$ | H | H | 1 | CH$_3$ | H | 2-Cl | 1 | O | NCH$_3$ | CH$_3$ |
| 254 | A2 | 2-CH$_3$ | H | H | 1 | CH$_3$ | H | 2-Cl | 1 | O | O | H |
| 255 | A2 | 2-CH$_3$ | H | H | 1 | CH$_3$ | H | 2-Cl | 1 | O | O | Et |
| 256 | A2 | 2-CH$_3$ | H | H | 1 | CH$_3$ | H | 2-Cl | 1 | O | O | n-Pr |
| 257 | A2 | 2-CH$_3$ | H | H | 1 | CH$_3$ | H | 2-Cl | 1 | O | O | CH$_2$CH=CH$_2$ |
| 258 | A2 | 2-CH$_3$ | H | H | 1 | CH$_3$ | H | 2-Cl | 1 | O | O | CH=CH$_2$ |
| 259 | A2 | 2-CH$_3$ | H | H | 1 | CH$_3$ | H | 2-Cl | 1 | O | O | Propargyl |
| 260 | A2 | 2-CH$_3$ | H | H | 1 | CH$_3$ | H | 2-Cl | 1 | O | O | ethynyl |
| 261 | A2 | 2-CH$_3$ | H | H | 1 | CH$_3$ | H | 2-Cl | 1 | O | O | CF$_3$ |
| 262 | A2 | 2-CH$_3$ | H | H | 1 | CH$_3$ | H | 2-Cl | 1 | O | O | CH$_2$CF$_3$ |
| 263 | A2 | 2-CH$_3$ | H | H | 1 | CH$_3$ | H | 2-Cl | 1 | O | O | CF$_2$CF$_3$ |
| 264 | A2 | 2-CH$_3$ | H | H | 1 | CH$_3$ | H | 2-Cl | 1 | O | O | CF$_2$CF$_2$H |
| 265 | A2 | 2-CH$_3$ | H | H | 1 | CH$_3$ | H | 2-Cl | 1 | O | O | CH$_2$CH=CHCl |
| 266 | A2 | 2-CH$_3$ | H | H | 1 | CH$_3$ | H | 2-Cl | 1 | O | O | 3-Iodo-propargyl |
| 267 | A2 | 2-CH$_3$ | H | H | 1 | CH$_3$ | H | 2-Cl | 1 | O | O | c-Pr |
| 268 | A2 | 2-CH$_3$ | H | H | 1 | CH$_3$ | H | 2-Cl | 1 | O | O | c-Hex |
| 269 | A2 | 2-CH$_3$ | H | H | 1 | CH$_3$ | H | 2-Cl | 1 | O | O | 2-CH$_3$-c-Pr |
| 270 | A2 | — | H | H | 1 | CH$_3$ | H | 2-CH$_3$ | 1 | O | O | CH$_3$ |
| 271 | A2 | 2-CH$_3$ | H | H | 1 | CH$_3$ | H | 2-CH$_3$ | 1 | O | O | CH$_3$ |
| 272 | A2 | 2-Et | H | H | 1 | CH$_3$ | H | 2-CH$_3$ | 1 | O | O | CH$_3$ |
| 273 | A2 | 2-CF$_3$ | H | H | 1 | CH$_3$ | H | 2-CH$_3$ | 1 | O | O | CH$_3$ |
| 274 | A2 | 2-F | H | H | 1 | CH$_3$ | H | 2-CH$_3$ | 1 | O | O | CH$_3$ |
| 275 | A2 | 2-Cl | H | H | 1 | CH$_3$ | H | 2-CH$_3$ | 1 | O | O | CH$_3$ |
| 276 | A2 | 2-OCH$_3$ | H | H | 1 | CH$_3$ | H | 2-CH$_3$ | 1 | O | O | CH$_3$ |
| 277 | A2 | 2-OEt | H | H | 1 | CH$_3$ | H | 2-CH$_3$ | 1 | O | O | CH$_3$ |
| 278 | A2 | 2-OCF$_3$ | H | H | 1 | CH$_3$ | H | 2-CH$_3$ | 1 | O | O | CH$_3$ |
| 279 | A2 | 5-CH$_3$ | H | H | 1 | CH$_3$ | H | 2-CH$_3$ | 1 | O | O | CH$_3$ |
| 280 | A2 | 5-Et | H | H | 1 | CH$_3$ | H | 2-CH$_3$ | 1 | O | O | CH$_3$ |
| 281 | A2 | 5-CF$_3$ | H | H | 1 | CH$_3$ | H | 2-CH$_3$ | 1 | O | O | CH$_3$ |
| 282 | A2 | 5-F | H | H | 1 | CH$_3$ | H | 2-CH$_3$ | 1 | O | O | CH$_3$ |
| 283 | A2 | 5-Cl | H | H | 1 | CH$_3$ | H | 2-CH$_3$ | 1 | O | O | CH$_3$ |
| 284 | A2 | 5-OCH$_3$ | H | H | 1 | CH$_3$ | H | 2-CH$_3$ | 1 | O | O | CH$_3$ |
| 285 | A2 | 5-OEt | H | H | 1 | CH$_3$ | H | 2-CH$_3$ | 1 | O | O | CH$_3$ |
| 286 | A2 | 5-OCF$_3$ | H | H | 1 | CH$_3$ | H | 2-CH$_3$ | 1 | O | O | CH$_3$ |
| 287 | A2 | 2,5-diCH$_3$ | H | H | 1 | CH$_3$ | H | 2-CH$_3$ | 1 | O | O | CH$_3$ |
| 288 | A2 | 2-Et-5-CH$_3$ | H | H | 1 | CH$_3$ | H | 2-CH$_3$ | 1 | O | O | CH$_3$ |
| 289 | A2 | 2-CF$_3$5-F | H | H | 1 | CH$_3$ | H | 2-CH$_3$ | 1 | O | O | CH$_3$ |
| 290 | A2 | 2,5-diF | H | H | 1 | CH$_3$ | H | 2-CH$_3$ | 1 | O | O | CH$_3$ |
| 291 | A2 | 2-Cl-5-F | H | H | 1 | CH$_3$ | H | 2-CH$_3$ | 1 | O | O | CH$_3$ |
| 292 | A2 | 2,5-diOCH$_3$ | H | H | 1 | CH$_3$ | H | 2-CH$_3$ | 1 | O | O | CH$_3$ |
| 293 | A2 | 2-OEt-5-CH$_3$ | H | H | 1 | CH$_3$ | H | 2-CH$_3$ | 1 | O | O | CH$_3$ |
| 294 | A2 | 2-OCF$_3$-5-F | H | H | 1 | CH$_3$ | H | 2-CH$_3$ | 1 | O | O | CH$_3$ |
| 295 | A2 | 2-CH$_3$ | H | CH$_3$ | 1 | CH$_3$ | H | 2-CH$_3$ | 1 | O | O | CH$_3$ |
| 296 | A2 | 2-Et | H | CH$_3$ | 1 | CH$_3$ | H | 2-CH$_3$ | 1 | O | O | CH$_3$ |
| 297 | A2 | 2-CH$_3$ | H | Et | 1 | CH$_3$ | H | 2-CH$_3$ | 1 | O | O | CH$_3$ |

TABLE 6

| | | | | | | | | | | | | |
|---|---|---|---|---|---|---|---|---|---|---|---|---|
| 298 | A2 | 2-CH$_3$ | H | i-Pr | 1 | CH$_3$ | H | 2-CH$_3$ | 1 | O | O | CH$_3$ |
| 299 | A2 | 2-CH$_3$ | CH$_3$ | Et | 1 | CH$_3$ | H | 2-CH$_3$ | 1 | O | O | CH$_3$ |
| 300 | A2 | 2-CH$_3$ | H | F | 1 | CH$_3$ | H | 2-CH$_3$ | 1 | O | O | CH$_3$ |
| 301 | A2 | 2-CH$_3$ | F | F | 1 | CH$_3$ | H | 2-CH$_3$ | 1 | O | O | CH$_3$ |
| 302 | A2 | 2-CH$_3$ | H | CF$_3$ | 1 | CH$_3$ | H | 2-CH$_3$ | 1 | O | O | CH$_3$ |
| 303 | A2 | 2-CH$_3$ | H | c-Pr | 1 | CH$_3$ | H | 2-CH$_3$ | 1 | O | O | CH$_3$ |
| 304 | A2 | 2-CH$_3$ | —CH2CH2— | | 1 | CH$_3$ | H | 2-CH$_3$ | 1 | O | O | CH$_3$ |
| 305 | A2 | 2-CH$_3$ | —CH2CH2CH2— | | 1 | CH$_3$ | H | 2-CH$_3$ | 1 | O | O | CH$_3$ |
| 306 | A2 | 2-CH$_3$ | —CH2CH(CH3)— | | 1 | CH$_3$ | H | 2-CH$_3$ | 1 | O | O | CH$_3$ |
| 307 | A2 | 2-CH$_3$ | —CH2C(CH3)2— | | 1 | CH$_3$ | H | 2-CH$_3$ | 1 | O | O | CH$_3$ |
| 308 | A2 | 2-CH$_3$ | H | H | 1 | H | H | 2-CH$_3$ | 1 | O | O | CH$_3$ |
| 309 | A2 | 2-CH$_3$ | H | H | 1 | Et | H | 2-CH$_3$ | 1 | O | O | CH$_3$ |
| 310 | A2 | 2-CH$_3$ | H | H | 1 | c-Pr | H | 2-CH$_3$ | 1 | O | O | CH$_3$ |
| 311 | A2 | 2-CH$_3$ | H | H | 1 | CH=CH$_2$ | H | 2-CH$_3$ | 1 | O | O | CH$_3$ |
| 312 | A2 | 2-CH$_3$ | H | H | 1 | CH$_2$CH=CH$_2$ | H | 2-CH$_3$ | 1 | O | O | CH$_3$ |
| 313 | A2 | 2-CH$_3$ | H | H | 1 | ethynyl | H | 2-CH$_3$ | 1 | O | O | CH$_3$ |
| 314 | A2 | 2-CH$_3$ | H | H | 1 | Propargyl | H | 2-CH$_3$ | 1 | O | O | CH$_3$ |
| 315 | A2 | 2-CH$_3$ | H | H | 1 | CF$_3$ | H | 2-CH$_3$ | 1 | O | O | CH$_3$ |
| 316 | A2 | 2-CH$_3$ | H | H | 1 | CH=CHCl | H | 2-CH$_3$ | 1 | O | O | CH$_3$ |
| 317 | A2 | 2-CH$_3$ | H | H | 1 | 3,3,2-tri-Iodo-allyl | H | 2-CH$_3$ | 1 | O | O | CH$_3$ |
| 318 | A2 | 2-CH$_3$ | H | H | 1 | 3-Iodopropargyl | H | 2-CH$_3$ | 1 | O | O | CH$_3$ |
| 319 | A2 | 2-CH$_3$ | H | H | 1 | CN | H | 2-CH$_3$ | 1 | O | O | CH$_3$ |
| 320 | A2 | 2-CF$_3$ | H | H | 1 | CN | H | 2-CH$_3$ | 1 | O | O | CH$_3$ |
| 321 | A2 | 2-CH$_3$ | H | H | 1 | NO$_2$ | H | 2-CH$_3$ | 1 | O | O | CH$_3$ |

TABLE 6-continued

| | | | | | | | | | | | | |
|---|---|---|---|---|---|---|---|---|---|---|---|---|
| 322 | A2 | 2-CH$_3$ | H | H | 1 | NH$_2$ | H | 2-CH$_3$ | 1 | O | O | CH$_3$ |
| 323 | A2 | 2-CH$_3$ | H | H | 1 | NHCH$_3$ | H | 2-CH$_3$ | 1 | O | O | CH$_3$ |
| 324 | A2 | 2-CH$_3$ | H | H | 1 | N(CH$_3$)$_2$ | H | 2-CH$_3$ | 1 | O | O | CH$_3$ |
| 325 | A2 | 2-CH$_3$ | H | H | 1 | CH$_3$ | CH$_3$ | 2-CH$_3$ | 1 | O | O | CH$_3$ |
| 326 | A2 | 2-CH$_3$ | H | H | 1 | CH$_3$ | Et | 2-CH$_3$ | 1 | O | O | CH$_3$ |
| 327 | A2 | 2-CH$_3$ | H | H | 1 | CH$_3$ | CH$_3$CO | 2-CH$_3$ | 1 | O | O | CH$_3$ |
| 328 | A2 | 2-CH$_3$ | H | H | 1 | CH$_3$ | CH$_3$CH$_2$CO | 2-CH$_3$ | 1 | O | O | CH$_3$ |
| 329 | A2 | 2-CH$_3$ | H | H | 1 | CH$_3$ | PhCO | 2-CH$_3$ | 1 | O | O | CH$_3$ |
| 330 | A2 | 2-CH$_3$ | H | H | 1 | CH$_3$ | 4-Cl-PhCO | 2-CH$_3$ | 1 | O | O | CH$_3$ |
| 331 | A2 | 2-CH$_3$ | H | H | 1 | CH$_3$ | PhCH$_2$CO | 2-CH$_3$ | 1 | O | O | CH$_3$ |
| 332 | A2 | 2-CH$_3$ | H | H | 1 | CH$_3$ | CHO | 2-CH$_3$ | 1 | O | O | CH$_3$ |
| 333 | A2 | 2-CH$_3$ | H | H | 1 | CH$_3$ | CH$_3$OCH$_2$ | 2-CH$_3$ | 1 | O | O | CH$_3$ |
| 334 | A2 | 2-CH$_3$ | H | H | 1 | CH$_3$ | CH$_3$CH(OCH$_3$) | 2-CH$_3$ | 1 | O | O | CH$_3$ |
| 335 | A2 | 2-CH$_3$ | H | H | 1 | CH$_3$ | CH$_3$SO$_2$ | 2-CH$_3$ | 1 | O | O | CH$_3$ |
| 336 | A2 | 2-CH$_3$ | H | H | 1 | CH$_3$ | PhSO$_2$ | 2-CH$_3$ | 1 | O | O | CH$_3$ |
| 337 | A2 | 2-CH$_3$ | H | H | 1 | CH$_3$ | 4-CH$_3$—PhSO$_2$ | 2-CH$_3$ | 1 | O | O | CH$_3$ |
| 338 | A2 | 2-CH$_3$ | H | H | 1 | CH$_3$ | H | 2-CH$_3$ | 1 | S | O | CH$_3$ |
| 339 | A2 | 2-CH$_3$ | H | H | 1 | CH$_3$ | H | 2-CH$_3$ | 1 | O | S | CH$_3$ |
| 340 | A2 | 2-CH$_3$ | H | H | 1 | CH$_3$ | H | 2-CH$_3$ | 1 | O | — | CH$_3$ |
| 341 | A2 | 2-CH$_3$ | H | H | 1 | CH$_3$ | H | 2-CH$_3$ | 1 | O | NH | CH$_3$ |
| 342 | A2 | 2-CH$_3$ | H | H | 1 | CH$_3$ | H | 2-CH$_3$ | 1 | O | NCH$_3$ | CH$_3$ |
| 343 | A2 | 2-CH$_3$ | H | H | 1 | CH$_3$ | H | 2-CH$_3$ | 1 | O | O | H |
| 344 | A2 | 2-CH$_3$ | H | H | 1 | CH$_3$ | H | 2-CH$_3$ | 1 | O | O | Et |
| 345 | A2 | 2-CH$_3$ | H | H | 1 | CH$_3$ | H | 2-CH$_3$ | 1 | O | O | n-Pr |
| 346 | A2 | 2-CH$_3$ | H | H | 1 | CH$_3$ | H | 2-CH$_3$ | 1 | O | O | CH$_2$CH=CH$_2$ |
| 347 | A2 | 2-CH$_3$ | H | H | 1 | CH$_3$ | H | 2-CH$_3$ | 1 | O | O | CH=CH$_2$ |
| 348 | A2 | 2-CH$_3$ | H | H | 1 | CH$_3$ | H | 2-CH$_3$ | 1 | O | O | Propargyl |
| 349 | A2 | 2-CH$_3$ | H | H | 1 | CH$_3$ | H | 2-CH$_3$ | 1 | O | O | ethynyl |
| 350 | A2 | 2-CH$_3$ | H | H | 1 | CH$_3$ | H | 2-CH$_3$ | 1 | O | O | CF$_3$ |
| 351 | A2 | 2-CH$_3$ | H | H | 1 | CH$_3$ | H | 2-CH$_3$ | 1 | O | O | CH$_2$CF$_3$ |
| 352 | A2 | 2-CH$_3$ | H | H | 1 | CH$_3$ | H | 2-CH$_3$ | 1 | O | O | CF$_2$CF$_3$ |
| 353 | A2 | 2-CH$_3$ | H | H | 1 | CH$_3$ | H | 2-CH$_3$ | 1 | O | O | CF$_2$CF$_2$H |
| 354 | A2 | 2-CH$_3$ | H | H | 1 | CH$_3$ | H | 2-CH$_3$ | 1 | O | O | CH$_2$CH=CHCl |
| 355 | A2 | 2-CH$_3$ | H | H | 1 | CH$_3$ | H | 2-CH$_3$ | 1 | O | O | 3-Iodo-propargyl |
| 356 | A2 | 2-CH$_3$ | H | H | 1 | CH$_3$ | H | 2-CH$_3$ | 1 | O | O | c-Pr |
| 357 | A2 | 2-CH$_3$ | H | H | 1 | CH$_3$ | H | 2-CH$_3$ | 1 | O | O | c-Hex |
| 358 | A2 | 2-CH$_3$ | H | H | 1 | CH$_3$ | H | 2-CH$_3$ | 1 | O | O | 2-CH$_3$-c-Pr |
| 359 | B1 | — | H | H | 1 | CH$_3$ | H | — | 0 | O | O | CH$_3$ |

TABLE 7

| | | | | | | | | | | | | |
|---|---|---|---|---|---|---|---|---|---|---|---|---|
| 360 | B1 | — | H | H | 1 | CH$_3$ | H | 2-Cl | 1 | O | O | CH$_3$ |
| 361 | B1 | 4-CH$_3$ | H | H | 1 | CH$_3$ | H | 2-Cl | 1 | O | O | CH$_3$ |
| 362 | B1 | 4-Et | H | H | 1 | CH$_3$ | H | 2-Cl | 1 | O | O | CH$_3$ |
| 363 | B1 | 4-CF$_3$ | H | H | 1 | CH$_3$ | H | 2-Cl | 1 | O | O | CH$_3$ |
| 364 | B1 | 4-F | H | H | 1 | CH$_3$ | H | 2-Cl | 1 | O | O | CH$_3$ |
| 365 | B1 | 4-Cl | H | H | 1 | CH$_3$ | H | 2-Cl | 1 | O | O | CH$_3$ |
| 366 | B1 | 4-OCH$_3$ | H | H | 1 | CH$_3$ | H | 2-Cl | 1 | O | O | CH$_3$ |
| 367 | B1 | 4-OEt | H | H | 1 | CH$_3$ | H | 2-Cl | 1 | O | O | CH$_3$ |
| 368 | B1 | 4-OCF$_3$ | H | H | 1 | CH$_3$ | H | 2-Cl | 1 | O | O | CH$_3$ |
| 369 | B1 | 5-CH$_3$ | H | H | 1 | CH$_3$ | H | 2-Cl | 1 | O | O | CH$_3$ |
| 370 | B1 | 5-Et | H | H | 1 | CH$_3$ | H | 2-Cl | 1 | O | O | CH$_3$ |
| 371 | B1 | 5-CF$_3$ | H | H | 1 | CH$_3$ | H | 2-Cl | 1 | O | O | CH$_3$ |
| 372 | B1 | 5-F | H | H | 1 | CH$_3$ | H | 2-Cl | 1 | O | O | CH$_3$ |
| 373 | B1 | 5-Cl | H | H | 1 | CH$_3$ | H | 2-Cl | 1 | O | O | CH$_3$ |
| 374 | B1 | 5-OCH$_3$ | H | H | 1 | CH$_3$ | H | 2-Cl | 1 | O | O | CH$_3$ |
| 375 | B1 | 5-OEt | H | H | 1 | CH$_3$ | H | 2-Cl | 1 | O | O | CH$_3$ |
| 376 | B1 | 5-OCF$_3$ | H | H | 1 | CH$_3$ | H | 2-Cl | 1 | O | O | CH$_3$ |
| 377 | B1 | 4,5-diCH$_3$ | H | H | 1 | CH$_3$ | H | 2-Cl | 1 | O | O | CH$_3$ |
| 378 | B1 | 4-Et-5-CH$_3$ | H | H | 1 | CH$_3$ | H | 2-Cl | 1 | O | O | CH$_3$ |
| 379 | B1 | 4-CF$_3$-5-F | H | H | 1 | CH$_3$ | H | 2-Cl | 1 | O | O | CH$_3$ |
| 380 | B1 | 4,5-diF | H | H | 1 | CH$_3$ | H | 2-Cl | 1 | O | O | CH$_3$ |
| 381 | B1 | 4-Cl-5-F | H | H | 1 | CH$_3$ | H | 2-Cl | 1 | O | O | CH$_3$ |
| 382 | B1 | 4,5-diOCH$_3$ | H | H | 1 | CH$_3$ | H | 2-Cl | 1 | O | O | CH$_3$ |
| 383 | B1 | 4-OEt-5-CH$_3$ | H | H | 1 | CH$_3$ | H | 2-Cl | 1 | O | O | CH$_3$ |
| 384 | B1 | 4-OCF$_3$-5-F | H | H | 1 | CH$_3$ | H | 2-Cl | 1 | O | O | CH$_3$ |
| 385 | B1 | 4-CH$_3$ | H | CH$_3$ | 1 | CH$_3$ | H | 2-Cl | 1 | O | O | CH$_3$ |
| 386 | B1 | 4-Et | H | CH$_3$ | 1 | CH$_3$ | H | 2-Cl | 1 | O | O | CH$_3$ |
| 387 | B1 | 4-CH$_3$ | H | Et | 1 | CH$_3$ | H | 2-Cl | 1 | O | O | CH$_3$ |
| 388 | B1 | 4-CH$_3$ | H | i-Pr | 1 | CH$_3$ | H | 2-Cl | 1 | O | O | CH$_3$ |
| 389 | B1 | 4-CH$_3$ | CH$_3$ | Et | 1 | CH$_3$ | H | 2-Cl | 1 | O | O | CH$_3$ |
| 390 | B1 | 4-CH$_3$ | H | F | 1 | CH$_3$ | H | 2-Cl | 1 | O | O | CH$_3$ |
| 391 | B1 | 4-CH$_3$ | F | F | 1 | CH$_3$ | H | 2-Cl | 1 | O | O | CH$_3$ |
| 392 | B1 | 4-CH$_3$ | H | CF$_3$ | 1 | CH$_3$ | H | 2-Cl | 1 | O | O | CH$_3$ |
| 393 | B1 | 4-CH$_3$ | H | c-Pr | 1 | CH$_3$ | H | 2-Cl | 1 | O | O | CH$_3$ |
| 394 | B1 | 4-CH$_3$ | —CH2CH2— | | 1 | CH$_3$ | H | 2-Cl | 1 | O | O | CH$_3$ |
| 395 | B1 | 4-CH$_3$ | —CH2CH2CH2— | | 1 | CH$_3$ | H | 2-Cl | 1 | O | O | CH$_3$ |

TABLE 7-continued

| | | | | | | | | | | | | |
|---|---|---|---|---|---|---|---|---|---|---|---|---|
| 396 | B1 | 4-CH$_3$ | —CH2CH(CH3)— | | 1 | CH$_3$ | H | 2-Cl | 1 | O | O | CH$_3$ |
| 397 | B1 | 4-CH$_3$ | —CH2C(CH3)2— | | 1 | CH$_3$ | H | 2-Cl | 1 | O | O | CH$_3$ |
| 398 | B1 | 4-CH$_3$ | H | H | 1 | H | H | 2-Cl | 1 | O | O | CH$_3$ |
| 399 | B1 | 4-CH$_3$ | H | H | 1 | Et | H | 2-Cl | 1 | O | O | CH$_3$ |
| 400 | B1 | 4-CH$_3$ | H | H | 1 | c-Pr | H | 2-Cl | 1 | O | O | CH$_3$ |
| 401 | B1 | 4-CH$_3$ | H | H | 1 | CH=CH$_2$ | H | 2-Cl | 1 | O | O | CH$_3$ |
| 402 | B1 | 4-CH$_3$ | H | H | 1 | CH$_2$CH=CH$_2$ | H | 2-Cl | 1 | O | O | CH$_3$ |
| 403 | B1 | 4-CH$_3$ | H | H | 1 | ethynyl | H | 2-Cl | 1 | O | O | CH$_3$ |
| 404 | B1 | 4-CH$_3$ | H | H | 1 | Propargyl | H | 2-Cl | 1 | O | O | CH$_3$ |
| 405 | B1 | 4-CH$_3$ | H | H | 1 | CF$_3$ | H | 2-Cl | 1 | O | O | CH$_3$ |
| 406 | B1 | 4-CH$_3$ | H | H | 1 | CH=CHCl | H | 2-Cl | 1 | O | O | CH$_3$ |
| 407 | B1 | 4-CH$_3$ | H | H | 1 | 3,3,2-tri-Iodo-allyl | H | 2-Cl | 1 | O | O | CH$_3$ |
| 408 | B1 | 4-CH$_3$ | H | H | 1 | 3-Iodopropargyl | H | 2-Cl | 1 | O | O | CH$_3$ |
| 409 | B1 | 4-CH$_3$ | H | H | 1 | CN | H | 2-Cl | 1 | O | O | CH$_3$ |
| 410 | B1 | 4-CF3 | H | H | 1 | CN | H | 2-Cl | 1 | O | O | CH$_3$ |
| 411 | B1 | 4-CH$_3$ | H | H | 1 | NO$_2$ | H | 2-Cl | 1 | O | O | CH$_3$ |
| 412 | B1 | 4-CH$_3$ | H | H | 1 | NH$_2$ | H | 2-Cl | 1 | O | O | CH$_3$ |
| 413 | B1 | 4-CH$_3$ | H | H | 1 | NHCH$_3$ | H | 2-Cl | 1 | O | O | CH$_3$ |
| 414 | B1 | 4-CH$_3$ | H | H | 1 | N(CH$_3$)$_2$ | H | 2-Cl | 1 | O | O | CH$_3$ |
| 415 | B1 | 4-CH$_3$ | H | H | 1 | CH$_3$ | CH$_3$ | 2-Cl | 1 | O | O | CH$_3$ |
| 416 | B1 | 4-CH$_3$ | H | H | 1 | CH$_3$ | Et | 2-Cl | 1 | O | O | CH$_3$ |
| 417 | B1 | 4-CH$_3$ | H | H | 1 | CH$_3$ | CH$_3$CO | 2-Cl | 1 | O | O | CH$_3$ |
| 418 | B1 | 4-CH$_3$ | H | H | 1 | CH$_3$ | CH$_3$CH$_2$CO | 2-Cl | 1 | O | O | CH$_3$ |
| 419 | B1 | 4-CH$_3$ | H | H | 1 | CH$_3$ | PhCO | 2-Cl | 1 | O | O | CH$_3$ |

TABLE 8

| | | | | | | | | | | | | |
|---|---|---|---|---|---|---|---|---|---|---|---|---|
| 420 | B1 | 4-CH$_3$ | H | H | 1 | CH$_3$ | 4-Cl-PhCO | 2-Cl | 1 | O | O | CH$_3$ |
| 421 | B1 | 4-CH$_3$ | H | H | 1 | CH$_3$ | PhCH$_2$CO | 2-Cl | 1 | O | O | CH$_3$ |
| 422 | B1 | 4-CH$_3$ | H | H | 1 | CH$_3$ | CHO | 2-Cl | 1 | O | O | CH$_3$ |
| 423 | B1 | 4-CH$_3$ | H | H | 1 | CH$_3$ | CH$_3$OCH$_2$ | 2-Cl | 1 | O | O | CH$_3$ |
| 424 | B1 | 4-CH$_3$ | H | H | 1 | CH$_3$ | CH$_3$CH(OCH$_3$) | 2-Cl | 1 | O | O | CH$_3$ |
| 425 | B1 | 4-CH$_3$ | H | H | 1 | CH$_3$ | CH$_3$SO$_2$ | 2-Cl | 1 | O | O | CH$_3$ |
| 426 | B1 | 4-CH$_3$ | H | H | 1 | CH$_3$ | PhSO$_2$ | 2-Cl | 1 | O | O | CH$_3$ |
| 427 | B1 | 4-CH$_3$ | H | H | 1 | CH$_3$ | 4-CH$_3$-PhSO$_2$ | 2-Cl | 1 | O | O | CH$_3$ |
| 428 | B1 | 4-CH$_3$ | H | H | 1 | CH$_3$ | H | 2-Cl | 1 | S | O | CH$_3$ |
| 429 | B1 | 4-CH$_3$ | H | H | 1 | CH$_3$ | H | 2-Cl | 1 | O | S | CH$_3$ |
| 430 | B1 | 4-CH$_3$ | H | H | 1 | CH$_3$ | H | 2-Cl | 1 | O | — | CH$_3$ |
| 431 | B1 | 4-CH$_3$ | H | H | 1 | CH$_3$ | H | 2-Cl | 1 | O | NH | CH$_3$ |
| 432 | B1 | 4-CH$_3$ | H | H | 1 | CH$_3$ | H | 2-Cl | 1 | O | NCH$_3$ | CH$_3$ |
| 433 | B1 | 4-CH$_3$ | H | H | 1 | CH$_3$ | H | 2-Cl | 1 | O | O | H |
| 434 | B1 | 4-CH$_3$ | H | H | 1 | CH$_3$ | H | 2-Cl | 1 | O | O | Et |
| 435 | B1 | 4-CH$_3$ | H | H | 1 | CH$_3$ | H | 2-Cl | 1 | O | O | n-Pr |
| 436 | B1 | 4-CH$_3$ | H | H | 1 | CH$_3$ | H | 2-Cl | 1 | O | O | CH$_2$CH=CH$_2$ |
| 437 | B1 | 4-CH$_3$ | H | H | 1 | CH$_3$ | H | 2-Cl | 1 | O | O | CH=CH$_2$ |
| 438 | B1 | 4-CH$_3$ | H | H | 1 | CH$_3$ | H | 2-Cl | 1 | O | O | Propargyl |
| 439 | B1 | 4-CH$_3$ | H | H | 1 | CH$_3$ | H | 2-Cl | 1 | O | O | ethynyl |
| 440 | B1 | 4-CH$_3$ | H | H | 1 | CH$_3$ | H | 2-Cl | 1 | O | O | CF$_3$ |
| 441 | B1 | 4-CH$_3$ | H | H | 1 | CH$_3$ | H | 2-Cl | 1 | O | O | CH$_2$CF$_3$ |
| 442 | B1 | 4-CH$_3$ | H | H | 1 | CH$_3$ | H | 2-Cl | 1 | O | O | CF$_2$CF$_3$ |
| 443 | B1 | 4-CH$_3$ | H | H | 1 | CH$_3$ | H | 2-Cl | 1 | O | O | CF$_2$CF$_2$H |
| 444 | B1 | 4-CH$_3$ | H | H | 1 | CH$_3$ | H | 2-Cl | 1 | O | O | CH$_2$CH=CHCl |
| 445 | B1 | 4-CH$_3$ | H | H | 1 | CH$_3$ | H | 2-Cl | 1 | O | O | 3-Iodo-propargyl |
| 446 | B1 | 4-CH$_3$ | H | H | 1 | CH$_3$ | H | 2-Cl | 1 | O | O | c-Pr |
| 447 | B1 | 4-CH$_3$ | H | H | 1 | CH$_3$ | H | 2-Cl | 1 | O | O | c-Hex |
| 448 | B1 | 4-CH$_3$ | H | H | 1 | CH$_3$ | H | 2-Cl | 1 | O | O | 2-CH$_3$-c-Pr |
| 449 | B1 | — | H | H | 1 | CH$_3$ | H | 2-CH$_3$ | 1 | O | O | CH$_3$ |
| 450 | B1 | 4-CH$_3$ | H | H | 1 | CH$_3$ | H | 2-CH$_3$ | 1 | O | O | CH$_3$ |
| 451 | B1 | 4-Et | H | H | 1 | CH$_3$ | H | 2-CH$_3$ | 1 | O | O | CH$_3$ |
| 452 | B1 | 4-CF$_3$ | H | H | 1 | CH$_3$ | H | 2-CH$_3$ | 1 | O | O | CH$_3$ |
| 453 | B1 | 4-F | H | H | 1 | CH$_3$ | H | 2-CH$_3$ | 1 | O | O | CH$_3$ |
| 454 | B1 | 4-Cl | H | H | 1 | CH$_3$ | H | 2-CH$_3$ | 1 | O | O | CH$_3$ |
| 455 | B1 | 4-OCH$_3$ | H | H | 1 | CH$_3$ | H | 2-CH$_3$ | 1 | O | O | CH$_3$ |
| 456 | B1 | 4-OEt | H | H | 1 | CH$_3$ | H | 2-CH$_3$ | 1 | O | O | CH$_3$ |
| 457 | B1 | 4-OCF$_3$ | H | H | 1 | CH$_3$ | H | 2-CH$_3$ | 1 | O | O | CH$_3$ |
| 458 | B1 | 5-CH$_3$ | H | H | 1 | CH$_3$ | H | 2-CH$_3$ | 1 | O | O | CH$_3$ |
| 459 | B1 | 5-Et | H | H | 1 | CH$_3$ | H | 2-CH$_3$ | 1 | O | O | CH$_3$ |
| 460 | B1 | 5-CF$_3$ | H | H | 1 | CH$_3$ | H | 2-CH$_3$ | 1 | O | O | CH$_3$ |
| 461 | B1 | 5-F | H | H | 1 | CH$_3$ | H | 2-CH$_3$ | 1 | O | O | CH$_3$ |
| 462 | B1 | 5-Cl | H | H | 1 | CH$_3$ | H | 2-CH$_3$ | 1 | O | O | CH$_3$ |
| 463 | B1 | 5-OCH$_3$ | H | H | 1 | CH$_3$ | H | 2-CH$_3$ | 1 | O | O | CH$_3$ |
| 464 | B1 | 5-OEt | H | H | 1 | CH$_3$ | H | 2-CH$_3$ | 1 | O | O | CH$_3$ |
| 465 | B1 | 5-OCF$_3$ | H | H | 1 | CH$_3$ | H | 2-CH$_3$ | 1 | O | O | CH$_3$ |
| 466 | B1 | 4,5-diCH$_3$ | H | H | 1 | CH$_3$ | H | 2-CH$_3$ | 1 | O | O | CH$_3$ |
| 467 | B1 | 4-Et-5-CH$_3$ | H | H | 1 | CH$_3$ | H | 2-CH$_3$ | 1 | O | O | CH$_3$ |
| 468 | B1 | 4-CF$_3$-5-F | H | H | 1 | CH$_3$ | H | 2-CH$_3$ | 1 | O | O | CH$_3$ |
| 469 | B1 | 4,5-diF | H | H | 1 | CH$_3$ | H | 2-CH$_3$ | 1 | O | O | CH$_3$ |

TABLE 8-continued

| | | | | | | | | | | | | |
|---|---|---|---|---|---|---|---|---|---|---|---|---|
| 470 | B1 | 4-Cl-5-F | H | H | 1 | CH$_3$ | H | 2-CH$_3$ | 1 | O | O | CH$_3$ |
| 471 | B1 | 4,5-diOCH$_3$ | H | H | 1 | CH$_3$ | H | 2-CH$_3$ | 1 | O | O | CH$_3$ |
| 472 | B1 | 4-OEt-5-CH$_3$ | H | H | 1 | CH$_3$ | H | 2-CH$_3$ | 1 | O | O | CH$_3$ |
| 473 | B1 | 4-OCF$_3$-5-F | H | H | 1 | CH$_3$ | H | 2-CH$_3$ | 1 | O | O | CH$_3$ |
| 474 | B1 | 4-CH$_3$ | H | CH$_3$ | 1 | CH$_3$ | H | 2-CH$_3$ | 1 | O | O | CH$_3$ |
| 475 | B1 | 4-Et | H | CH$_3$ | 1 | CH$_3$ | H | 2-CH$_3$ | 1 | O | O | CH$_3$ |
| 476 | B1 | 4-CH$_3$ | H | Et | 1 | CH$_3$ | H | 2-CH$_3$ | 1 | O | O | CH$_3$ |
| 477 | B1 | 4-CH$_3$ | H | i-Pr | 1 | CH$_3$ | H | 2-CH$_3$ | 1 | O | O | CH$_3$ |
| 478 | B1 | 4-CH$_3$ | CH$_3$ | Et | 1 | CH$_3$ | H | 2-CH$_3$ | 1 | O | O | CH$_3$ |
| 479 | B1 | 4-CH$_3$ | H | F | 1 | CH$_3$ | H | 2-CH$_3$ | 1 | O | O | CH$_3$ |

TABLE 9

| | | | | | | | | | | | | |
|---|---|---|---|---|---|---|---|---|---|---|---|---|
| 480 | B1 | 4-CH$_3$ | F | F | 1 | CH$_3$ | H | 2-CH$_3$ | 1 | O | O | CH$_3$ |
| 481 | B1 | 4-CH$_3$ | H | CF$_3$ | 1 | CH$_3$ | H | 2-CH$_3$ | 1 | O | O | CH$_3$ |
| 482 | B1 | 4-CH$_3$ | H | c-Pr | 1 | CH$_3$ | H | 2-CH$_3$ | 1 | O | O | CH$_3$ |
| 483 | B1 | 4-CH$_3$ | —CH2CH2— | | 1 | CH$_3$ | H | 2-CH$_3$ | 1 | O | O | CH$_3$ |
| 484 | B1 | 4-CH$_3$ | —CH2CH2CH2— | | 1 | CH$_3$ | H | 2-CH$_3$ | 1 | O | O | CH$_3$ |
| 485 | B1 | 4-CH$_3$ | —CH2CH(CH3)— | | 1 | CH$_3$ | H | 2-CH$_3$ | 1 | O | O | CH$_3$ |
| 486 | B1 | 4-CH$_3$ | —CH2C(CH3)2— | | 1 | CH$_3$ | H | 2-CH$_3$ | 1 | O | O | CH$_3$ |
| 487 | B1 | 4-CH$_3$ | H | H | 1 | H | H | 2-CH$_3$ | 1 | O | O | CH$_3$ |
| 488 | B1 | 4-CH$_3$ | H | H | 1 | Et | H | 2-CH$_3$ | 1 | O | O | CH$_3$ |
| 489 | B1 | 4-CH$_3$ | H | H | 1 | c-Pr | H | 2-CH$_3$ | 1 | O | O | CH$_3$ |
| 490 | B1 | 4-CH$_3$ | H | H | 1 | CH=CH$_2$ | H | 2-CH$_3$ | 1 | O | O | CH$_3$ |
| 491 | B1 | 4-CH$_3$ | H | H | 1 | CH$_2$CH=CH$_2$ | H | 2-CH$_3$ | 1 | O | O | CH$_3$ |
| 492 | B1 | 4-CH$_3$ | H | H | 1 | ethynyl | H | 2-CH$_3$ | 1 | O | O | CH$_3$ |
| 493 | B1 | 4-CH$_3$ | H | H | 1 | Propargyl | H | 2-CH$_3$ | 1 | O | O | CH$_3$ |
| 494 | B1 | 4-CH$_3$ | H | H | 1 | CF$_3$ | H | 2-CH$_3$ | 1 | O | O | CH$_3$ |
| 495 | B1 | 4-CH$_3$ | H | H | 1 | CH=CHCl | H | 2-CH$_3$ | 1 | O | O | CH$_3$ |
| 496 | B1 | 4-CH$_3$ | H | H | 1 | 3,3,2-tri-Iodo-allyl | H | 2-CH$_3$ | 1 | O | O | CH$_3$ |
| 497 | B1 | 4-CH$_3$ | H | H | 1 | 3-Iodopropargyl | H | 2-CH$_3$ | 1 | O | O | CH$_3$ |
| 498 | B1 | 4-CH$_3$ | H | H | 1 | CN | H | 2-CH$_3$ | 1 | O | O | CH$_3$ |
| 499 | B1 | 4-CF$_3$ | H | H | 1 | CN | H | 2-CH$_3$ | 1 | O | O | CH$_3$ |
| 500 | B1 | 4-CH$_3$ | H | H | 1 | NO$_2$ | H | 2-CH$_3$ | 1 | O | O | CH$_3$ |
| 501 | B1 | 4-CH$_3$ | H | H | 1 | NH$_2$ | H | 2-CH$_3$ | 1 | O | O | CH$_3$ |
| 502 | B1 | 4-CH$_3$ | H | H | 1 | NHCH$_3$ | H | 2-CH$_3$ | 1 | O | O | CH$_3$ |
| 503 | B1 | 4-CH$_3$ | H | H | 1 | N(CH$_3$)$_2$ | H | 2-CH$_3$ | 1 | O | O | CH$_3$ |
| 504 | B1 | 4-CH$_3$ | H | H | 1 | CH$_3$ | CH$_3$ | 2-CH$_3$ | 1 | O | O | CH$_3$ |
| 505 | B1 | 4-CH$_3$ | H | H | 1 | CH$_3$ | Et | 2-CH$_3$ | 1 | O | O | CH$_3$ |
| 506 | B1 | 4-CH$_3$ | H | H | 1 | CH$_3$ | CH$_3$CO | 2-CH$_3$ | 1 | O | O | CH$_3$ |
| 507 | B1 | 4-CH$_3$ | H | H | 1 | CH$_3$ | CH$_3$CH$_2$CO | 2-CH$_3$ | 1 | O | O | CH$_3$ |
| 508 | B1 | 4-CH$_3$ | H | H | 1 | CH$_3$ | PhCO | 2-CH$_3$ | 1 | O | O | CH$_3$ |
| 509 | B1 | 4-CH$_3$ | H | H | 1 | CH$_3$ | 4-Cl-PhCO | 2-CH$_3$ | 1 | O | O | CH$_3$ |
| 510 | B1 | 4-CH$_3$ | H | H | 1 | CH$_3$ | PhCH$_2$CO | 2-CH$_3$ | 1 | O | O | CH$_3$ |
| 511 | B1 | 4-CH$_3$ | H | H | 1 | CH$_3$ | CHO | 2-CH$_3$ | 1 | O | O | CH$_3$ |
| 512 | B1 | 4-CH$_3$ | H | H | 1 | CH$_3$ | CH$_3$OCH$_2$ | 2-CH$_3$ | 1 | O | O | CH$_3$ |
| 513 | B1 | 4-CH$_3$ | H | H | 1 | CH$_3$ | CH$_3$CH(OCH$_3$) | 2-CH$_3$ | 1 | O | O | CH$_3$ |
| 514 | B1 | 4-CH$_3$ | H | H | 1 | CH$_3$ | CH$_3$SO$_2$ | 2-CH$_3$ | 1 | O | O | CH$_3$ |
| 515 | B1 | 4-CH$_3$ | H | H | 1 | CH$_3$ | PhSO$_2$ | 2-CH$_3$ | 1 | O | O | CH$_3$ |
| 516 | B1 | 4-CH$_3$ | H | H | 1 | CH$_3$ | 4-CH$_3$-PhSO$_2$ | 2-CH$_3$ | 1 | O | O | CH$_3$ |
| 517 | B1 | 4-CH$_3$ | H | H | 1 | CH$_3$ | H | 2-CH$_3$ | 1 | S | O | CH$_3$ |
| 518 | B1 | 4-CH$_3$ | H | H | 1 | CH$_3$ | H | 2-CH$_3$ | 1 | O | S | CH$_3$ |
| 519 | B1 | 4-CH$_3$ | H | H | 1 | CH$_3$ | H | 2-CH$_3$ | 1 | O | — | CH$_3$ |
| 520 | B1 | 4-CH$_3$ | H | H | 1 | CH$_3$ | H | 2-CH$_3$ | 1 | O | NH | CH$_3$ |
| 521 | B1 | 4-CH$_3$ | H | H | 1 | CH$_3$ | H | 2-CH$_3$ | 1 | O | NCH$_3$ | CH$_3$ |
| 522 | B1 | 4-CH$_3$ | H | H | 1 | CH$_3$ | H | 2-CH$_3$ | 1 | O | O | H |
| 523 | B1 | 4-CH$_3$ | H | H | 1 | CH$_3$ | H | 2-CH$_3$ | 1 | O | O | Et |
| 524 | B1 | 4-CH$_3$ | H | H | 1 | CH$_3$ | H | 2-CH$_3$ | 1 | O | O | n-Pr |
| 525 | B1 | 4-CH$_3$ | H | H | 1 | CH$_3$ | H | 2-CH$_3$ | 1 | O | O | CH$_2$CH=CH$_2$ |
| 526 | B1 | 4-CH$_3$ | H | H | 1 | CH$_3$ | H | 2-CH$_3$ | 1 | O | O | CH=CH$_2$ |
| 527 | B1 | 4-CH$_3$ | H | H | 1 | CH$_3$ | H | 2-CH$_3$ | 1 | O | O | Propargyl |
| 528 | B1 | 4-CH$_3$ | H | H | 1 | CH$_3$ | H | 2-CH$_3$ | 1 | O | O | ethynyl |
| 529 | B1 | 4-CH$_3$ | H | H | 1 | CH$_3$ | H | 2-CH$_3$ | 1 | O | O | CF$_3$ |
| 530 | B1 | 4-CH$_3$ | H | H | 1 | CH$_3$ | H | 2-CH$_3$ | 1 | O | O | CH$_2$CF$_3$ |
| 531 | B1 | 4-CH$_3$ | H | H | 1 | CH$_3$ | H | 2-CH$_3$ | 1 | O | O | CF$_2$CF$_3$ |
| 532 | B1 | 4-CH$_3$ | H | H | 1 | CH$_3$ | H | 2-CH$_3$ | 1 | O | O | CF$_2$CF$_2$H |
| 533 | B1 | 4-CH$_3$ | H | H | 1 | CH$_3$ | H | 2-CH$_3$ | 1 | O | O | CH$_2$CH=CHCl |
| 534 | B1 | 4-CH$_3$ | H | H | 1 | CH$_3$ | H | 2-CH$_3$ | 1 | O | O | 3-Iodo-propargyl |
| 535 | B1 | 4-CH$_3$ | H | H | 1 | CH$_3$ | H | 3-CH$_3$ | 1 | O | O | c-Pr |
| 536 | B1 | 4-CH$_3$ | H | H | 1 | CH$_3$ | H | 2-CH$_3$ | 1 | O | O | c-Hex |
| 537 | B1 | 4-CH$_3$ | H | H | 1 | CH$_3$ | H | 2-CH$_3$ | 1 | O | O | 2-CH$_3$-c-Pr |
| 538 | B2 | — | H | H | 1 | CH$_3$ | H | — | 0 | O | O | CH$_3$ |
| 539 | B2 | — | H | H | 1 | CH$_3$ | H | 2-Cl | 1 | O | O | CH$_3$ |
| 540 | B2 | 2-CH$_3$ | H | H | 1 | CH$_3$ | H | 2-Cl | 1 | O | O | CH$_3$ |
| 541 | B2 | 2-Et | H | H | 1 | CH$_3$ | H | 2-Cl | 1 | O | O | CH$_3$ |

TABLE 10

| No. | Type | R1 | R2 | R3 | n | R4 | R5 | Y | m | A | B | R6 |
|---|---|---|---|---|---|---|---|---|---|---|---|---|
| 542 | B2 | 2-CF₃ | H | H | 1 | CH₃ | H | 2-Cl | 1 | O | O | CH₃ |
| 543 | B2 | 2-F | H | H | 1 | CH₃ | H | 2-Cl | 1 | O | O | CH₃ |
| 544 | B2 | 2-Cl | H | H | 1 | CH₃ | H | 2-Cl | 1 | O | O | CH₃ |
| 545 | B2 | 2-OCH₃ | H | H | 1 | CH₃ | H | 2-Cl | 1 | O | O | CH₃ |
| 546 | B2 | 2-OEt | H | H | 1 | CH₃ | H | 2-Cl | 1 | O | O | CH₃ |
| 547 | B2 | 2-OCF₃ | H | H | 1 | CH₃ | H | 2-Cl | 1 | O | O | CH₃ |
| 548 | B2 | 5-CH₃ | H | H | 1 | CH₃ | H | 2-Cl | 1 | O | O | CH₃ |
| 549 | B2 | 5-Et | H | H | 1 | CH₃ | H | 2-Cl | 1 | O | O | CH₃ |
| 550 | B2 | 5-CF₃ | H | H | 1 | CH₃ | H | 2-Cl | 1 | O | O | CH₃ |
| 551 | B2 | 5-F | H | H | 1 | CH₃ | H | 2-Cl | 1 | O | O | CH₃ |
| 552 | B2 | 5-Cl | H | H | 1 | CH₃ | H | 2-Cl | 1 | O | O | CH₃ |
| 553 | B2 | 5-OCH₃ | H | H | 1 | CH₃ | H | 2-Cl | 1 | O | O | CH₃ |
| 554 | B2 | 5-OEt | H | H | 1 | CH₃ | H | 2-Cl | 1 | O | O | CH₃ |
| 555 | B2 | 5-OCF₃ | H | H | 1 | CH₃ | H | 2-Cl | 1 | O | O | CH₃ |
| 556 | B2 | 2,5-diCH₃ | H | H | 1 | CH₃ | H | 2-Cl | 1 | O | O | CH₃ |
| 557 | B2 | 2-Et-5-CH₃ | H | H | 1 | CH₃ | H | 2-Cl | 1 | O | O | CH₃ |
| 558 | B2 | 2-CF₃-5-F | H | H | 1 | CH₃ | H | 2-Cl | 1 | O | O | CH₃ |
| 559 | B2 | 2,5-diF | H | H | 1 | CH₃ | H | 2-Cl | 1 | O | O | CH₃ |
| 560 | B2 | 2-Cl-5-F | H | H | 1 | CH₃ | H | 2-Cl | 1 | O | O | CH₃ |
| 561 | B2 | 2,5-diOCH₃ | H | H | 1 | CH₃ | H | 2-Cl | 1 | O | O | CH₃ |
| 562 | B2 | 2-OEt-5-CH₃ | H | H | 1 | CH₃ | H | 2-Cl | 1 | O | O | CH₃ |
| 563 | B2 | 2-OCF₃-5-F | H | H | 1 | CH₃ | H | 2-Cl | 1 | O | O | CH₃ |
| 564 | B2 | 2-CH₃ | H | CH₃ | 1 | CH₃ | H | 2-Cl | 1 | O | O | CH₃ |
| 565 | B2 | 2-Et | H | CH₃ | 1 | CH₃ | H | 2-Cl | 1 | O | O | CH₃ |
| 566 | B2 | 2-CH₃ | H | Et | 1 | CH₃ | H | 2-Cl | 1 | O | O | CH₃ |
| 567 | B2 | 2-CH₃ | H | i-Pr | 1 | CH₃ | H | 2-Cl | 1 | O | O | CH₃ |
| 568 | B2 | 2-CH₃ | CH₃ | Et | 1 | CH₃ | H | 2-Cl | 1 | O | O | CH₃ |
| 569 | B2 | 2-CH₃ | H | F | 1 | CH₃ | H | 2-Cl | 1 | O | O | CH₃ |
| 570 | B2 | 2-CH₃ | F | F | 1 | CH₃ | H | 2-Cl | 1 | O | O | CH₃ |
| 571 | B2 | 2-CH₃ | H | CF₃ | 1 | CH₃ | H | 2-Cl | 1 | O | O | CH₃ |
| 572 | B2 | 2-CH₃ | H | c-Pr | 1 | CH₃ | H | 2-Cl | 1 | O | O | CH₃ |
| 573 | B2 | 2-CH₃ | —CH2CH2— | | 1 | CH₃ | H | 2-Cl | 1 | O | O | CH₃ |
| 574 | B2 | 2-CH₃ | —CH2CH2CH2— | | 1 | CH₃ | H | 2-Cl | 1 | O | O | CH₃ |
| 575 | B2 | 2-CH₃ | —CH2CH(CH3)— | | 1 | CH₃ | H | 2-Cl | 1 | O | O | CH₃ |
| 576 | B2 | 2-CH₃ | —CH2C(CH3)2— | | 1 | CH₃ | H | 2-Cl | 1 | O | O | CH₃ |
| 577 | B2 | 2-CH₃ | H | H | 1 | H | H | 2-Cl | 1 | O | O | CH₃ |
| 578 | B2 | 2-CH₃ | H | H | 1 | Et | H | 2-Cl | 1 | O | O | CH₃ |
| 579 | B2 | 2-CH₃ | H | H | 1 | c-Pr | H | 2-Cl | 1 | O | O | CH₃ |
| 580 | B2 | 2-CH₃ | H | H | 1 | CH=CH₂ | H | 2-Cl | 1 | O | O | CH₃ |
| 581 | B2 | 2-CH₃ | H | H | 1 | CH₂CH=CH₂ | H | 2-Cl | 1 | O | O | CH₃ |
| 582 | B2 | 2-CH₃ | H | H | 1 | ethynyl | H | 2-Cl | 1 | O | O | CH₃ |
| 583 | B2 | 2-CH₃ | H | H | 1 | Propargyl | H | 2-Cl | 1 | O | O | CH₃ |
| 584 | B2 | 2-CH₃ | H | H | 1 | CF₃ | H | 2-Cl | 1 | O | O | CH₃ |
| 585 | B2 | 2-CH₃ | H | H | 1 | CH=CHCl | H | 2-Cl | 1 | O | O | CH₃ |
| 586 | B2 | 2-CH₃ | H | H | 1 | 3,3,2-tri-Iodo-allyl | H | 2-Cl | 1 | O | O | CH₃ |
| 587 | B2 | 2-CH₃ | H | H | 1 | 3-Iodopropargyl | H | 2-Cl | 1 | O | O | CH₃ |
| 588 | B2 | 2-CH₃ | H | H | 1 | CN | H | 2-Cl | 1 | O | O | CH₃ |
| 589 | B2 | 2-CF₃ | H | H | 1 | CN | H | 2-Cl | 1 | O | O | CH₃ |
| 590 | B2 | 2-CH₃ | H | H | 1 | NO₂ | H | 2-Cl | 1 | O | O | CH₃ |
| 591 | B2 | 2-CH₃ | H | H | 1 | NH₂ | H | 2-Cl | 1 | O | O | CH₃ |
| 592 | B2 | 2-CH₃ | H | H | 1 | NHCH₃ | H | 2-Cl | 1 | O | O | CH₃ |
| 593 | B2 | 2-CH₃ | H | H | 1 | N(CH₃)₂ | H | 2-Cl | 1 | O | O | CH₃ |
| 594 | B2 | 2-CH₃ | H | H | 1 | CH₃ | CH₃ | 2-Cl | 1 | O | O | CH₃ |
| 595 | B2 | 2-CH₃ | H | H | 1 | CH₃ | Et | 2-Cl | 1 | O | O | CH₃ |
| 596 | B2 | 2-CH₃ | H | H | 1 | CH₃ | CH₃CO | 2-Cl | 1 | O | O | CH₃ |
| 597 | B2 | 2-CH₃ | H | H | 1 | CH₃ | CH₃CH₂CO | 2-Cl | 1 | O | O | CH₃ |
| 598 | B2 | 2-CH₃ | H | H | 1 | CH₃ | PhCO | 2-Cl | 1 | O | O | CH₃ |
| 599 | B2 | 2-CH₃ | H | H | 1 | CH₃ | 4-Cl-PhCO | 2-Cl | 1 | O | O | CH₃ |
| 600 | B2 | 2-CH₃ | H | H | 1 | CH₃ | PhCH₂CO | 2-Cl | 1 | O | O | CH₃ |
| 601 | B2 | 2-CH₃ | H | H | 1 | CH₃ | CHO | 2-Cl | 1 | O | O | CH₃ |
| 602 | B2 | 2-CH₃ | H | H | 1 | CH₃ | CH₃OCH₂ | 2-Cl | 1 | O | O | CH₃ |
| 603 | B2 | 2-CH₃ | H | H | 1 | CH₃ | CH₃CH(OCH₃) | 2-Cl | 1 | O | O | CH₃ |

TABLE 11

| No. | Type | R1 | R2 | R3 | n | R4 | R5 | Y | m | A | B | R6 |
|---|---|---|---|---|---|---|---|---|---|---|---|---|
| 604 | B2 | 2-CH₃ | H | H | 1 | CH₃ | CH₃SO₂ | 2-Cl | 1 | O | O | CH₃ |
| 605 | B2 | 2-CH₃ | H | H | 1 | CH₃ | PhSO₂ | 2-Cl | 1 | O | O | CH₃ |
| 606 | B2 | 2-CH₃ | H | H | 1 | CH₃ | 4-CH₃-PhSO₂ | 2-Cl | 1 | O | O | CH₃ |
| 607 | B2 | 2-CH₃ | H | H | 1 | CH₃ | H | 2-Cl | 1 | S | O | CH₃ |
| 608 | B2 | 2-CH₃ | H | H | 1 | CH₃ | H | 2-Cl | 1 | O | S | CH₃ |
| 609 | B2 | 2-CH₃ | H | H | 1 | CH₃ | H | 2-Cl | 1 | O | — | CH₃ |
| 610 | B2 | 2-CH₃ | H | H | 1 | CH₃ | H | 2-Cl | 1 | O | NH | CH₃ |
| 611 | B2 | 2-CH₃ | H | H | 1 | CH₃ | H | 2-Cl | 1 | O | NCH₃ | CH₃ |
| 612 | B2 | 2-CH₃ | H | H | 1 | CH₃ | H | 2-Cl | 1 | O | O | H |
| 613 | B2 | 2-CH₃ | H | H | 1 | CH₃ | H | 2-Cl | 1 | O | O | Et |
| 614 | B2 | 2-CH₃ | H | H | 1 | CH₃ | H | 2-Cl | 1 | O | O | n-Pr |
| 615 | B2 | 2-CH₃ | H | H | 1 | CH₃ | H | 2-Cl | 1 | O | O | CH₂CH=CH₂ |

TABLE 11-continued

| | | | | | | | | | | | | |
|---|---|---|---|---|---|---|---|---|---|---|---|---|
| 616 | B2 | 2-CH$_3$ | H | H | 1 | CH$_3$ | H | 2-Cl | 1 | O | O | CH=CH$_2$ |
| 617 | B2 | 2-CH$_3$ | H | H | 1 | CH$_3$ | H | 2-Cl | 1 | O | O | Propargyl |
| 618 | B2 | 2-CH$_3$ | H | H | 1 | CH$_3$ | H | 2-Cl | 1 | O | O | ethynyl |
| 619 | B2 | 2-CH$_3$ | H | H | 1 | CH$_3$ | H | 2-Cl | 1 | O | O | CF$_3$ |
| 620 | B2 | 2-CH$_3$ | H | H | 1 | CH$_3$ | H | 2-Cl | 1 | O | O | CH$_2$CF$_3$ |
| 621 | B2 | 2-CH$_3$ | H | H | 1 | CH$_3$ | H | 2-Cl | 1 | O | O | CF$_3$CF$_3$ |
| 622 | B2 | 2-CH$_3$ | H | H | 1 | CH$_3$ | H | 2-Cl | 1 | O | O | CF$_2$CF$_2$H |
| 623 | B2 | 2-CH$_3$ | H | H | 1 | CH$_3$ | H | 2-Cl | 1 | O | O | CH$_2$CH=CHCl |
| 624 | B2 | 2-CH$_3$ | H | H | 1 | CH$_3$ | H | 2-Cl | 1 | O | O | 3-Iodo-propargyl |
| 625 | B2 | 2-CH$_3$ | H | H | 1 | CH$_3$ | H | 2-Cl | 1 | O | O | c-Pr |
| 626 | B2 | 2-CH$_3$ | H | H | 1 | CH$_3$ | H | 2-Cl | 1 | O | O | c-Hex |
| 627 | B2 | 2-CH$_3$ | H | H | 1 | CH$_3$ | H | 2-Cl | 1 | O | O | 2-CH$_3$-c-Pr |
| 628 | B2 | — | H | H | 1 | CH$_3$ | H | 2-CH$_3$ | 1 | O | O | CH$_3$ |
| 629 | B2 | 2-CH$_3$ | H | H | 1 | CH$_3$ | H | 2-CH$_3$ | 1 | O | O | CH$_3$ |
| 630 | B2 | 2-Et | H | H | 1 | CH$_3$ | H | 2-CH$_3$ | 1 | O | O | CH$_3$ |
| 631 | B2 | 2-CF$_3$ | H | H | 1 | CH$_3$ | H | 2-CH$_3$ | 1 | O | O | CH$_3$ |
| 632 | B2 | 2-F | H | H | 1 | CH$_3$ | H | 2-CH$_3$ | 1 | O | O | CH$_3$ |
| 633 | B2 | 2-Cl | H | H | 1 | CH$_3$ | H | 2-CH$_3$ | 1 | O | O | CH$_3$ |
| 634 | B2 | 2-OCH$_3$ | H | H | 1 | CH$_3$ | H | 2-CH$_3$ | 1 | O | O | CH$_3$ |
| 635 | B2 | 2-OEt | H | H | 1 | CH$_3$ | H | 2-CH$_3$ | 1 | O | O | CH$_3$ |
| 636 | B2 | 2-OCF$_3$ | H | H | 1 | CH$_3$ | H | 2-CH$_3$ | 1 | O | O | CH$_3$ |
| 637 | B2 | 5-CH$_3$ | H | H | 1 | CH$_3$ | H | 2-CH$_3$ | 1 | O | O | CH$_3$ |
| 638 | B2 | 5-Et | H | H | 1 | CH$_3$ | H | 2-CH$_3$ | 1 | O | O | CH$_3$ |
| 639 | B2 | 5-CF$_3$ | H | H | 1 | CH$_3$ | H | 2-CH$_3$ | 1 | O | O | CH$_3$ |
| 640 | B2 | 5-F | H | H | 1 | CH$_3$ | H | 2-CH$_3$ | 1 | O | O | CH$_3$ |
| 641 | B2 | 5-Cl | H | H | 1 | CH$_3$ | H | 2-CH$_3$ | 1 | O | O | CH$_3$ |
| 642 | B2 | 5-OCH$_3$ | H | H | 1 | CH$_3$ | H | 2-CH$_3$ | 1 | O | O | CH$_3$ |
| 643 | B2 | 5-OEt | H | H | 1 | CH$_3$ | H | 2-CH$_3$ | 1 | O | O | CH$_3$ |
| 644 | B2 | 5-OCF$_3$ | H | H | 1 | CH$_3$ | H | 2-CH$_3$ | 1 | O | O | CH$_3$ |
| 645 | B2 | 2,5-diCH$_3$ | H | H | 1 | CH$_3$ | H | 2-CH$_3$ | 1 | O | O | CH$_3$ |
| 646 | B2 | 2-Et-5-CH$_3$ | H | H | 1 | CH$_3$ | H | 2-CH$_3$ | 1 | O | O | CH$_3$ |
| 647 | B2 | 2-CF$_3$-5-F | H | H | 1 | CH$_3$ | H | 2-CH$_3$ | 1 | O | O | CH$_3$ |
| 648 | B2 | 2,5-diF | H | H | 1 | CH$_3$ | H | 2-CH$_3$ | 1 | O | O | CH$_3$ |
| 649 | B2 | 2-Cl-5-F | H | H | 1 | CH$_3$ | H | 2-CH$_3$ | 1 | O | O | CH$_3$ |
| 650 | B2 | 2,5-diOCH$_3$ | H | H | 1 | CH$_3$ | H | 2-CH$_3$ | 1 | O | O | CH$_3$ |
| 651 | B2 | 2-OEt-5-CH$_3$ | H | H | 1 | CH$_3$ | H | 2-CH$_3$ | 1 | O | O | CH$_3$ |
| 652 | B2 | 2-OCF$_3$-5-F | H | H | 1 | CH$_3$ | H | 2-CH$_3$ | 1 | O | O | CH$_3$ |
| 653 | B2 | 2-CH$_3$ | H | CH$_3$ | 1 | CH$_3$ | H | 2-CH$_3$ | 1 | O | O | CH$_3$ |
| 654 | B2 | 2-Et | H | CH$_3$ | 1 | CH$_3$ | H | 2-CH$_3$ | 1 | O | O | CH$_3$ |
| 655 | B2 | 2-CH$_3$ | H | Et | 1 | CH$_3$ | H | 2-CH$_3$ | 1 | O | O | CH$_3$ |
| 656 | B2 | 2-CH$_3$ | H | i-Pr | 1 | CH$_3$ | H | 2-CH$_3$ | 1 | O | O | CH$_3$ |
| 657 | B2 | 2-CH$_3$ | CH$_3$ | Et | 1 | CH$_3$ | H | 2-CH$_3$ | 1 | O | O | CH$_3$ |
| 658 | B2 | 2-CH$_3$ | H | F | 1 | CH$_3$ | H | 2-CH$_3$ | 1 | O | O | CH$_3$ |
| 659 | B2 | 2-CH$_3$ | F | F | 1 | CH$_3$ | H | 2-CH$_3$ | 1 | O | O | CH$_3$ |
| 660 | B2 | 2-CH$_3$ | H | CF$_3$ | 1 | CH$_3$ | H | 2-CH$_3$ | 1 | O | O | CH$_3$ |
| 661 | B2 | 2-CH$_3$ | H | c-Pr | 1 | CH$_3$ | H | 2-CH$_3$ | 1 | O | O | CH$_3$ |
| 662 | B2 | 2-CH$_3$ | —CH2CH2— | | 1 | CH$_3$ | H | 2-CH$_3$ | 1 | O | O | CH$_3$ |
| 663 | B2 | 2-CH$_3$ | —CH2CH2CH2— | | 1 | CH$_3$ | H | 2-CH$_3$ | 1 | O | O | CH$_3$ |
| 664 | B2 | 2-CH$_3$ | —CH2CH(CH3)— | | 1 | CH$_3$ | H | 2-CH$_3$ | 1 | O | O | CH$_3$ |
| 665 | B2 | 2-CH$_3$ | —CH2C(CH3)2— | | 1 | CH$_3$ | H | 2-CH$_3$ | 1 | O | O | CH$_3$ |

TABLE 12

| | | | | | | | | | | | | |
|---|---|---|---|---|---|---|---|---|---|---|---|---|
| 666 | B2 | 2-CH$_3$ | H | H | 1 | H | H | 2-CH$_3$ | 1 | O | O | CH$_3$ |
| 667 | B2 | 2-CH$_3$ | H | H | 1 | Et | H | 2-CH$_3$ | 1 | O | O | CH$_3$ |
| 668 | B2 | 2-CH$_3$ | H | H | 1 | c-Pr | H | 2-CH$_3$ | 1 | O | O | CH$_3$ |
| 669 | B2 | 2-CH$_3$ | H | H | 1 | CH=CH$_2$ | H | 2-CH$_3$ | 1 | O | O | CH$_3$ |
| 670 | B2 | 2-CH$_3$ | H | H | 1 | CH$_2$CH=CH$_2$ | H | 2-CH$_3$ | 1 | O | O | CH$_3$ |
| 671 | B2 | 2-CH$_3$ | H | H | 1 | ethynyl | H | 2-CH$_3$ | 1 | O | O | CH$_3$ |
| 672 | B2 | 2-CH$_3$ | H | H | 1 | Propargyl | H | 2-CH$_3$ | 1 | O | O | CH$_3$ |
| 673 | B2 | 2-CH$_3$ | H | H | 1 | CF$_3$ | H | 2-CH$_3$ | 1 | O | O | CH$_3$ |
| 674 | B2 | 2-CH$_3$ | H | H | 1 | CH=CHCl | H | 2-CH$_3$ | 1 | O | O | CH$_3$ |
| 675 | B2 | 2-CH$_3$ | H | H | 1 | 3,3,2-tri-Iodo-allyl | H | 2-CH$_3$ | 1 | O | O | CH$_3$ |
| 676 | B2 | 2-CH$_3$ | H | H | 1 | 3-Iodopropargyl | H | 2-CH$_3$ | 1 | O | O | CH$_3$ |
| 677 | B2 | 2-CH$_3$ | H | H | 1 | CN | H | 2-CH$_3$ | 1 | O | O | CH$_3$ |
| 678 | B2 | 2-CF$_3$ | H | H | 1 | CN | H | 2-CH$_3$ | 1 | O | O | CH$_3$ |
| 679 | B2 | 2-CH$_3$ | H | H | 1 | NO$_2$ | H | 2-CH$_3$ | 1 | O | O | CH$_3$ |
| 680 | B2 | 2-CH$_3$ | H | H | 1 | NH$_2$ | H | 2-CH$_3$ | 1 | O | O | CH$_3$ |
| 681 | B2 | 2-CH$_3$ | H | H | 1 | NHCH$_3$ | H | 2-CH$_3$ | 1 | O | O | CH$_3$ |
| 682 | B2 | 2-CH$_3$ | H | H | 1 | N(CH$_3$)$_2$ | H | 2-CH$_3$ | 1 | O | O | CH$_3$ |
| 683 | B2 | 2-CH$_3$ | H | H | 1 | CH$_3$ | CH$_3$ | 2-CH$_3$ | 1 | O | O | CH$_3$ |
| 684 | B2 | 2-CH$_3$ | H | H | 1 | CH$_3$ | Et | 2-CH$_3$ | 1 | O | O | CH$_3$ |
| 685 | B2 | 2-CH$_3$ | H | H | 1 | CH$_3$ | CH$_3$CO | 2-CH$_3$ | 1 | O | O | CH$_3$ |
| 686 | B2 | 2-CH$_3$ | H | H | 1 | CH$_3$ | CH$_3$CH$_2$CO | 2-CH$_3$ | 1 | O | O | CH$_3$ |
| 687 | B2 | 2-CH$_3$ | H | H | 1 | CH$_3$ | PhCO | 2-CH$_3$ | 1 | O | O | CH$_3$ |
| 688 | B2 | 2-CH$_3$ | H | H | 1 | CH$_3$ | 4-Cl-PhCO | 2-CH$_3$ | 1 | O | O | CH$_3$ |
| 689 | B2 | 2-CH$_3$ | H | H | 1 | CH$_3$ | PhCH$_2$CO | 2-CH$_3$ | 1 | O | O | CH$_3$ |

TABLE 12-continued

| | | | | | | | | | | | | |
|---|---|---|---|---|---|---|---|---|---|---|---|---|
| 690 | B2 | 2-CH$_3$ | H | H | 1 | CH$_3$ | CHO | 2-CH$_3$ | 1 | O | O | CH$_3$ |
| 691 | B2 | 2-CH$_3$ | H | H | 1 | CH$_3$ | CH$_3$OCH$_2$ | 2-CH$_3$ | 1 | O | O | CH$_3$ |
| 692 | B2 | 2-CH$_3$ | H | H | 1 | CH$_3$ | CH$_3$CH(OCH$_3$) | 2-CH$_3$ | 1 | O | O | CH$_3$ |
| 693 | B2 | 2-CH$_3$ | H | H | 1 | CH$_3$ | CH$_3$SO$_2$ | 2-CH$_3$ | 1 | O | O | CH$_3$ |
| 694 | B2 | 2-CH$_3$ | H | H | 1 | CH$_3$ | PhSO$_2$ | 2-CH$_3$ | 1 | O | O | CH$_3$ |
| 695 | B2 | 2-CH$_3$ | H | H | 1 | CH$_3$ | 4-CH$_3$-PhSO$_2$ | 2-CH$_3$ | 1 | O | O | CH$_3$ |
| 696 | B2 | 2-CH$_3$ | H | H | 1 | CH$_3$ | H | 2-CH$_3$ | 1 | S | O | CH$_3$ |
| 697 | B2 | 2-CH$_3$ | H | H | 1 | CH$_3$ | H | 2-CH$_3$ | 1 | O | S | CH$_3$ |
| 698 | B2 | 2-CH$_3$ | H | H | 1 | CH$_3$ | H | 2-CH$_3$ | 1 | O | — | CH$_3$ |
| 699 | B2 | 2-CH$_3$ | H | H | 1 | CH$_3$ | H | 2-CH$_3$ | 1 | O | NH | CH$_3$ |
| 700 | B2 | 2-CH$_3$ | H | H | 1 | CH$_3$ | H | 2-CH$_3$ | 1 | O | NCH$_3$ | CH$_3$ |
| 701 | B2 | 2-CH$_3$ | H | H | 1 | CH$_3$ | H | 2-CH$_3$ | 1 | O | O | H |
| 702 | B2 | 2-CH$_3$ | H | H | 1 | CH$_3$ | H | 2-CH$_3$ | 1 | O | O | Et |
| 703 | B2 | 2-CH$_3$ | H | H | 1 | CH$_3$ | H | 2-CH$_3$ | 1 | O | O | n-Pr |
| 704 | B2 | 2-CH$_3$ | H | H | 1 | CH$_3$ | H | 2-CH$_3$ | 1 | O | O | CH$_2$CH=CH$_2$ |
| 705 | B2 | 2-CH$_3$ | H | H | 1 | CH$_3$ | H | 2-CH$_3$ | 1 | O | O | CH=CH$_2$ |
| 706 | B2 | 2-CH$_3$ | H | H | 1 | CH$_3$ | H | 2-CH$_3$ | 1 | O | O | Propargyl |
| 707 | B2 | 2-CH$_3$ | H | H | 1 | CH$_3$ | H | 2-CH$_3$ | 1 | O | O | ethynyl |
| 708 | B2 | 2-CH$_3$ | H | H | 1 | CH$_3$ | H | 2-CH$_3$ | 1 | O | O | CF$_3$ |
| 709 | B2 | 2-CH$_3$ | H | H | 1 | CH$_3$ | H | 2-CH$_3$ | 1 | O | O | CH$_2$CF$_3$ |
| 710 | B2 | 2-CH$_3$ | H | H | 1 | CH$_3$ | H | 2-CH$_3$ | 1 | O | O | CF$_2$CF$_3$ |
| 711 | B2 | 2-CH$_3$ | H | H | 1 | CH$_3$ | H | 2-CH$_3$ | 1 | O | O | CF$_2$CF$_2$H |
| 712 | B2 | 2-CH$_3$ | H | H | 1 | CH$_3$ | H | 2-CH$_3$ | 1 | O | O | CH$_2$CH=CHCl |
| 713 | B2 | 2-CH$_3$ | H | H | 1 | CH$_3$ | H | 2-CH$_3$ | 1 | O | O | 3-Iodo-propargyl |
| 714 | B2 | 2-CH$_3$ | H | H | 1 | CH$_3$ | H | 2-CH$_3$ | 1 | O | O | c-Pr |
| 715 | B2 | 2-CH$_3$ | H | H | 1 | CH$_3$ | H | 2-CH$_3$ | 1 | O | O | c-Hex |
| 716 | B2 | 2-CH$_3$ | H | H | 1 | CH$_3$ | H | 2-CH$_3$ | 1 | O | O | 2-CH$_3$-c-Pr |
| 717 | C1 | — | H | H | 1 | CH$_3$ | H | — | 0 | O | O | CH$_3$ |
| 718 | C1 | — | H | H | 1 | CH$_3$ | H | 2-Cl | 1 | O | O | CH$_3$ |
| 719 | C1 | 4-CH$_3$ | H | H | 1 | CH$_3$ | H | 2-Cl | 1 | O | O | CH$_3$ |
| 720 | C1 | 4-Et | H | H | 1 | CH$_3$ | H | 2-Cl | 1 | O | O | CH$_3$ |
| 721 | C1 | 4-CF$_3$ | H | H | 1 | CH$_3$ | H | 2-Cl | 1 | O | O | CH$_3$ |
| 722 | C1 | 4-F | H | H | 1 | CH$_3$ | H | 2-Cl | 1 | O | O | CH$_3$ |
| 723 | C1 | 4-Cl | H | H | 1 | CH$_3$ | H | 2-Cl | 1 | O | O | CH$_3$ |
| 724 | C1 | 4-OCH$_3$ | H | H | 1 | CH$_3$ | H | 2-Cl | 1 | O | O | CH$_3$ |
| 725 | C1 | 4-OEt | H | H | 1 | CH$_3$ | H | 2-Cl | 1 | O | O | CH$_3$ |
| 726 | C1 | 4-OCF$_3$ | H | H | 1 | CH$_3$ | H | 2-Cl | 1 | O | O | CH$_3$ |
| 727 | C1 | 5-CH$_3$ | H | H | 1 | CH$_3$ | H | 2-Cl | 1 | O | O | CH$_3$ |

TABLE 13

| | | | | | | | | | | | | |
|---|---|---|---|---|---|---|---|---|---|---|---|---|
| 728 | C1 | 5-Et | H | H | 1 | CH$_3$ | H | 2-Cl | 1 | O | O | CH$_3$ |
| 729 | C1 | 5-CF$_3$ | H | H | 1 | CH$_3$ | H | 2-Cl | 1 | O | O | CH$_3$ |
| 730 | C1 | 5-F | H | H | 1 | CH$_3$ | H | 2-Cl | 1 | O | O | CH$_3$ |
| 731 | C1 | 5-Cl | H | H | 1 | CH$_3$ | H | 2-Cl | 1 | O | O | CH$_3$ |
| 732 | C1 | 5-OCH$_3$ | H | H | 1 | CH$_3$ | H | 2-Cl | 1 | O | O | CH$_3$ |
| 733 | C1 | 5-OEt | H | H | 1 | CH$_3$ | H | 2-Cl | 1 | O | O | CH$_3$ |
| 734 | C1 | 5-OCF$_3$ | H | H | 1 | CH$_3$ | H | 2-Cl | 1 | O | O | CH$_3$ |
| 735 | C1 | 4,5-diCH$_3$ | H | H | 1 | CH$_3$ | H | 2-Cl | 1 | O | O | CH$_3$ |
| 736 | C1 | 4-Et-5-CH$_3$ | H | H | 1 | CH$_3$ | H | 2-Cl | 1 | O | O | CH$_3$ |
| 737 | C1 | 4-CF$_3$-5-F | H | H | 1 | CH$_3$ | H | 2-Cl | 1 | O | O | CH$_3$ |
| 738 | C1 | 4,5-diF | H | H | 1 | CH$_3$ | H | 2-Cl | 1 | O | O | CH$_3$ |
| 739 | C1 | 4-Cl-5-F | H | H | 1 | CH$_3$ | H | 2-Cl | 1 | O | O | CH$_3$ |
| 740 | C1 | 4,5-diOCH$_3$ | H | H | 1 | CH$_3$ | H | 2-Cl | 1 | O | O | CH$_3$ |
| 741 | C1 | 4-OEt-5-CH$_3$ | H | H | 1 | CH$_3$ | H | 2-Cl | 1 | O | O | CH$_3$ |
| 742 | C1 | 4-OCF$_3$-5-F | H | H | 1 | CH$_3$ | H | 2-Cl | 1 | O | O | CH$_3$ |
| 743 | C1 | 4-CH$_3$ | H | CH$_3$ | 1 | CH$_3$ | H | 2-Cl | 1 | O | O | CH$_3$ |
| 744 | C1 | 4-Et | H | CH$_3$ | 1 | CH$_3$ | H | 2-Cl | 1 | O | O | CH$_3$ |
| 745 | C1 | 4-CH$_3$ | H | Et | 1 | CH$_3$ | H | 2-Cl | 1 | O | O | CH$_3$ |
| 746 | C1 | 4-CH$_3$ | H | i-Pr | 1 | CH$_3$ | H | 2-Cl | 1 | O | O | CH$_3$ |
| 747 | C1 | 4-CH$_3$ | CH$_3$ | Et | 1 | CH$_3$ | H | 2-Cl | 1 | O | O | CH$_3$ |
| 748 | C1 | 4-CH$_3$ | H | F | 1 | CH$_3$ | H | 2-Cl | 1 | O | O | CH$_3$ |
| 749 | C1 | 4-CH$_3$ | F | F | 1 | CH$_3$ | H | 2-Cl | 1 | O | O | CH$_3$ |
| 750 | C1 | 4-CH$_3$ | H | CF$_3$ | 1 | CH$_3$ | H | 2-Cl | 1 | O | O | CH$_3$ |
| 751 | C1 | 4-CH$_3$ | H | c-Pr | 1 | CH$_3$ | H | 2-Cl | 1 | O | O | CH$_3$ |
| 752 | C1 | 4-CH$_3$ | —CH2CH2— | | 1 | CH$_3$ | H | 2-Cl | 1 | O | O | CH$_3$ |
| 753 | C1 | 4-CH$_3$ | —CH2CH2CH2— | | 1 | CH$_3$ | H | 2-Cl | 1 | O | O | CH$_3$ |
| 754 | C1 | 4-CH$_3$ | —CH2CH(CH3)— | | 1 | CH$_3$ | H | 2-Cl | 1 | O | O | CH$_3$ |
| 755 | C1 | 4-CH$_3$ | —CH2C(CH3)2— | | 1 | CH$_3$ | H | 2-Cl | 1 | O | O | CH$_3$ |
| 756 | C1 | 4-CH$_3$ | H | H | 1 | H | H | 2-Cl | 1 | O | O | CH$_3$ |
| 757 | C1 | 4-CH$_3$ | H | H | 1 | Et | H | 2-Cl | 1 | O | O | CH$_3$ |
| 758 | C1 | 4-CH$_3$ | H | H | 1 | c-Pr | H | 2-Cl | 1 | O | O | CH$_3$ |
| 759 | C1 | 4-CH$_3$ | H | H | 1 | CH=CH$_2$ | H | 2-Cl | 1 | O | O | CH$_3$ |
| 760 | C1 | 4-CH$_3$ | H | H | 1 | CH$_2$CH=CH$_2$ | H | 2-Cl | 1 | O | O | CH$_3$ |
| 761 | C1 | 4-CH$_3$ | H | H | 1 | ethynyl | H | 2-Cl | 1 | O | O | CH$_3$ |
| 762 | C1 | 4-CH$_3$ | H | H | 1 | Propargyl | H | 2-Cl | 1 | O | O | CH$_3$ |
| 763 | C1 | 4-CH$_3$ | H | H | 1 | CF$_3$ | H | 2-Cl | 1 | O | O | CH$_3$ |

TABLE 13-continued

| | | | | | | | | | | | | |
|---|---|---|---|---|---|---|---|---|---|---|---|---|
| 764 | C1 | 4-CH$_3$ | H | H | 1 | CH=CHCl | H | 2-Cl | 1 | O | O | CH$_3$ |
| 765 | C1 | 4-CH$_3$ | H | H | 1 | 3,3,2-tri-Iodo-allyl | H | 2-Cl | 1 | O | O | CH$_3$ |
| 766 | C1 | 4-CH$_3$ | H | H | 1 | 3-Iodopropargyl | H | 2-Cl | 1 | O | O | CH$_3$ |
| 767 | C1 | 4-CH$_3$ | H | H | 1 | CN | H | 2-Cl | 1 | O | O | CH$_3$ |
| 768 | C1 | 4-CF$_3$ | H | H | 1 | CN | H | 2-Cl | 1 | O | O | CH$_3$ |
| 769 | C1 | 4-CH$_3$ | H | H | 1 | NO$_2$ | H | 2-Cl | 1 | O | O | CH$_3$ |
| 770 | C1 | 4-CH$_3$ | H | H | 1 | NH$_2$ | H | 2-Cl | 1 | O | O | CH$_3$ |
| 771 | C1 | 4-CH$_3$ | H | H | 1 | NHCH$_3$ | H | 2-Cl | 1 | O | O | CH$_3$ |
| 772 | C1 | 4-CH$_3$ | H | H | 1 | N(CH$_3$)$_2$ | H | 2-Cl | 1 | O | O | CH$_3$ |
| 773 | C1 | 4-CH$_3$ | H | H | 1 | CH$_3$ | CH$_3$ | 2-Cl | 1 | O | O | CH$_3$ |
| 774 | C1 | 4-CH$_3$ | H | H | 1 | CH$_3$ | Et | 2-Cl | 1 | O | O | CH$_3$ |
| 775 | C1 | 4-CH$_3$ | H | H | 1 | CH$_3$ | CH$_3$CO | 2-Cl | 1 | O | O | CH$_3$ |
| 776 | C1 | 4-CH$_3$ | H | H | 1 | CH$_3$ | CH$_3$CH$_2$CO | 2-Cl | 1 | O | O | CH$_3$ |
| 777 | C1 | 4-CH$_3$ | H | H | 1 | CH$_3$ | PhCO | 2-Cl | 1 | O | O | CH$_3$ |
| 778 | C1 | 4-CH$_3$ | H | H | 1 | CH$_3$ | 4-Cl-PhCO | 2-Cl | 1 | O | O | CH$_3$ |
| 779 | C1 | 4-CH$_3$ | H | H | 1 | CH$_3$ | PhCH$_2$CO | 2-Cl | 1 | O | O | CH$_3$ |
| 780 | C1 | 4-CH$_3$ | H | H | 1 | CH$_3$ | CHO | 2-Cl | 1 | O | O | CH$_3$ |
| 781 | C1 | 4-CH$_3$ | H | H | 1 | CH$_3$ | CH$_3$OCH$_2$ | 2-Cl | 1 | O | O | CH$_3$ |
| 782 | C1 | 4-CH$_3$ | H | H | 1 | CH$_3$ | CH$_3$CH(OCH$_3$) | 2-Cl | 1 | O | O | CH$_3$ |
| 783 | C1 | 4-CH$_3$ | H | H | 1 | CH$_3$ | CH$_3$SO$_2$ | 2-Cl | 1 | O | O | CH$_3$ |
| 784 | C1 | 4-CH$_3$ | H | H | 1 | CH$_3$ | PhSO$_2$ | 2-Cl | 1 | O | O | CH$_3$ |
| 785 | C1 | 4-CH$_3$ | H | H | 1 | CH$_3$ | 4-CH$_3$-PhSO$_2$ | 2-Cl | 1 | O | O | CH$_3$ |
| 786 | C1 | 4-CH$_3$ | H | H | 1 | CH$_3$ | H | 2-Cl | 1 | S | O | CH$_3$ |
| 787 | C1 | 4-CH$_3$ | H | H | 1 | CH$_3$ | H | 2-Cl | 1 | O | S | CH$_3$ |

TABLE 14

| | | | | | | | | | | | | |
|---|---|---|---|---|---|---|---|---|---|---|---|---|
| 788 | C1 | 4-CH$_3$ | H | H | 1 | CH$_3$ | H | 2-Cl | 1 | O | — | CH$_3$ |
| 789 | C1 | 4-CH$_3$ | H | H | 1 | CH$_3$ | H | 2-Cl | 1 | O | NH | CH$_3$ |
| 790 | C1 | 4-CH$_3$ | H | H | 1 | CH$_3$ | H | 2-Cl | 1 | O | NCH$_3$ | CH$_3$ |
| 791 | C1 | 4-CH$_3$ | H | H | 1 | CH$_3$ | H | 2-Cl | 1 | O | O | H |
| 792 | C1 | 4-CH$_3$ | H | H | 1 | CH$_3$ | H | 2-Cl | 1 | O | O | Et |
| 793 | C1 | 4-CH$_3$ | H | H | 1 | CH$_3$ | H | 2-Cl | 1 | O | O | n-Pr |
| 794 | C1 | 4-CH$_3$ | H | H | 1 | CH$_3$ | H | 2-Cl | 1 | O | O | CH$_2$CH=CH$_2$ |
| 795 | C1 | 4-CH$_3$ | H | H | 1 | CH$_3$ | H | 2-Cl | 1 | O | O | CH=CH$_2$ |
| 796 | C1 | 4-CH$_3$ | H | H | 1 | CH$_3$ | H | 2-Cl | 1 | O | O | Propargyl |
| 797 | C1 | 4-CH$_3$ | H | H | 1 | CH$_3$ | H | 2-Cl | 1 | O | O | ethynyl |
| 798 | C1 | 4-CH$_3$ | H | H | 1 | CH$_3$ | H | 2-Cl | 1 | O | O | CF$_3$ |
| 799 | C1 | 4-CH$_3$ | H | H | 1 | CH$_3$ | H | 2-Cl | 1 | O | O | CH$_2$CF$_3$ |
| 800 | C1 | 4-CH$_3$ | H | H | 1 | CH$_3$ | H | 2-Cl | 1 | O | O | CF$_2$CF$_3$ |
| 801 | C1 | 4-CH$_3$ | H | H | 1 | CH$_3$ | H | 2-Cl | 1 | O | O | CF$_2$CF$_2$H |
| 802 | C1 | 4-CH$_3$ | H | H | 1 | CH$_3$ | H | 2-Cl | 1 | O | O | CH$_2$CH=CHCl |
| 803 | C1 | 4-CH$_3$ | H | H | 1 | CH$_3$ | H | 2-Cl | 1 | O | O | 3-Iodo-Propargy |
| 804 | C1 | 4-CH$_3$ | H | H | 1 | CH$_3$ | H | 2-Cl | 1 | O | O | c-Pr |
| 805 | C1 | 4-CH$_3$ | H | H | 1 | CH$_3$ | H | 2-Cl | 1 | O | O | O-Hex |
| 806 | C1 | 4-CH$_3$ | H | H | 1 | CH$_3$ | H | 2-Cl | 1 | O | O | 2-CH$_3$-c-Pr |
| 807 | C1 | — | H | H | 1 | CH$_3$ | H | 2-CH$_3$ | 1 | O | O | CH$_3$ |
| 808 | C1 | 4-CH$_3$ | H | H | 1 | CH$_3$ | H | 2-CH$_3$ | 1 | O | O | CH$_3$ |
| 809 | C1 | 4-Et | H | H | 1 | CH$_3$ | H | 2-CH$_3$ | 1 | O | O | CH$_3$ |
| 810 | C1 | 4-CF$_3$ | H | H | 1 | CH$_3$ | H | 2-CH$_3$ | 1 | O | O | CH$_3$ |
| 811 | C1 | 4-F | H | H | 1 | CH$_3$ | H | 2-CH$_3$ | 1 | O | O | CH$_3$ |
| 812 | C1 | 4-Cl | H | H | 1 | CH$_3$ | H | 2-CH$_3$ | 1 | O | O | CH$_3$ |
| 813 | C1 | 4-OCH$_3$ | H | H | 1 | CH$_3$ | H | 2-CH$_3$ | 1 | O | O | CH$_3$ |
| 814 | C1 | 4-OEt | H | H | 1 | CH$_3$ | H | 2-CH$_3$ | 1 | O | O | CH$_3$ |
| 815 | C1 | 4-OCF$_3$ | H | H | 1 | CH$_3$ | H | 2-CH$_3$ | 1 | O | O | CH$_3$ |
| 816 | C1 | 5-CH$_3$ | H | H | 1 | CH$_3$ | H | 2-CH$_3$ | 1 | O | O | CH$_3$ |
| 817 | C1 | 5-Et | H | H | 1 | CH$_3$ | H | 2-CH$_3$ | 1 | O | O | CH$_3$ |
| 818 | C1 | 5-CF$_3$ | H | H | 1 | CH$_3$ | H | 2-CH$_3$ | 1 | O | O | CH$_3$ |
| 819 | C1 | 5-F | H | H | 1 | CH$_3$ | H | 2-CH$_3$ | 1 | O | O | CH$_3$ |
| 820 | C1 | 5-Cl | H | H | 1 | CH$_3$ | H | 2-CH$_3$ | 1 | O | O | CH$_3$ |
| 821 | C1 | 5-OCH$_3$ | H | H | 1 | CH$_3$ | H | 2-CH$_3$ | 1 | O | O | CH$_3$ |
| 822 | C1 | 5-OEt | H | H | 1 | CH$_3$ | H | 2-CH$_3$ | 1 | O | O | CH$_3$ |
| 823 | C1 | 5-OCF$_3$ | H | H | 1 | CH$_3$ | H | 2-CH$_3$ | 1 | O | O | CH$_3$ |
| 824 | C1 | 4,5-diCH$_3$ | H | H | 1 | CH$_3$ | H | 2-CH$_3$ | 1 | O | O | CH$_3$ |
| 825 | C1 | 4-Et-5-CH$_3$ | H | H | 1 | CH$_3$ | H | 2-CH$_3$ | 1 | O | O | CH$_3$ |
| 826 | C1 | 4-CF$_3$-5-F | H | H | 1 | CH$_3$ | H | 2-CH$_3$ | 1 | O | O | CH$_3$ |
| 827 | C1 | 4,5-diF | H | H | 1 | CH$_3$ | H | 2-CH$_3$ | 1 | O | O | CH$_3$ |
| 828 | C1 | 4-Cl-5-F | H | H | 1 | CH$_3$ | H | 2-CH$_3$ | 1 | O | O | CH$_3$ |
| 829 | C1 | 4,5-diOCH$_3$ | H | H | 1 | CH$_3$ | H | 2-CH$_3$ | 1 | O | O | CH$_3$ |
| 830 | C1 | 4-OEt-5-CH$_3$ | H | H | 1 | CH$_3$ | H | 2-CH$_3$ | 1 | O | O | CH$_3$ |
| 831 | C1 | 4-OCF$_3$-5-F | H | H | 1 | CH$_3$ | H | 2-CH$_3$ | 1 | O | O | CH$_3$ |
| 832 | C1 | 4-CH$_3$ | H | CH$_3$ | 1 | CH$_3$ | H | 2-CH$_3$ | 1 | O | O | CH$_3$ |
| 833 | C1 | 4-Et | H | CH$_3$ | 1 | CH$_3$ | H | 2-CH$_3$ | 1 | O | O | CH$_3$ |
| 834 | C1 | 4-CH$_3$ | H | Et | 1 | CH$_3$ | H | 2-CH$_3$ | 1 | O | O | CH$_3$ |
| 835 | C1 | 4-CH$_3$ | H | I-Pr | 1 | CH$_3$ | H | 2-CH$_3$ | 1 | O | O | CH$_3$ |
| 836 | C1 | 4-CH$_3$ | CH$_3$ | Et | 1 | CH$_3$ | H | 2-CH$_3$ | 1 | O | O | CH$_3$ |
| 837 | C1 | 4-CH$_3$ | H | F | 1 | CH$_3$ | H | 2-CH$_3$ | 1 | O | O | CH$_3$ |

TABLE 14-continued

| | | | | | | | | | | | | |
|---|---|---|---|---|---|---|---|---|---|---|---|---|
| 838 | C1 | 4-CH₃ | F | F | 1 | CH₃ | H | 2-CH₃ | 1 | O | O | CH₃ |
| 839 | C1 | 4-CH₃ | H | CF₃ | 1 | CH₃ | H | 2-CH₃ | 1 | O | O | CH₃ |
| 840 | C1 | 4-CH₃ | H | c-Pr | 1 | CH₃ | H | 2-CH₃ | 1 | O | O | CH₃ |
| 841 | C1 | 4-CH₃ | —CH2CH2— | | 1 | CH₃ | H | 2-CH₃ | 1 | O | O | CH₃ |
| 842 | C1 | 4-CH₃ | —CH2CH2CH2— | | 1 | CH₃ | H | 2-CH₃ | 1 | O | O | CH₃ |
| 843 | C1 | 4-CH₃ | —CH2CH(CH3)— | | 1 | CH₃ | H | 2-CH₃ | 1 | O | O | CH₃ |
| 844 | C1 | 4-CH₃ | —CH2C(CH3)2— | | 1 | CH₃ | H | 2-CH₃ | 1 | O | O | CH₃ |
| 845 | C1 | 4-CH₃ | H | H | 1 | H | H | 2-CH₃ | 1 | O | O | CH₃ |
| 846 | C1 | 4-CH₃ | H | H | 1 | Et | H | 2-CH₃ | 1 | O | O | CH₃ |
| 847 | C1 | 4-CH₃ | H | H | 1 | c-Pr | H | 2-CH₃ | 1 | O | O | CH₃ |

TABLE 15

| | | | | | | | | | | | | |
|---|---|---|---|---|---|---|---|---|---|---|---|---|
| 848 | C1 | 4-CH₃ | H | H | 1 | CH=CH₂ | H | 2-CH₃ | 1 | O | O | CH₃ |
| 849 | C1 | 4-CH₃ | H | H | 1 | CH₂CH=CH₂ | H | 2-CH₃ | 1 | O | O | CH₃ |
| 850 | C1 | 4-CH₃ | H | H | 1 | ethynyl | H | 2-CH₃ | 1 | O | O | CH₃ |
| 851 | C1 | 4-CH₃ | H | H | 1 | Propargyl | H | 2-CH₃ | 1 | O | O | CH₃ |
| 852 | C1 | 4-CH₃ | H | H | 1 | CF₃ | H | 2-CH₃ | 1 | O | O | CH₃ |
| 853 | C1 | 4-CH₃ | H | H | 1 | CH=CHCl | H | 2-CH₃ | 1 | O | O | CH₃ |
| 854 | C1 | 4-CH₃ | H | H | 1 | 3,3,2-tri-Iodo-allyl | H | 2-CH₃ | 1 | O | O | CH₃ |
| 855 | C1 | 4-CH₃ | H | H | 1 | 3-Iodopropargyl | H | 2-CH₃ | 1 | O | O | CH₃ |
| 856 | C1 | 4-CH₃ | H | H | 1 | CN | H | 2-CH₃ | 1 | O | O | CH₃ |
| 857 | C1 | 4-CF₃ | H | H | 1 | CN | H | 2-CH₃ | 1 | O | O | CH₃ |
| 858 | C1 | 4-CH₃ | H | H | 1 | NO₂ | H | 2-CH₃ | 1 | O | O | CH₃ |
| 859 | C1 | 4-CH₃ | H | H | 1 | NH₂ | H | 2-CH₃ | 1 | O | O | CH₃ |
| 860 | C1 | 4-CH₃ | H | H | 1 | NHCH₃ | H | 2-CH₃ | 1 | O | O | CH₃ |
| 861 | C1 | 4-CH₃ | H | H | 1 | N(CH₃)₂ | H | 2-CH₃ | 1 | O | O | CH₃ |
| 862 | C1 | 4-CH₃ | H | H | 1 | CH₃ | CH₃ | 2-CH₃ | 1 | O | O | CH₃ |
| 863 | C1 | 4-CH₃ | H | H | 1 | CH₃ | Et | 2-CH₃ | 1 | O | O | CH₃ |
| 864 | C1 | 4-CH₃ | H | H | 1 | CH₃ | CH₃CO | 2-CH₃ | 1 | O | O | CH₃ |
| 865 | C1 | 4-CH₃ | H | H | 1 | CH₃ | CH₃CH₂CO | 2-CH₃ | 1 | O | O | CH₃ |
| 866 | C1 | 4-CH₃ | H | H | 1 | CH₃ | PhCO | 2-CH₃ | 1 | O | O | CH₃ |
| 867 | C1 | 4-CH₃ | H | H | 1 | CH₃ | 4-Cl-PhCO | 2-CH₃ | 1 | O | O | CH₃ |
| 868 | C1 | 4-CH₃ | H | H | 1 | CH₃ | PhCH₂CO | 2-CH₃ | 1 | O | O | CH₃ |
| 869 | C1 | 4-CH₃ | H | H | 1 | CH₃ | CHO | 2-CH₃ | 1 | O | O | CH₃ |
| 870 | C1 | 4-CH₃ | H | H | 1 | CH₃ | CH₃OCH₂ | 2-CH₃ | 1 | O | O | CH₃ |
| 871 | C1 | 4-CH₃ | H | H | 1 | CH₃ | CH₃CH(OCH₃) | 2-CH₃ | 1 | O | O | CH₃ |
| 872 | C1 | 4-CH₃ | H | H | 1 | CH₃ | CH₃SO₂ | 2-CH₃ | 1 | O | O | CH₃ |
| 873 | C1 | 4-CH₃ | H | H | 1 | CH₃ | PhSO₂ | 2-CH₃ | 1 | O | O | CH₃ |
| 874 | C1 | 4-CH₃ | H | H | 1 | CH₃ | 4-CH₃-PhSO₂ | 2-CH₃ | 1 | O | O | CH₃ |
| 875 | C1 | 4-CH₃ | H | H | 1 | CH₃ | H | 2-CH₃ | 1 | S | O | CH₃ |
| 876 | C1 | 4-CH₃ | H | H | 1 | CH₃ | H | 2-CH₃ | 1 | O | S | CH₃ |
| 877 | C1 | 4-CH₃ | H | H | 1 | CH₃ | H | 2-CH₃ | 1 | O | — | CH₃ |
| 878 | C1 | 4-CH₃ | H | H | 1 | CH₃ | H | 2-CH₃ | 1 | O | NH | CH₃ |
| 879 | C1 | 4-CH₃ | H | H | 1 | CH₃ | H | 2-CH₃ | 1 | O | NCH₃ | CH₃ |
| 880 | C1 | 4-CH₃ | H | H | 1 | CH₃ | H | 2-CH₃ | 1 | O | O | H |
| 881 | C1 | 4-CH₃ | H | H | 1 | CH₃ | H | 2-CH₃ | 1 | O | O | Et |
| 882 | C1 | 4-CH₃ | H | H | 1 | CH₃ | H | 2-CH₃ | 1 | O | O | n-Pr |
| 883 | C1 | 4-CH₃ | H | H | 1 | CH₃ | H | 2-CH₃ | 1 | O | O | CH₂CH=CH₂ |
| 884 | C1 | 4-CH₃ | H | H | 1 | CH₃ | H | 2-CH₃ | 1 | O | O | CH=CH₂ |
| 885 | C1 | 4-CH₃ | H | H | 1 | CH₃ | H | 2-CH₃ | 1 | O | O | Propargyl |
| 886 | C1 | 4-CH₃ | H | H | 1 | CH₃ | H | 2-CH₃ | 1 | O | O | ethynyl |
| 887 | C1 | 4-CH₃ | H | H | 1 | CH₃ | H | 2-CH₃ | 1 | O | O | CF₃ |
| 888 | C1 | 4-CH₃ | H | H | 1 | CH₃ | H | 2-CH₃ | 1 | O | O | CH₂CF₃ |
| 889 | C1 | 4-CH₃ | H | H | 1 | CH₃ | H | 2-CH₃ | 1 | O | O | CF₂CF₃ |
| 890 | C1 | 4-CH₃ | H | H | 1 | CH₃ | H | 2-CH₃ | 1 | O | O | CF₂CF₂H |
| 891 | C1 | 4-CH₃ | H | H | 1 | CH₃ | H | 2-CH₃ | 1 | O | O | CH₂CH=CHCl |
| 892 | C1 | 4-CH₃ | H | H | 1 | CH₃ | H | 2-CH₃ | 1 | O | O | 3-Iodo-Propargyl |
| 893 | C1 | 4-CH₃ | H | H | 1 | CH₃ | H | 2-CH₃ | 1 | O | O | c-Pr |
| 894 | C1 | 4-CH₃ | H | H | 1 | CH₃ | H | 2-CH₃ | 1 | O | O | c-Hex |
| 895 | C1 | 4-CH₃ | H | H | 1 | CH₃ | H | 2-CH₃ | 1 | O | O | 2-CH₃-c-Pr |
| 896 | C2 | — | H | H | 1 | CH₃ | H | — | 0 | O | O | CH₃ |
| 897 | C2 | — | H | H | 1 | CH₃ | H | 2-Cl | 1 | O | O | CH₃ |
| 898 | C2 | 2-CH₃ | H | H | 1 | CH₃ | H | 2-Cl | 1 | O | O | CH₃ |
| 899 | C2 | 2-Et | H | H | 1 | CH₃ | H | 2-Cl | 1 | O | O | CH₃ |
| 900 | C2 | 2-CF₃ | H | H | 1 | CH₃ | H | 2-Cl | 1 | O | O | CH₃ |
| 901 | C2 | 2-F | H | H | 1 | CH₃ | H | 2-Cl | 1 | O | O | CH₃ |
| 902 | C2 | 2-Cl | H | H | 1 | CH₃ | H | 2-Cl | 1 | O | O | CH₃ |
| 903 | C2 | 2-OCH₃ | H | H | 1 | CH₃ | H | 2-Cl | 1 | O | O | CH₃ |
| 904 | C2 | 2-OEt | H | H | 1 | CH₃ | H | 2-Cl | 1 | O | O | CH₃ |
| 905 | C2 | 2-OCF₃ | H | H | 1 | CH₃ | H | 2-Cl | 1 | O | O | CH₃ |
| 906 | C2 | 5-CH₃ | H | H | 1 | CH₃ | H | 2-Cl | 1 | O | O | CH₃ |
| 907 | C2 | 5-Et | H | H | 1 | CH₃ | H | 2-Cl | 1 | O | O | CH₃ |
| 908 | C2 | 5-CF₃ | H | H | 1 | CH₃ | H | 2-Cl | 1 | O | O | CH₃ |
| 909 | C2 | 5-F | H | H | 1 | CH₃ | H | 2-Cl | 1 | O | O | CH₃ |

TABLE 16

| No. | | | | | | | | | | | | |
|---|---|---|---|---|---|---|---|---|---|---|---|---|
| 910 | C2 | 5-Cl | H | H | 1 | CH$_3$ | H | 2-Cl | 1 | O | O | CH$_3$ |
| 911 | C2 | 5-OCH$_3$ | H | H | 1 | CH$_3$ | H | 2-Cl | 1 | O | O | CH$_3$ |
| 912 | C2 | 5-OEt | H | H | 1 | CH$_3$ | H | 2-Cl | 1 | O | O | CH$_3$ |
| 913 | C2 | 5-OCF$_3$ | H | H | 1 | CH$_3$ | H | 2-Cl | 1 | O | O | CH$_3$ |
| 914 | C2 | 2,5-diCH$_3$ | H | H | 1 | CH$_3$ | H | 2-Cl | 1 | O | O | CH$_3$ |
| 915 | C2 | 2-Et-5-CH$_3$ | H | H | 1 | CH$_3$ | H | 2-Cl | 1 | O | O | CH$_3$ |
| 916 | C2 | 2-CF$_3$-5-F | H | H | 1 | CH$_3$ | H | 2-Cl | 1 | O | O | CH$_3$ |
| 917 | C2 | 2,5-diF | H | H | 1 | CH$_3$ | H | 2-Cl | 1 | O | O | CH$_3$ |
| 918 | C2 | 2-Cl-5-F | H | H | 1 | CH$_3$ | H | 2-Cl | 1 | O | O | CH$_3$ |
| 919 | C2 | 2,5-diOCH$_3$ | H | H | 1 | CH$_3$ | H | 2-Cl | 1 | O | O | CH$_3$ |
| 920 | C2 | 2-OEt-5-CH$_3$ | H | H | 1 | CH$_3$ | H | 2-Cl | 1 | O | O | CH$_3$ |
| 921 | C2 | 2-OCF$_3$-5-F | H | H | 1 | CH$_3$ | H | 2-Cl | 1 | O | O | CH$_3$ |
| 922 | C2 | 2-CH$_3$ | H | CH$_3$ | 1 | CH$_3$ | H | 2-Cl | 1 | O | O | CH$_3$ |
| 923 | C2 | 2-Et | H | CH$_3$ | 1 | CH$_3$ | H | 2-Cl | 1 | O | O | CH$_3$ |
| 924 | C2 | 2-CH$_3$ | H | Et | 1 | CH$_3$ | H | 2-Cl | 1 | O | O | CH$_3$ |
| 925 | C2 | 2-CH$_3$ | H | i-Pr | 1 | CH$_3$ | H | 2-Cl | 1 | O | O | CH$_3$ |
| 926 | C2 | 2-CH$_3$ | CH$_3$ | Et | 1 | CH$_3$ | H | 2-Cl | 1 | O | O | CH$_3$ |
| 927 | C2 | 2-CH$_3$ | H | F | 1 | CH$_3$ | H | 2-Cl | 1 | O | O | CH$_3$ |
| 928 | C2 | 2-CH$_3$ | F | F | 1 | CH$_3$ | H | 2-Cl | 1 | O | O | CH$_3$ |
| 929 | C2 | 2-CH$_3$ | H | CF$_3$ | 1 | CH$_3$ | H | 2-Cl | 1 | O | O | CH$_3$ |
| 930 | C2 | 2-CH$_3$ | H | c-Pr | 1 | CH$_3$ | H | 2-Cl | 1 | O | O | CH$_3$ |
| 931 | C2 | 2-CH$_3$ | —CH2CH2— | | 1 | CH$_3$ | H | 2-Cl | 1 | O | O | CH$_3$ |
| 932 | C2 | 2-CH$_3$ | —CH2CH2CH2— | | 1 | CH$_3$ | H | 2-Cl | 1 | O | O | CH$_3$ |
| 933 | C2 | 2-CH$_3$ | —CH2CH(CH3)— | | 1 | CH$_3$ | H | 2-Cl | 1 | O | O | CH$_3$ |
| 934 | C2 | 2-CH$_3$ | —CH2C(CH3)2— | | 1 | CH$_3$ | H | 2-Cl | 1 | O | O | CH$_3$ |
| 935 | C2 | 2-CH$_3$ | H | H | 1 | H | H | 2-Cl | 1 | O | O | CH$_3$ |
| 936 | C2 | 2-CH$_3$ | H | H | 1 | Et | H | 2-Cl | 1 | O | O | CH$_3$ |
| 937 | C2 | 2-CH$_3$ | H | H | 1 | c-Pr | H | 2-Cl | 1 | O | O | CH$_3$ |
| 938 | C2 | 2-CH$_3$ | H | H | 1 | CH=CH$_2$ | H | 2-Cl | 1 | O | O | CH$_3$ |
| 939 | C2 | 2-CH$_3$ | H | H | 1 | CH$_2$CH=CH$_2$ | H | 2-Cl | 1 | O | O | CH$_3$ |
| 940 | C2 | 2-CH$_3$ | H | H | 1 | ethynyl | H | 2-Cl | 1 | O | O | CH$_3$ |
| 941 | C2 | 2-CH$_3$ | H | H | 1 | Propargyl | H | 2-Cl | 1 | O | O | CH$_3$ |
| 942 | C2 | 2-CH$_3$ | H | H | 1 | CF$_3$ | H | 2-Cl | 1 | O | O | CH$_3$ |
| 943 | C2 | 2-CH$_3$ | H | H | 1 | CH=CHCl | H | 2-Cl | 1 | O | O | CH$_3$ |
| 944 | C2 | 2-CH$_3$ | H | H | 1 | 3,3,2-tri-Iodo-allyl | H | 2-Cl | 1 | O | O | CH$_3$ |
| 945 | C2 | 2-CH$_3$ | H | H | 1 | 3-Iodopropargyl | H | 2-Cl | 1 | O | O | CH$_3$ |
| 946 | C2 | 2-CH$_3$ | H | H | 1 | CN | H | 2-Cl | 1 | O | O | CH$_3$ |
| 947 | C2 | 2-CF$_3$ | H | H | 1 | CN | H | 2-Cl | 1 | O | O | CH$_3$ |
| 948 | C2 | 2-CH$_3$ | H | H | 1 | NO$_2$ | H | 2-Cl | 1 | O | O | CH$_3$ |
| 949 | C2 | 2-CH$_3$ | H | H | 1 | NH$_2$ | H | 2-Cl | 1 | O | O | CH$_3$ |
| 950 | C2 | 2-CH$_3$ | H | H | 1 | NHCH$_3$ | H | 2-Cl | 1 | O | O | CH$_3$ |
| 951 | C2 | 2-CH$_3$ | H | H | 1 | N(CH$_3$)$_2$ | H | 2-Cl | 1 | O | O | CH$_3$ |
| 952 | C2 | 2-CH$_3$ | H | H | 1 | CH$_3$ | CH$_3$ | 2-Cl | 1 | O | O | CH$_3$ |
| 953 | C2 | 2-CH$_3$ | H | H | 1 | CH$_3$ | Et | 2-Cl | 1 | O | O | CH$_3$ |
| 954 | C2 | 2-CH$_3$ | H | H | 1 | CH$_3$ | CH$_3$CO | 2-Cl | 1 | O | O | CH$_3$ |
| 955 | C2 | 2-CH$_3$ | H | H | 1 | CH$_3$ | CH$_3$CH$_2$CO | 2-Cl | 1 | O | O | CH$_3$ |
| 956 | C2 | 2-CH$_3$ | H | H | 1 | CH$_3$ | PhCO | 2-Cl | 1 | O | O | CH$_3$ |
| 957 | C2 | 2-CH$_3$ | H | H | 1 | CH$_3$ | 4-Cl-PhCO | 2-Cl | 1 | O | O | CH$_3$ |
| 958 | C2 | 2-CH$_3$ | H | H | 1 | CH$_3$ | PhCH$_2$CO | 2-Cl | 1 | O | O | CH$_3$ |
| 959 | C2 | 2-CH$_3$ | H | H | 1 | CH$_3$ | CHO | 2-Cl | 1 | O | O | CH$_3$ |
| 960 | C2 | 2-CH$_3$ | H | H | 1 | CH$_3$ | CH$_3$OCH$_2$ | 2-Cl | 1 | O | O | CH$_3$ |
| 961 | C2 | 2-CH$_3$ | H | H | 1 | CH$_3$ | CH$_3$CH(OCH$_3$) | 2-Cl | 1 | O | O | CH$_3$ |
| 962 | C2 | 2-CH$_3$ | H | H | 1 | CH$_3$ | CH$_3$SO$_2$ | 2-Cl | 1 | O | O | CH$_3$ |
| 963 | C2 | 2-CH$_3$ | H | H | 1 | CH$_3$ | PhSO$_2$ | 2-Cl | 1 | O | O | CH$_3$ |
| 964 | C2 | 2-CH$_3$ | H | H | 1 | CH$_3$ | 4-CH$_3$-PhSO$_2$ | 2-Cl | 1 | O | O | CH$_3$ |
| 965 | C2 | 2-CH$_3$ | H | H | 1 | CH$_3$ | H | 2-Cl | 1 | S | O | CH$_3$ |
| 966 | C2 | 2-CH$_3$ | H | H | 1 | CH$_3$ | H | 2-Cl | 1 | O | S | CH$_3$ |
| 967 | C2 | 2-CH$_3$ | H | H | 1 | CH$_3$ | H | 2-Cl | 1 | O | — | CH$_3$ |
| 968 | C2 | 2-CH$_3$ | H | H | 1 | CH$_3$ | H | 2-Cl | 1 | O | NH | CH$_3$ |
| 969 | C2 | 2-CH$_3$ | H | H | 1 | CH$_3$ | H | 2-Cl | 1 | O | NCH$_3$ | CH$_3$ |
| 970 | C2 | 2-CH$_3$ | H | H | 1 | CH$_3$ | H | 2-Cl | 1 | O | O | H |
| 971 | C2 | 2-CH$_3$ | H | H | 1 | CH$_3$ | H | 2-Cl | 1 | O | O | Et |

TABLE 17

| No. | | | | | | | | | | | | |
|---|---|---|---|---|---|---|---|---|---|---|---|---|
| 972 | C2 | 2-CH$_3$ | H | H | 1 | CH$_3$ | H | 2-Cl | 1 | O | O | n-Pr |
| 973 | C2 | 2-CH$_3$ | H | H | 1 | CH$_3$ | H | 2-Cl | 1 | O | O | CH$_2$CH=CH$_2$ |
| 974 | C2 | 2-CH$_3$ | H | H | 1 | CH$_3$ | H | 2-Cl | 1 | O | O | CH=CH$_2$ |
| 975 | C2 | 2-CH$_3$ | H | H | 1 | CH$_3$ | H | 2-Cl | 1 | O | O | Propargyl |
| 976 | C2 | 2-CH$_3$ | H | H | 1 | CH$_3$ | H | 2-Cl | 1 | O | O | ethynyl |
| 977 | C2 | 2-CH$_3$ | H | H | 1 | CH$_3$ | H | 2-Cl | 1 | O | O | CF$_3$ |
| 978 | C2 | 2-CH$_3$ | H | H | 1 | CH$_3$ | H | 2-Cl | 1 | O | O | CH$_2$CF$_3$ |
| 979 | C2 | 2-CF$_3$ | H | H | 1 | CH$_3$ | H | 2-Cl | 1 | O | O | CF$_2$CF$_3$ |
| 980 | C2 | 2-CH$_3$ | H | H | 1 | CH$_3$ | H | 2-Cl | 1 | O | O | CF$_2$CF$_2$H |
| 981 | C2 | 2-CH$_3$ | H | H | 1 | CH$_3$ | H | 2-Cl | 1 | O | O | CH$_2$CH=CHCl |
| 982 | C2 | 2-CH$_3$ | H | H | 1 | CH$_3$ | H | 2-Cl | 1 | O | O | 3-Iodo-Propargyl |
| 983 | C2 | 2-CH$_3$ | H | H | 1 | CH$_3$ | H | 2-Cl | 1 | O | O | c-Pr |

TABLE 17-continued

| No. | Type | A | B | C | n | D | E | F | m | X | Y | Z |
|---|---|---|---|---|---|---|---|---|---|---|---|---|
| 984 | C2 | 2-CH$_3$ | H | H | 1 | CH$_3$ | H | 2-Cl | 1 | O | O | c-Hex |
| 985 | C2 | 2-CH$_3$ | H | H | 1 | CH$_3$ | H | 2-Cl | 1 | O | O | 2-CH$_3$-c-Pr |
| 986 | C2 | — | H | H | 1 | CH$_3$ | H | 2-CH$_3$ | 1 | O | O | CH$_3$ |
| 987 | C2 | 2-CH$_3$ | H | H | 1 | CH$_3$ | H | 2-CH$_3$ | 1 | O | O | CH$_3$ |
| 988 | C2 | 2-Et | H | H | 1 | CH$_3$ | H | 2-CH$_3$ | 1 | O | O | CH$_3$ |
| 989 | C2 | 2-CF$_3$ | H | H | 1 | CH$_3$ | H | 2-CH$_3$ | 1 | O | O | CH$_3$ |
| 990 | C2 | 2-F | H | H | 1 | CH$_3$ | H | 2-CH$_3$ | 1 | O | O | CH$_3$ |
| 991 | C2 | 2-Cl | H | H | 1 | CH$_3$ | H | 2-CH$_3$ | 1 | O | O | CH$_3$ |
| 992 | C2 | 2-OCH$_3$ | H | H | 1 | CH$_3$ | H | 2-CH$_3$ | 1 | O | O | CH$_3$ |
| 993 | C2 | 2-OEt | H | H | 1 | CH$_3$ | H | 2-CH$_3$ | 1 | O | O | CH$_3$ |
| 994 | C2 | 2-OCF$_3$ | H | H | 1 | CH$_3$ | H | 2-CH$_3$ | 1 | O | O | CH$_3$ |
| 995 | C2 | 5-CH$_3$ | H | H | 1 | CH$_3$ | H | 2-CH$_3$ | 1 | O | O | CH$_3$ |
| 996 | C2 | 5-Et | H | H | 1 | CH$_3$ | H | 2-CH$_3$ | 1 | O | O | CH$_3$ |
| 997 | C2 | 5-CF$_3$ | H | H | 1 | CH$_3$ | H | 2-CH$_3$ | 1 | O | O | CH$_3$ |
| 998 | C2 | 5-F | H | H | 1 | CH$_3$ | H | 2-CH$_3$ | 1 | O | O | CH$_3$ |
| 999 | C2 | 5-Cl | H | H | 1 | CH$_3$ | H | 2-CH$_3$ | 1 | O | O | CH$_3$ |
| 1000 | C2 | 5-OCH$_3$ | H | H | 1 | CH$_3$ | H | 2-CH$_3$ | 1 | O | O | CH$_3$ |
| 1001 | C2 | 5-OEt | H | H | 1 | CH$_3$ | H | 2-CH$_3$ | 1 | O | O | CH$_3$ |
| 1002 | C2 | 5-OCF$_3$ | H | H | 1 | CH$_3$ | H | 2-CH$_3$ | 1 | O | O | CH$_3$ |
| 1003 | C2 | 2,5-diCH$_3$ | H | H | 1 | CH$_3$ | H | 2-CH$_3$ | 1 | O | O | CH$_3$ |
| 1004 | C2 | 2-Et-5-CH$_3$ | H | H | 1 | CH$_3$ | H | 2-CH$_3$ | 1 | O | O | CH$_3$ |
| 1005 | C2 | 2-CF$_3$-5-F | H | H | 1 | CH$_3$ | H | 2-CH$_3$ | 1 | O | O | CH$_3$ |
| 1006 | C2 | 2,5-diF | H | H | 1 | CH$_3$ | H | 2-CH$_3$ | 1 | O | O | CH$_3$ |
| 1007 | C2 | 2-Cl-5-F | H | H | 1 | CH$_3$ | H | 2-CH$_3$ | 1 | O | O | CH$_3$ |
| 1008 | C2 | 2,5-diOCH$_3$ | H | H | 1 | CH$_3$ | H | 2-CH$_3$ | 1 | O | O | CH$_3$ |
| 1009 | C2 | 2-OEt-5-CH$_3$ | H | H | 1 | CH$_3$ | H | 2-CH$_3$ | 1 | O | O | CH$_3$ |
| 1010 | C2 | 2-OCF$_3$-5-F | H | H | 1 | CH$_3$ | H | 2-CH$_3$ | 1 | O | O | CH$_3$ |
| 1011 | C2 | 2-CH$_3$ | H | CH$_3$ | 1 | CH$_3$ | H | 2-CH$_3$ | 1 | O | O | CH$_3$ |
| 1012 | C2 | 2-Et | H | CH$_3$ | 1 | CH$_3$ | H | 2-CH$_3$ | 1 | O | O | CH$_3$ |
| 1013 | C2 | 2-CH$_3$ | H | Et | 1 | CH$_3$ | H | 2-CH$_3$ | 1 | O | O | CH$_3$ |
| 1014 | C2 | 2-CH$_3$ | H | i-Pr | 1 | CH$_3$ | H | 2-CH$_3$ | 1 | O | O | CH$_3$ |
| 1015 | C2 | 2-CH$_3$ | CH$_3$ | Et | 1 | CH$_3$ | H | 2-CH$_3$ | 1 | O | O | CH$_3$ |
| 1016 | C2 | 2-CH$_3$ | H | F | 1 | CH$_3$ | H | 2-CH$_3$ | 1 | O | O | CH$_3$ |
| 1017 | C2 | 2-CH$_3$ | F | F | 1 | CH$_3$ | H | 2-CH$_3$ | 1 | O | O | CH$_3$ |
| 1018 | C2 | 2-CH$_3$ | H | CF$_3$ | 1 | CH$_3$ | H | 2-CH$_3$ | 1 | O | O | CH$_3$ |
| 1019 | C2 | 2-CH$_3$ | H | c-Pr | 1 | CH$_3$ | H | 2-CH$_3$ | 1 | O | O | CH$_3$ |
| 1020 | C2 | 2-CH$_3$ | —CH2CH2— | | 1 | CH$_3$ | H | 2-CH$_3$ | 1 | O | O | CH$_3$ |
| 1021 | C2 | 2-CH$_3$ | —CH2CH2CH$_2$— | | 1 | CH$_3$ | H | 2-CH$_3$ | 1 | O | O | CH$_3$ |
| 1022 | C2 | 2-CH$_3$ | —CH2CH(CH3)— | | 1 | CH$_3$ | H | 2-CH$_3$ | 1 | O | O | CH$_3$ |
| 1023 | C2 | 2-CH$_3$ | —CH2C(CH3)2— | | 1 | CH$_3$ | H | 2-CH$_3$ | 1 | O | O | CH$_3$ |
| 1024 | C2 | 2-CH$_3$ | H | H | 1 | H | H | 2-CH$_3$ | 1 | O | O | CH$_3$ |
| 1025 | C2 | 2-CH$_3$ | H | H | 1 | Et | H | 2-CH$_3$ | 1 | O | O | CH$_3$ |
| 1026 | C2 | 2-CH$_3$ | H | H | 1 | c-Pr | H | 2-CH$_3$ | 1 | O | O | CH$_3$ |
| 1027 | C2 | 2-CH$_3$ | H | H | 1 | CH=CH$_2$ | H | 2-CH$_3$ | 1 | O | O | CH$_3$ |
| 1028 | C2 | 2-CH$_3$ | H | H | 1 | CH$_2$CH=CH$_2$ | H | 2-CH$_3$ | 1 | O | O | CH$_3$ |
| 1029 | C2 | 2-CH$_3$ | H | H | 1 | ethynyl | H | 2-CH$_3$ | 1 | O | O | CH$_3$ |
| 1030 | C2 | 2-CH$_3$ | H | H | 1 | Propargyl | H | 2-CH$_3$ | 1 | O | O | CH$_3$ |
| 1031 | C2 | 2-CH$_3$ | H | H | 1 | CF$_3$ | H | 2-CH$_3$ | 1 | O | O | CH$_3$ |
| 1032 | C2 | 2-CH$_3$ | H | H | 1 | CH=CHCl | H | 2-CH$_3$ | 1 | O | O | CH$_3$ |
| 1033 | C2 | 2-CH$_3$ | H | H | 1 | 3,3,2-tri-Iodo-allyl | H | 2-CH$_3$ | 1 | O | O | CH$_3$ |

TABLE 18

| No. | Type | A | B | C | n | D | E | F | m | X | Y | Z |
|---|---|---|---|---|---|---|---|---|---|---|---|---|
| 1034 | C2 | 2-CH$_3$ | H | H | 1 | 3-Iodopropargyl | H | 2-CH$_3$ | 1 | O | O | CH$_3$ |
| 1035 | C2 | 2-CH$_3$ | H | H | 1 | CN | H | 2-CH$_3$ | 1 | O | O | CH$_3$ |
| 1036 | C2 | 2-CF$_3$ | H | H | 1 | CN | H | 2-CH$_3$ | 1 | O | O | CH$_3$ |
| 1037 | C2 | 2-CH$_3$ | H | H | 1 | NO$_2$ | H | 2-CH$_3$ | 1 | O | O | CH$_3$ |
| 1038 | C2 | 2-CH$_3$ | H | H | 1 | NH$_2$ | H | 2-CH$_3$ | 1 | O | O | CH$_3$ |
| 1039 | C2 | 2-CH$_3$ | H | H | 1 | NHCH$_3$ | H | 2-CH$_3$ | 1 | O | O | CH$_3$ |
| 1040 | C2 | 2-CH$_3$ | H | H | 1 | N(CH$_3$)$_2$ | H | 2-CH$_3$ | 1 | O | O | CH$_3$ |
| 1041 | C2 | 2-CH$_3$ | H | H | 1 | CH$_3$ | CH$_3$ | 2-CH$_3$ | 1 | O | O | CH$_3$ |
| 1042 | C2 | 2-CH$_3$ | H | H | 1 | CH$_3$ | Et | 2-CH$_3$ | 1 | O | O | CH$_3$ |
| 1043 | C2 | 2-CH$_3$ | H | H | 1 | CH$_3$ | CH$_3$CO | 2-CH$_3$ | 1 | O | O | CH$_3$ |
| 1044 | C2 | 2-CH$_3$ | H | H | 1 | CH$_3$ | CH$_3$CH$_2$CO | 2-CH$_3$ | 1 | O | O | CH$_3$ |
| 1045 | C2 | 2-CH$_3$ | H | H | 1 | CH$_3$ | PhCO | 2-CH$_3$ | 1 | O | O | CH$_3$ |
| 1046 | C2 | 2-CH$_3$ | H | H | 1 | CH$_3$ | 4-Cl-PhCO | 2-CH$_3$ | 1 | O | O | CH$_3$ |
| 1047 | C2 | 2-CH$_3$ | H | H | 1 | CH$_3$ | PhCH$_2$CO | 2-CH$_3$ | 1 | O | O | CH$_3$ |
| 1048 | C2 | 2-CH$_3$ | H | H | 1 | CH$_3$ | CHO | 2-CH$_3$ | 1 | O | O | CH$_3$ |
| 1049 | C2 | 2-CH$_3$ | H | H | 1 | CH$_3$ | CH$_3$OCH$_2$ | 2-CH$_3$ | 1 | O | O | CH$_3$ |
| 1050 | C2 | 2-CH$_3$ | H | H | 1 | CH$_3$ | CH$_3$CH(OCH$_3$) | 2-CH$_3$ | 1 | O | O | CH$_3$ |
| 1051 | C2 | 2-CH$_3$ | H | H | 1 | CH$_3$ | CH$_3$SO$_2$ | 2-CH$_3$ | 1 | O | O | CH$_3$ |
| 1052 | C2 | 2-CH$_3$ | H | H | 1 | CH$_3$ | PhSO$_2$ | 2-CH$_3$ | 1 | O | O | CH$_3$ |
| 1053 | C2 | 2-CH$_3$ | H | H | 1 | CH$_3$ | 4-CH$_3$-PhSO$_2$ | 2-CH$_3$ | 1 | O | O | CH$_3$ |
| 1054 | C2 | 2-CH$_3$ | H | H | 1 | CH$_3$ | H | 2-CH$_3$ | 1 | S | O | CH$_3$ |
| 1055 | C2 | 2-CH$_3$ | H | H | 1 | CH$_3$ | H | 2-CH$_3$ | 1 | O | S | CH$_3$ |
| 1056 | C2 | 2-CH$_3$ | H | H | 1 | CH$_3$ | H | 2-CH$_3$ | 1 | O | — | CH$_3$ |
| 1057 | C2 | 2-CH$_3$ | H | H | 1 | CH$_3$ | H | 2-CH$_3$ | 1 | O | NH | CH$_3$ |

TABLE 18-continued

| | | | | | | | | | | | | |
|---|---|---|---|---|---|---|---|---|---|---|---|---|
| 1058 | C2 | 2-CH$_3$ | H | H | 1 | CH$_3$ | H | 2-CH$_3$ | 1 | O | NCH$_3$ | CH$_3$ |
| 1059 | C2 | 2-CH$_3$ | H | H | 1 | CH$_3$ | H | 2-CH$_3$ | 1 | O | O | H |
| 1060 | C2 | 2-CH$_3$ | H | H | 1 | CH$_3$ | H | 2-CH$_3$ | 1 | O | O | Et |
| 1061 | C2 | 2-CH$_3$ | H | H | 1 | CH$_3$ | H | 2-CH$_3$ | 1 | O | O | n-Pr |
| 1062 | C2 | 2-CH$_3$ | H | H | 1 | CH$_3$ | H | 2-CH$_3$ | 1 | O | O | CH$_2$CH=CH$_2$ |
| 1063 | C2 | 2-CH$_3$ | H | H | 1 | CH$_3$ | H | 2-CH$_3$ | 1 | O | O | CH=CH$_2$ |
| 1064 | C2 | 2-CH$_3$ | H | H | 1 | CH$_3$ | H | 2-CH$_3$ | 1 | O | O | Propargyl |
| 1065 | C2 | 2-CH$_3$ | H | H | 1 | CH$_3$ | H | 2-CH$_3$ | 1 | O | O | ethynyl |
| 1066 | C2 | 2-CH$_3$ | H | H | 1 | CH$_3$ | H | 2-CH$_3$ | 1 | O | O | CF$_3$ |
| 1067 | C2 | 2-CH$_3$ | H | H | 1 | CH$_3$ | H | 2-CH$_3$ | 1 | O | O | CH$_2$CF$_3$ |
| 1068 | C2 | 2-CH$_3$ | H | H | 1 | CH$_3$ | H | 2-CH$_3$ | 1 | O | O | CF$_2$CF$_3$ |
| 1069 | C2 | 2-CH$_3$ | H | H | 1 | CH$_3$ | H | 2-CH$_3$ | 1 | O | O | CF$_2$CF$_2$H |
| 1070 | C2 | 2-CH$_3$ | H | H | 1 | CH$_3$ | H | 2-CH$_3$ | 1 | O | O | CH$_2$CH=CHCl |
| 1071 | C2 | 2-CH$_3$ | H | H | 1 | CH$_3$ | H | 2-CH$_3$ | 1 | O | O | 3-Iodo-propargy |
| 1072 | C2 | 2-CH$_3$ | H | H | 1 | CH$_3$ | H | 2-CH$_3$ | 1 | O | O | c-Pr |
| 1073 | C2 | 2-CH$_3$ | H | H | 1 | CH$_3$ | H | 2-CH$_3$ | 1 | O | O | c-Hex |
| 1074 | C2 | 2-CH$_3$ | H | H | 1 | CH$_3$ | H | 2-CH$_3$ | 1 | O | O | 2-CH$_3$-c-Pr |
| 1075 | D1 | — | H | H | 1 | CH$_3$ | H | — | 0 | O | O | CH$_3$ |
| 1076 | D1 | — | H | H | 1 | CH$_3$ | H | 2-Cl | 1 | O | O | CH$_3$ |
| 1077 | D1 | 4-CH$_3$ | H | H | 1 | CH$_3$ | H | 2-Cl | 1 | O | O | CH$_3$ |
| 1078 | D1 | 4-Et | H | H | 1 | CH$_3$ | H | 2-Cl | 1 | O | O | CH$_3$ |
| 1079 | D1 | 4-CF$_3$ | H | H | 1 | CH$_3$ | H | 2-Cl | 1 | O | O | CH$_3$ |
| 1080 | D1 | 4-F | H | H | 1 | CH$_3$ | H | 2-Cl | 1 | O | O | CH$_3$ |
| 1081 | D1 | 4-Cl | H | H | 1 | CH$_3$ | H | 2-Cl | 1 | O | O | CH$_3$ |
| 1082 | D1 | 4-OCH$_3$ | H | H | 1 | CH$_3$ | H | 2-Cl | 1 | O | O | CH$_3$ |
| 1083 | D1 | 4-OEt | H | H | 1 | CH$_3$ | H | 2-Cl | 1 | O | O | CH$_3$ |
| 1084 | D1 | 4-OCF$_3$ | H | H | 1 | CH$_3$ | H | 2-Cl | 1 | O | O | CH$_3$ |
| 1085 | D1 | 5-CH$_3$ | H | H | 1 | CH$_3$ | H | 2-Cl | 1 | O | O | CH$_3$ |
| 1086 | D1 | 5-Et | H | H | 1 | CH$_3$ | H | 2-Cl | 1 | O | O | CH$_3$ |
| 1087 | D1 | 5-CF$_3$ | H | H | 1 | CH$_3$ | H | 2-Cl | 1 | O | O | CH$_3$ |
| 1088 | D1 | 5-F | H | H | 1 | CH$_3$ | H | 2-Cl | 1 | O | O | CH$_3$ |
| 1089 | D1 | 5-Cl | H | H | 1 | CH$_3$ | H | 2-Cl | 1 | O | O | CH$_3$ |
| 1090 | D1 | 5-OCH$_3$ | H | H | 1 | CH$_3$ | H | 2-Cl | 1 | O | O | CH$_3$ |
| 1091 | D1 | 5-OEt | H | H | 1 | CH$_3$ | H | 2-Cl | 1 | O | O | CH$_3$ |
| 1092 | D1 | 5-OCF$_3$ | H | H | 1 | CH$_3$ | H | 2-Cl | 1 | O | O | CH$_3$ |
| 1093 | D1 | 4,5-diCH$_3$ | H | H | 1 | CH$_3$ | H | 2-Cl | 1 | O | O | CH$_3$ |
| 1094 | D1 | 4-Et-5-CH$_3$ | H | H | 1 | CH$_3$ | H | 2-Cl | 1 | O | O | CH$_3$ |
| 1095 | D1 | 4-CF$_3$-5-F | H | H | 1 | CH$_3$ | H | 2-Cl | 1 | O | O | CH$_3$ |

TABLE 19

| | | | | | | | | | | | | |
|---|---|---|---|---|---|---|---|---|---|---|---|---|
| 1096 | D1 | 4,5-diF | H | H | 1 | CH$_3$ | H | 2-Cl | 1 | O | O | CH$_3$ |
| 1097 | D1 | 4-Cl-5-F | H | H | 1 | CH$_3$ | H | 2-Cl | 1 | O | O | CH$_3$ |
| 1098 | D1 | 4,5-diOCH$_3$ | H | H | 1 | CH$_3$ | H | 2-Cl | 1 | O | O | CH$_3$ |
| 1099 | D1 | 4-OEt-5-CH$_3$ | H | H | 1 | CH$_3$ | H | 2-Cl | 1 | O | O | CH$_3$ |
| 1100 | D1 | 4-OCF$_3$-5-F | H | H | 1 | CH$_3$ | H | 2-Cl | 1 | O | O | CH$_3$ |
| 1101 | D1 | 4-CH$_3$ | H | CH$_3$ | 1 | CH$_3$ | H | 2-Cl | 1 | O | O | CH$_3$ |
| 1102 | D1 | 4-Et | H | CH$_3$ | 1 | CH$_3$ | H | 2-Cl | 1 | O | O | CH$_3$ |
| 1103 | D1 | 4-CH$_3$ | H | Et | 1 | CH$_3$ | H | 2-Cl | 1 | O | O | CH$_3$ |
| 1104 | D1 | 4-CH$_3$ | H | i-Pr | 1 | CH$_3$ | H | 2-Cl | 1 | O | O | CH$_3$ |
| 1105 | D1 | 4-CH$_3$ | CH$_3$ | Et | 1 | CH$_3$ | H | 2-Cl | 1 | O | O | CH$_3$ |
| 1106 | D1 | 4-CH$_3$ | H | F | 1 | CH$_3$ | H | 2-Cl | 1 | O | O | CH$_3$ |
| 1107 | D1 | 4-CH$_3$ | F | F | 1 | CH$_3$ | H | 2-Cl | 1 | O | O | CH$_3$ |
| 1108 | D1 | 4-CH$_3$ | H | CF$_3$ | 1 | CH$_3$ | H | 2-Cl | 1 | O | O | CH$_3$ |
| 1109 | D1 | 4-CH$_3$ | H | c-Pr | 1 | CH$_3$ | H | 2-Cl | 1 | O | O | CH$_3$ |
| 1110 | D1 | 4-CH$_3$ | —CH2CH2— | | 1 | CH$_3$ | H | 2-Cl | 1 | O | O | CH$_3$ |
| 1111 | D1 | 4-CH$_3$ | —CH2CH2CH2— | | 1 | CH$_3$ | H | 2-Cl | 1 | O | O | CH$_3$ |
| 1112 | D1 | 4-CH$_3$ | —CH2CH(CH3)— | | 1 | CH$_3$ | H | 2-Cl | 1 | O | O | CH$_3$ |
| 1113 | D1 | 4-CH$_3$ | —CH2C(CH3)2— | | 1 | CH$_3$ | H | 2-Cl | 1 | O | O | CH$_3$ |
| 1114 | D1 | 4-CH$_3$ | H | H | 1 | H | H | 2-Cl | 1 | O | O | CH$_3$ |
| 1115 | D1 | 4-CH$_3$ | H | H | 1 | Et | H | 2-Cl | 1 | O | O | CH$_3$ |
| 1116 | D1 | 4-CH$_3$ | H | H | 1 | c-Pr | H | 2-Cl | 1 | O | O | CH$_3$ |
| 1117 | D1 | 4-CH$_3$ | H | H | 1 | CH=CH$_2$ | H | 2-Cl | 1 | O | O | CH$_3$ |
| 1118 | D1 | 4-CH$_3$ | H | H | 1 | CH$_2$CH=CH$_2$ | H | 2-Cl | 1 | O | O | CH$_3$ |
| 1119 | D1 | 4-CH$_3$ | H | H | 1 | ethynyl | H | 2-Cl | 1 | O | O | CH$_3$ |
| 1120 | D1 | 4-CH$_3$ | H | H | 1 | Propargyl | H | 2-Cl | 1 | O | O | CH$_3$ |
| 1121 | D1 | 4-CH$_3$ | H | H | 1 | CF$_3$ | H | 2-Cl | 1 | O | O | CH$_3$ |
| 1122 | D1 | 4-CH$_3$ | H | H | 1 | CH=CHCl | H | 2-Cl | 1 | O | O | CH$_3$ |
| 1123 | D1 | 4-CH$_3$ | H | H | 1 | 3,3,2-tri-Iodo-allyl | H | 2-Cl | 1 | O | O | CH$_3$ |
| 1124 | D1 | 4-CH$_3$ | H | H | 1 | 3-Iodopropargyl | H | 2-Cl | 1 | O | O | CH$_3$ |
| 1125 | D1 | 4-CH$_3$ | H | H | 1 | CN | H | 2-Cl | 1 | O | O | CH$_3$ |
| 1126 | D1 | 4-CF$_3$ | H | H | 1 | CN | H | 2-Cl | 1 | O | O | CH$_3$ |
| 1127 | D1 | 4-CH$_3$ | H | H | 1 | NO$_2$ | H | 2-Cl | 1 | O | O | CH$_3$ |
| 1128 | D1 | 4-CH$_3$ | H | H | 1 | NH$_2$ | H | 2-Cl | 1 | O | O | CH$_3$ |
| 1129 | D1 | 4-CH$_3$ | H | H | 1 | NHCH$_3$ | H | 2-Cl | 1 | O | O | CH$_3$ |
| 1130 | D1 | 4-CH$_3$ | H | H | 1 | N(CH$_3$)$_2$ | H | 2-Cl | 1 | O | O | CH$_3$ |
| 1131 | D1 | 4-CH$_3$ | H | H | 1 | CH$_3$ | CH$_3$ | 2-Cl | 1 | O | O | CH$_3$ |

TABLE 19-continued

| # | | | | | | | | | | | | |
|---|---|---|---|---|---|---|---|---|---|---|---|---|
| 1132 | D1 | 4-CH$_3$ | H | H | 1 | CH$_3$ | Et | 2-Cl | 1 | O | O | CH$_3$ |
| 1133 | D1 | 4-CH$_3$ | H | H | 1 | CH$_3$ | CH$_3$CO | 2-Cl | 1 | O | O | CH$_3$ |
| 1134 | D1 | 4-CH$_3$ | H | H | 1 | CH$_3$ | CH$_3$CH$_2$CO | 2-Cl | 1 | O | O | CH$_3$ |
| 1135 | D1 | 4-CH$_3$ | H | H | 1 | CH$_3$ | PhCO | 2-Cl | 1 | O | O | CH$_3$ |
| 1136 | D1 | 4-CH$_3$ | H | H | 1 | CH$_3$ | 4-Cl-PhCO | 2-Cl | 1 | O | O | CH$_3$ |
| 1137 | D1 | 4-CH$_3$ | H | H | 1 | CH$_3$ | PhCH$_2$CO | 2-Cl | 1 | O | O | CH$_3$ |
| 1138 | D1 | 4-CH$_3$ | H | H | 1 | CH$_3$ | CHO | 2-Cl | 1 | O | O | CH$_3$ |
| 1139 | D1 | 4-CH$_3$ | H | H | 1 | CH$_3$ | CH$_3$OCH$_2$ | 2-Cl | 1 | O | O | CH$_3$ |
| 1140 | D1 | 4-CH$_3$ | H | H | 1 | CH$_3$ | CH$_3$CH(OCH$_3$) | 2-Cl | 1 | O | O | CH$_3$ |
| 1141 | D1 | 4-CH$_3$ | H | H | 1 | CH$_3$ | CH$_3$SO$_2$ | 2-Cl | 1 | O | O | CH$_3$ |
| 1142 | D1 | 4-CH$_3$ | H | H | 1 | CH$_3$ | PhSO$_2$ | 2-Cl | 1 | O | O | CH$_3$ |
| 1143 | D1 | 4-CH$_3$ | H | H | 1 | CH$_3$ | 4-CH$_3$PhSO$_2$ | 2-Cl | 1 | O | O | CH$_3$ |
| 1144 | D1 | 4-CH$_3$ | H | H | 1 | CH$_3$ | H | 2-Cl | 1 | S | O | CH$_3$ |
| 1145 | D1 | 4-CH$_3$ | H | H | 1 | CH$_3$ | H | 2-Cl | 1 | O | S | CH$_3$ |
| 1146 | D1 | 4-CH$_3$ | H | H | 1 | CH$_3$ | H | 2-Cl | 1 | O | — | CH$_3$ |
| 1147 | D1 | 4-CH$_3$ | H | H | 1 | CH$_3$ | H | 2-Cl | 1 | O | NH | CH$_3$ |
| 1148 | D1 | 4-CH$_3$ | H | H | 1 | CH$_3$ | H | 2-Cl | 1 | O | NCH$_3$ | CH$_3$ |
| 1149 | D1 | 4-CH$_3$ | H | H | 1 | CH$_3$ | H | 2-Cl | 1 | O | O | H |
| 1150 | D1 | 4-CH$_3$ | H | H | 1 | CH$_3$ | H | 2-Cl | 1 | O | O | Et |
| 1151 | D1 | 4-CH$_3$ | H | H | 1 | CH$_3$ | H | 2-Cl | 1 | O | O | n-Pr |
| 1152 | D1 | 4-CH$_3$ | H | H | 1 | CH$_3$ | H | 2-Cl | 1 | O | O | CH$_2$CH=CH$_2$ |
| 1153 | D1 | 4-CH$_3$ | H | H | 1 | CH$_3$ | H | 2-Cl | 1 | O | O | CH=CH$_2$ |
| 1154 | D1 | 4-CH$_3$ | H | H | 1 | CH$_3$ | H | 2-Cl | 1 | O | O | Propargyl |

TABLE 20

| # | | | | | | | | | | | | |
|---|---|---|---|---|---|---|---|---|---|---|---|---|
| 1155 | D1 | 4-CH$_3$ | H | H | 1 | CH$_3$ | H | 2-Cl | 1 | O | O | ethynyl |
| 1156 | D1 | 4-CH$_3$ | H | H | 1 | CH$_3$ | H | 2-Cl | 1 | O | O | CF$_3$ |
| 1157 | D1 | 4-CH$_3$ | H | H | 1 | CH$_3$ | H | 2-Cl | 1 | O | O | CH$_2$CF$_3$ |
| 1158 | D1 | 4-CH$_3$ | H | H | 1 | CH$_3$ | H | 2-Cl | 1 | O | O | CF$_2$CF$_3$ |
| 1159 | D1 | 4-CH$_3$ | H | H | 1 | CH$_3$ | H | 2-Cl | 1 | O | O | CF$_2$CF$_2$H |
| 1160 | D1 | 4-CH$_3$ | H | H | 1 | CH$_3$ | H | 2-Cl | 1 | O | O | CH$_2$CH=CHCl |
| 1161 | D1 | 4-CH$_3$ | H | H | 1 | CH$_3$ | H | 2-Cl | 1 | O | O | 3-Iodo-propargyl |
| 1162 | D1 | 4-CH$_3$ | H | H | 1 | CH$_3$ | H | 2-Cl | 1 | O | O | c-Pr |
| 1163 | D1 | 4-CH$_3$ | H | H | 1 | CH$_3$ | H | 2-Cl | 1 | O | O | c-Hex |
| 1164 | D1 | 4-CH$_3$ | H | H | 1 | CH$_3$ | H | 2-Cl | 1 | O | O | 2-CH$_3$-c-Pr |
| 1165 | D1 | — | H | H | 1 | CH$_3$ | H | 2-CH$_3$ | 1 | O | O | CH$_3$ |
| 1166 | D1 | 4-CH$_3$ | H | H | 1 | CH$_3$ | H | 2-CH$_3$ | 1 | O | O | CH$_3$ |
| 1167 | D1 | 4-Et | H | H | 1 | CH$_3$ | H | 2-CH$_3$ | 1 | O | O | CH$_3$ |
| 1168 | D1 | 4-CF$_3$ | H | H | 1 | CH$_3$ | H | 2-CH$_3$ | 1 | O | O | CH$_3$ |
| 1169 | D1 | 4-F | H | H | 1 | CH$_3$ | H | 2-CH$_3$ | 1 | O | O | CH$_3$ |
| 1170 | D1 | 4-Cl | H | H | 1 | CH$_3$ | H | 2-CH$_3$ | 1 | O | O | CH$_3$ |
| 1171 | D1 | 4-OCH$_3$ | H | H | 1 | CH$_3$ | H | 2-CH$_3$ | 1 | O | O | CH$_3$ |
| 1172 | D1 | 4-OEt | H | H | 1 | CH$_3$ | H | 2-CH$_3$ | 1 | O | O | CH$_3$ |
| 1173 | D1 | 4-OCF$_3$ | H | H | 1 | CH$_3$ | H | 2-CH$_3$ | 1 | O | O | CH$_3$ |
| 1174 | D1 | 5-CH$_3$ | H | H | 1 | CH$_3$ | H | 2-CH$_3$ | 1 | O | O | CH$_3$ |
| 1175 | D1 | 5-Et | H | H | 1 | CH$_3$ | H | 2-CH$_3$ | 1 | O | O | CH$_3$ |
| 1176 | D1 | 5-CF$_3$ | H | H | 1 | CH$_3$ | H | 2-CH$_3$ | 1 | O | O | CH$_3$ |
| 1177 | D1 | 5-F | H | H | 1 | CH$_3$ | H | 2-CH$_3$ | 1 | O | O | CH$_3$ |
| 1178 | D1 | 5-Cl | H | H | 1 | CH$_3$ | H | 2-CH$_3$ | 1 | O | O | CH$_3$ |
| 1179 | D1 | 5-OCH$_3$ | H | H | 1 | CH$_3$ | H | 2-CH$_3$ | 1 | O | O | CH$_3$ |
| 1180 | D1 | 5-OEt | H | H | 1 | CH$_3$ | H | 2-CH$_3$ | 1 | O | O | CH$_3$ |
| 1181 | D1 | 5-OCF$_3$ | H | H | 1 | CH$_3$ | H | 2-CH$_3$ | 1 | O | O | CH$_3$ |
| 1182 | D1 | 4,5-diCH$_3$ | H | H | 1 | CH$_3$ | H | 2-CH$_3$ | 1 | O | O | CH$_3$ |
| 1183 | D1 | 4-Et-5-CH$_3$ | H | H | 1 | CH$_3$ | H | 2-CH$_3$ | 1 | O | O | CH$_3$ |
| 1184 | D1 | 4-CF$_3$-5-F | H | H | 1 | CH$_3$ | H | 2-CH$_3$ | 1 | O | O | CH$_3$ |
| 1185 | D1 | 4,5-diF | H | H | 1 | CH$_3$ | H | 2-CH$_3$ | 1 | O | O | CH$_3$ |
| 1186 | D1 | 4-Cl-5-F | H | H | 1 | CH$_3$ | H | 2-CH$_3$ | 1 | O | O | CH$_3$ |
| 1187 | D1 | 4,5-diOCH$_3$ | H | H | 1 | CH$_3$ | H | 2-CH$_3$ | 1 | O | O | CH$_3$ |
| 1188 | D1 | 4-OEt-5-CH$_3$ | H | H | 1 | CH$_3$ | H | 2-CH$_3$ | 1 | O | O | CH$_3$ |
| 1189 | D1 | 4-OCF$_3$-5-F | H | H | 1 | CH$_3$ | H | 2-CH$_3$ | 1 | O | O | CH$_3$ |
| 1190 | D1 | 4-CH$_3$ | H | CH$_3$ | 1 | CH$_3$ | H | 2-CH$_3$ | 1 | O | O | CH$_3$ |
| 1191 | D1 | 4-Et | H | CH$_3$ | 1 | CH$_3$ | H | 2-CH$_3$ | 1 | O | O | CH$_3$ |
| 1192 | D1 | 4-CH$_3$ | H | Et | 1 | CH$_3$ | H | 2-CH$_3$ | 1 | O | O | CH$_3$ |
| 1193 | D1 | 4-CH$_3$ | H | i-Pr | 1 | CH$_3$ | H | 2-CH$_3$ | 1 | O | O | CH$_3$ |
| 1194 | D1 | 4-CH$_3$ | CH$_3$ | Et | 1 | CH$_3$ | H | 2-CH$_3$ | 1 | O | O | CH$_3$ |
| 1195 | D1 | 4-CH$_3$ | H | F | 1 | CH$_3$ | H | 2-CH$_3$ | 1 | O | O | CH$_3$ |
| 1196 | D1 | 4-CH$_3$ | F | F | 1 | CH$_3$ | H | 2-CH$_3$ | 1 | O | O | CH$_3$ |
| 1197 | D1 | 4-CH$_3$ | H | CF$_3$ | 1 | CH$_3$ | H | 2-CH$_3$ | 1 | O | O | CH$_3$ |
| 1198 | D1 | 4-CH$_3$ | H | c-Pr | 1 | CH$_3$ | H | 2-CH$_3$ | 1 | O | O | CH$_3$ |
| 1199 | D1 | 4-CH$_3$ | —CH2CH2— | | 1 | CH$_3$ | H | 2-CH$_3$ | 1 | O | O | CH$_3$ |
| 1200 | D1 | 4-CH$_3$ | —CH2CH2CH2— | | 1 | CH$_3$ | H | 2-CH$_3$ | 1 | O | O | CH$_3$ |
| 1201 | D1 | 4-CH$_3$ | —CH2CH(CH3)— | | 1 | CH$_3$ | H | 2-CH$_3$ | 1 | O | O | CH$_3$ |
| 1202 | D1 | 4-CH$_3$ | —CH2C(CH3)2— | | 1 | CH$_3$ | H | 2-CH$_3$ | 1 | O | O | CH$_3$ |
| 1203 | D1 | 4-CH$_3$ | H | H | 1 | H | H | 2-CH$_3$ | 1 | O | O | CH$_3$ |
| 1204 | D1 | 4-CH$_3$ | H | H | 1 | Et | H | 2-CH$_3$ | 1 | O | O | CH$_3$ |
| 1205 | D1 | 4-CH$_3$ | H | H | 1 | c-Pr | H | 2-CH$_3$ | 1 | O | O | CH$_3$ |

TABLE 20-continued

| | | | | | | | | | | | | |
|---|---|---|---|---|---|---|---|---|---|---|---|---|
| 1206 | D1 | 4-CH$_3$ | H | H | 1 | CH=CH$_2$ | H | 2-CH$_3$ | 1 | O | O | CH$_3$ |
| 1207 | D1 | 4-CH$_3$ | H | H | 1 | CH$_2$OH=CH$_2$ | H | 2-CH$_3$ | 1 | O | O | CH$_3$ |
| 1208 | D1 | 4-CH$_3$ | H | H | 1 | ethynyl | H | 2-CH$_3$ | 1 | O | O | CH$_3$ |
| 1209 | D1 | 4-CH$_3$ | H | H | 1 | Propargyl | H | 2-CH$_3$ | 1 | O | O | CH$_3$ |
| 1210 | D1 | 4-CH$_3$ | H | H | 1 | CF$_3$ | H | 2-CH$_3$ | 1 | O | O | CH$_3$ |
| 1211 | D1 | 4-CH$_3$ | H | H | 1 | CH=CHCl | H | 2-CH$_3$ | 1 | O | O | CH$_3$ |
| 1212 | D1 | 4-CH$_3$ | H | H | 1 | 3,3,2-tri-Iodo-allyl | H | 2-CH$_3$ | 1 | O | O | CH$_3$ |
| 1213 | D1 | 4-CH$_3$ | H | H | 1 | 3-Iodopropargyl | H | 2-CH$_3$ | 1 | O | O | CH$_3$ |
| 1214 | D1 | 4-CH$_3$ | H | H | 1 | CN | H | 2-CH$_3$ | 1 | O | O | CH$_3$ |

TABLE 21

| | | | | | | | | | | | | |
|---|---|---|---|---|---|---|---|---|---|---|---|---|
| 1215 | D1 | 4-CF$_3$ | H | H | 1 | CN | H | 2-CH$_3$ | 1 | O | O | CH$_3$ |
| 1216 | D1 | 4-CH$_3$ | H | H | 1 | NO$_2$ | H | 2-CH$_3$ | 1 | O | O | CH$_3$ |
| 1217 | D1 | 4-CH$_3$ | H | H | 1 | NH$_2$ | H | 2-CH$_3$ | 1 | O | O | CH$_3$ |
| 1218 | D1 | 4-CH$_3$ | H | H | 1 | NHCH$_3$ | H | 2-CH$_3$ | 1 | O | O | CH$_3$ |
| 1219 | D1 | 4-CH$_3$ | H | H | 1 | N(CH$_3$)$_2$ | H | 2-CH$_3$ | 1 | O | O | CH$_3$ |
| 1220 | D1 | 4-CH$_3$ | H | H | 1 | CH$_3$ | CH$_3$ | 2-CH$_3$ | 1 | O | O | CH$_3$ |
| 1221 | D1 | 4-CH$_3$ | H | H | 1 | CH$_3$ | Et | 2-CH$_3$ | 1 | O | O | CH$_3$ |
| 1222 | D1 | 4-CH$_3$ | H | H | 1 | CH$_3$ | CH$_3$CO | 2-CH$_3$ | 1 | O | O | CH$_3$ |
| 1223 | D1 | 4-CH$_3$ | H | H | 1 | CH$_3$ | CH$_3$CH$_2$CO | 2-CH$_3$ | 1 | O | O | CH$_3$ |
| 1224 | D1 | 4-CH$_3$ | H | H | 1 | CH$_3$ | PhCO | 2-CH$_3$ | 1 | O | O | CH$_3$ |
| 1225 | D1 | 4-CH$_3$ | H | H | 1 | CH$_3$ | 4-Cl-PhCO | 2-CH$_3$ | 1 | O | O | CH$_3$ |
| 1226 | D1 | 4-CH$_3$ | H | H | 1 | CH$_3$ | PhCH$_2$CO | 2-CH$_3$ | 1 | O | O | CH$_3$ |
| 1227 | D1 | 4-CH$_3$ | H | H | 1 | CH$_3$ | CHO | 2-CH$_3$ | 1 | O | O | CH$_3$ |
| 1228 | D1 | 4-CH$_3$ | H | H | 1 | CH$_3$ | CH$_3$OCH$_2$ | 2-CH$_3$ | 1 | O | O | CH$_3$ |
| 1229 | D1 | 4-CH$_3$ | H | H | 1 | CH$_3$ | CH$_3$CH(OCH$_3$) | 2-CH$_3$ | 1 | O | O | CH$_3$ |
| 1230 | D1 | 4-CH$_3$ | H | H | 1 | CH$_3$ | CH$_3$SO$_2$ | 2-CH$_3$ | 1 | O | O | CH$_3$ |
| 1231 | D1 | 4-CH$_3$ | H | H | 1 | CH$_3$ | PhSO$_2$ | 2-CH$_3$ | 1 | O | O | CH$_3$ |
| 1232 | D1 | 4-CH$_3$ | H | H | 1 | CH$_3$ | 4-CH$_3$-PhSO$_2$ | 2-CH$_3$ | 1 | O | O | CH$_3$ |
| 1233 | D1 | 4-CH$_3$ | H | H | 1 | CH$_3$ | H | 2-CH$_3$ | 1 | S | O | CH$_3$ |
| 1234 | D1 | 4-CH$_3$ | H | H | 1 | CH$_3$ | H | 2-CH$_3$ | 1 | O | S | CH$_3$ |
| 1235 | D1 | 4-CH$_3$ | H | H | 1 | CH$_3$ | H | 2-CH$_3$ | 1 | O | — | CH$_3$ |
| 1236 | D1 | 4-CH$_3$ | H | H | 1 | CH$_3$ | H | 2-CH$_3$ | 1 | O | NH | CH$_3$ |
| 1237 | D1 | 4-CH$_3$ | H | H | 1 | CH$_3$ | H | 2-CH$_3$ | 1 | O | NCH$_3$ | CH$_3$ |
| 1238 | D1 | 4-CH$_3$ | H | H | 1 | CH$_3$ | H | 2-CH$_3$ | 1 | O | O | H |
| 1239 | D1 | 4-CH$_3$ | H | H | 1 | CH$_3$ | H | 2-CH$_3$ | 1 | O | O | Et |
| 1240 | D1 | 4-CH$_3$ | H | H | 1 | CH$_3$ | H | 2-CH$_3$ | 1 | O | O | n-Pr |
| 1241 | D1 | 4-CH$_3$ | H | H | 1 | CH$_3$ | H | 2-CH$_3$ | 1 | O | O | CH$_2$CH=CH$_2$ |
| 1242 | D1 | 4-CH$_3$ | H | H | 1 | CH$_3$ | H | 2-CH$_3$ | 1 | O | O | CH=CH$_2$ |
| 1243 | D1 | 4-CH$_3$ | H | H | 1 | CH$_3$ | H | 2-CH$_3$ | 1 | O | O | Propargyl |
| 1244 | D1 | 4-CH$_3$ | H | H | 1 | CH$_3$ | H | 2-CH$_3$ | 1 | O | O | ethynyl |
| 1245 | D1 | 4-CH$_3$ | H | H | 1 | CH$_3$ | H | 2-CH$_3$ | 1 | O | O | CF$_3$ |
| 1246 | D1 | 4-CH$_3$ | H | H | 1 | CH$_3$ | H | 2-CH$_3$ | 1 | O | O | CH$_2$CF$_3$ |
| 1247 | D1 | 4-CH$_3$ | H | H | 1 | CH$_3$ | H | 2-CH$_3$ | 1 | O | O | CF$_2$CF$_3$ |
| 1248 | D1 | 4-CH$_3$ | H | H | 1 | CH$_3$ | H | 2-CH$_3$ | 1 | O | O | CF$_2$CF$_2$H |
| 1249 | D1 | 4-CH$_3$ | H | H | 1 | CH$_3$ | H | 2-CH$_3$ | 1 | O | O | CH$_2$CH=CHCl |
| 1250 | D1 | 4-CH$_3$ | H | H | 1 | CH$_3$ | H | 2-CH$_3$ | 1 | O | O | 3-Iodo-propargyl |
| 1251 | D1 | 4-CH$_3$ | H | H | 1 | CH$_3$ | H | 2-CH$_3$ | 1 | O | O | c-Pr |
| 1252 | D1 | 4-CH$_3$ | H | H | 1 | CH$_3$ | H | 2-CH$_3$ | 1 | O | O | c-Hex |
| 1253 | D1 | 4-CH$_3$ | H | H | 1 | CH$_3$ | H | 2-CH$_3$ | 1 | O | O | 2-CH$_3$-c-Pr |
| 1254 | D2 | — | H | H | 1 | CH$_3$ | H | — | 0 | O | O | CH$_3$ |
| 1255 | D2 | — | H | H | 1 | CH$_3$ | H | 2-Cl | 1 | O | O | CH$_3$ |
| 1256 | D2 | 2-CH$_3$ | H | H | 1 | CH$_3$ | H | 2-Cl | 1 | O | O | CH$_3$ |
| 1257 | D2 | 2-Et | H | H | 1 | CH$_3$ | H | 2-Cl | 1 | O | O | CH$_3$ |
| 1258 | D2 | 2-CF$_3$ | H | H | 1 | CH$_3$ | H | 2-Cl | 1 | O | O | CH$_3$ |
| 1259 | D2 | 2-F | H | H | 1 | CH$_3$ | H | 2-Cl | 1 | O | O | CH$_3$ |
| 1260 | D2 | 2-Cl | H | H | 1 | CH$_3$ | H | 2-Cl | 1 | O | O | CH$_3$ |
| 1261 | D2 | 2-OCH$_3$ | H | H | 1 | CH$_3$ | H | 2-Cl | 1 | O | O | CH$_3$ |
| 1262 | D2 | 2-OEt | H | H | 1 | CH$_3$ | H | 2-Cl | 1 | O | O | CH$_3$ |
| 1263 | D2 | 2-OCF$_3$ | H | H | 1 | CH$_3$ | H | 2-Cl | 1 | O | O | CH$_3$ |
| 1264 | D2 | 5-CH$_3$ | H | H | 1 | CH$_3$ | H | 2-Cl | 1 | O | O | CH$_3$ |
| 1265 | D2 | 5-Et | H | H | 1 | CH$_3$ | H | 2-Cl | 1 | O | O | CH$_3$ |
| 1266 | D2 | 5-CF$_3$ | H | H | 1 | CH$_3$ | H | 2-Cl | 1 | O | O | CH$_3$ |
| 1267 | D2 | 5-F | H | H | 1 | CH$_3$ | H | 2-Cl | 1 | O | O | CH$_3$ |
| 1268 | D2 | 5-Cl | H | H | 1 | CH$_3$ | H | 2-Cl | 1 | O | O | CH$_3$ |
| 1269 | D2 | 5-OCH$_3$ | H | H | 1 | CH$_3$ | H | 2-Cl | 1 | O | O | CH$_3$ |
| 1270 | D2 | 5-OEt | H | H | 1 | CH$_3$ | H | 2-Cl | 1 | O | O | CH$_3$ |
| 1271 | D2 | 5-OCF$_3$ | H | H | 1 | CH$_3$ | H | 2-Cl | 1 | O | O | CH$_3$ |
| 1272 | D2 | 2,5-diCH$_3$ | H | H | 1 | CH$_3$ | H | 2-Cl | 1 | O | O | CH$_3$ |
| 1273 | D2 | 2-Et-5-CH$_3$ | H | H | 1 | CH$_3$ | H | 2-Cl | 1 | O | O | CH$_3$ |
| 1274 | D2 | 2-CF$_3$-5-F | H | H | 1 | CH$_3$ | H | 2-Cl | 1 | O | O | CH$_3$ |
| 1275 | D2 | 2,5-diF | H | H | 1 | CH$_3$ | H | 2-Cl | 1 | O | O | CH$_3$ |
| 1276 | D2 | 2-Cl-5-F | H | H | 1 | CH$_3$ | H | 2-Cl | 1 | O | O | CH$_3$ |

TABLE 22

| | | | | | | | | | | | |
|---|---|---|---|---|---|---|---|---|---|---|---|
| 1277 | D2 | 2,5-diOCH$_3$ | H | H | 1 | CH$_3$ | H | 2-Cl | 1 O | O | CH$_3$ |
| 1278 | D2 | 2-OEt-5-CH$_3$ | H | H | 1 | CH$_3$ | H | 2-Cl | 1 O | O | CH$_3$ |
| 1279 | D2 | 2-OCF$_3$-5-F | H | H | 1 | CH$_3$ | H | 2-Cl | 1 O | O | CH$_3$ |
| 1280 | D2 | 2-CH$_3$ | H | CH$_3$ | 1 | CH$_3$ | H | 2-Cl | 1 O | O | CH$_3$ |
| 1281 | D2 | 2-Et | H | CH$_3$ | 1 | CH$_3$ | H | 2-Cl | 1 O | O | CH$_3$ |
| 1282 | D2 | 2-CH$_3$ | H | Et | 1 | CH$_3$ | H | 2-Cl | 1 O | O | CH$_3$ |
| 1283 | D2 | 2-CH$_3$ | H | i-Pr | 1 | CH$_3$ | H | 2-Cl | 1 O | O | CH$_3$ |
| 1284 | D2 | 2-CH$_3$ | CH$_3$ | Et | 1 | CH$_3$ | H | 2-Cl | 1 O | O | CH$_3$ |
| 1285 | D2 | 2-CH$_3$ | H | F | 1 | CH$_3$ | H | 2-Cl | 1 O | O | CH$_3$ |
| 1286 | D2 | 2-CH$_3$ | F | F | 1 | CH$_3$ | H | 2-Cl | 1 O | O | CH$_3$ |
| 1287 | D2 | 2-CH$_3$ | H | CF$_3$ | 1 | CH$_3$ | H | 2-Cl | 1 O | O | CH$_3$ |
| 1288 | D2 | 2-CH$_3$ | H | c-Pr | 1 | CH$_3$ | H | 2-Cl | 1 O | O | CH$_3$ |
| 1289 | D2 | 2-CH$_3$ | —CH2CH2— | | 1 | CH$_3$ | H | 2-Cl | 1 O | O | CH$_3$ |
| 1290 | D2 | 2-CH$_3$ | —CH2CH2CH2— | | 1 | CH$_3$ | H | 2-Cl | 1 O | O | CH$_3$ |
| 1291 | D2 | 2-CH$_3$ | —CH2CH(CH3)— | | 1 | CH$_3$ | H | 2-Cl | 1 O | O | CH$_3$ |
| 1292 | D2 | 2-CH$_3$ | —CH2C(CH3)2— | | 1 | CH$_3$ | H | 2-Cl | 1 O | O | CH$_3$ |
| 1293 | D2 | 2-CH$_3$ | H | H | 1 | H | H | 2-Cl | 1 O | O | CH$_3$ |
| 1294 | D2 | 2-CH$_3$ | H | H | 1 | Et | H | 2-Cl | 1 O | O | CH$_3$ |
| 1295 | D2 | 2-CH$_3$ | H | H | 1 | c-Pr | H | 2-Cl | 1 O | O | CH$_3$ |
| 1296 | D2 | 2-CH$_3$ | H | H | 1 | CH=CH$_2$ | H | 2-Cl | 1 O | O | CH$_3$ |
| 1297 | D2 | 2-CH$_3$ | H | H | 1 | CH$_2$CH=CH$_2$ | H | 2-Cl | 1 O | O | CH$_3$ |
| 1298 | D2 | 2-CH$_3$ | H | H | 1 | ethynyl | H | 2-Cl | 1 O | O | CH$_3$ |
| 1299 | D2 | 2-CH$_3$ | H | H | 1 | Propargyl | H | 2-Cl | 1 O | O | CH$_3$ |
| 1300 | D2 | 2-CH$_3$ | H | H | 1 | CF$_3$ | H | 2-Cl | 1 O | O | CH$_3$ |
| 1301 | D2 | 2-CH$_3$ | H | H | 1 | CH=CHCl | H | 2-Cl | 1 O | O | CH$_3$ |
| 1302 | D2 | 2-CH$_3$ | H | H | 1 | 3,3,2-tri-Iodo-allyl | H | 2-Cl | 1 O | O | CH$_3$ |
| 1303 | D2 | 2-CH$_3$ | H | H | 1 | 3-Iodopropargyl | H | 2-Cl | 1 O | O | CH$_3$ |
| 1304 | D2 | 2-CH$_3$ | H | H | 1 | CN | H | 2-Cl | 1 O | O | CH$_3$ |
| 1305 | D2 | 2-CF$_3$ | H | H | 1 | CN | H | 2-Cl | 1 O | O | CH$_3$ |
| 1306 | D2 | 2-CH$_3$ | H | H | 1 | NO$_2$ | H | 2-Cl | 1 O | O | CH$_3$ |
| 1307 | D2 | 2-CH$_3$ | H | H | 1 | NH$_2$ | H | 2-Cl | 1 O | O | CH$_3$ |
| 1308 | D2 | 2-CH$_3$ | H | H | 1 | NHCH$_3$ | H | 2-Cl | 1 O | O | CH$_3$ |
| 1309 | D2 | 2-CH$_3$ | H | H | 1 | N(CH$_3$)$_2$ | H | 2-Cl | 1 O | O | CH$_3$ |
| 1310 | D2 | 2-CH$_3$ | H | H | 1 | CH$_3$ | CH$_3$ | 2-Cl | 1 O | O | CH$_3$ |
| 1311 | D2 | 2-CH$_3$ | H | H | 1 | CH$_3$ | Et | 2-Cl | 1 O | O | CH$_3$ |
| 1312 | D2 | 2-CH$_3$ | H | H | 1 | CH$_3$ | CH$_3$CO | 2-Cl | 1 O | O | CH$_3$ |
| 1313 | D2 | 2-CH$_3$ | H | H | 1 | CH$_3$ | CH$_3$CH$_2$CO | 2-Cl | 1 O | O | CH$_3$ |
| 1314 | D2 | 2-CH$_3$ | H | H | 1 | CH$_3$ | PhCO | 2-Cl | 1 O | O | CH$_3$ |
| 1315 | D2 | 2-CH$_3$ | H | H | 1 | CH$_3$ | 4-Cl-PhCO | 2-Cl | 1 O | O | CH$_3$ |
| 1316 | D2 | 2-CH$_3$ | H | H | 1 | CH$_3$ | PhCH$_2$CO | 2-Cl | 1 O | O | CH$_3$ |
| 1317 | D2 | 2-CH$_3$ | H | H | 1 | CH$_3$ | CHO | 2-Cl | 1 O | O | CH$_3$ |
| 1318 | D2 | 2-CH$_3$ | H | H | 1 | CH$_3$ | CH$_3$OCH$_2$ | 2-Cl | 1 O | O | CH$_3$ |
| 1319 | D2 | 2-CH$_3$ | H | H | 1 | CH$_3$ | CH$_3$CH(OCH$_3$) | 2-Cl | 1 O | O | CH$_3$ |
| 1320 | D2 | 2-CH$_3$ | H | H | 1 | CH$_3$ | CH$_3$SO$_2$ | 2-Cl | 1 O | O | CH$_3$ |
| 1321 | D2 | 2-CH$_3$ | H | H | 1 | CH$_3$ | PhSO$_2$ | 2-Cl | 1 O | O | CH$_3$ |
| 1322 | D2 | 2-CH$_3$ | H | H | 1 | CH$_3$ | 4-CH$_3$-PhSO$_2$ | 2-Cl | 1 O | O | CH$_3$ |
| 1323 | D2 | 2-CH$_3$ | H | H | 1 | CH$_3$ | H | 2-Cl | 1 S | O | CH$_3$ |
| 1324 | D2 | 2-CH$_3$ | H | H | 1 | CH$_3$ | H | 2-Cl | 1 O | S | CH$_3$ |
| 1325 | D2 | 2-CH$_3$ | H | H | 1 | CH$_3$ | H | 2-Cl | 1 O | — | CH$_3$ |
| 1326 | D2 | 2-CH$_3$ | H | H | 1 | CH$_3$ | H | 2-Cl | 1 O | NH | CH$_3$ |
| 1327 | D2 | 2-CH$_3$ | H | H | 1 | CH$_3$ | H | 2-Cl | 1 O | NCH$_3$ | CH$_3$ |
| 1328 | D2 | 2-CH$_3$ | H | H | 1 | CH$_3$ | H | 2-Cl | 1 O | O | H |
| 1329 | D2 | 2-CH$_3$ | H | H | 1 | CH$_3$ | H | 2-Cl | 1 O | O | Et |
| 1330 | D2 | 2-CH$_3$ | H | H | 1 | CH$_3$ | H | 2-Cl | 1 O | O | n-Pr |
| 1331 | D2 | 2-CH$_3$ | H | H | 1 | CH$_3$ | H | 2-Cl | 1 O | O | CH$_2$CH=CH$_2$ |
| 1332 | D2 | 2-CH$_3$ | H | H | 1 | CH$_3$ | H | 2-Cl | 1 O | O | CH=CH$_2$ |
| 1333 | D2 | 2-CH$_3$ | H | H | 1 | CH$_3$ | H | 2-Cl | 1 O | O | Propargyl |
| 1334 | D2 | 2-CH$_3$ | H | H | 1 | CH$_3$ | H | 2-Cl | 1 O | O | ethynyl |
| 1335 | D2 | 2-CH$_3$ | H | H | 1 | CH$_3$ | H | 2-Cl | 1 O | O | CF$_3$ |
| 1336 | D2 | 2-CH$_3$ | H | H | 1 | CH$_3$ | H | 2-Cl | 1 O | O | CH$_2$CF$_3$ |
| 1337 | D2 | 2-CH$_3$ | H | H | 1 | CH$_3$ | H | 2-Cl | 1 O | O | CF$_2$CF$_3$ |
| 1338 | D2 | 2-CH$_3$ | H | H | 1 | CH$_3$ | H | 2-Cl | 1 O | O | CF$_2$CF$_2$H |

TABLE 23

| | | | | | | | | | | | |
|---|---|---|---|---|---|---|---|---|---|---|---|
| 1339 | D2 | 2-CH$_3$ | H | H | 1 | CH$_3$ | H | 2-Cl | 1 O | O | CH$_2$CH=CHCl |
| 1340 | D2 | 2-CH$_3$ | H | H | 1 | CH$_3$ | H | 2-Cl | 1 O | O | 3-Iodo-propargyl |
| 1341 | D2 | 2-CH$_3$ | H | H | 1 | CH$_3$ | H | 2-Cl | 1 O | O | c-Pr |
| 1342 | D2 | 2-CH$_3$ | H | H | 1 | CH$_3$ | H | 2-Cl | 1 O | O | c-Hex |
| 1343 | D2 | 2-CH$_3$ | H | H | 1 | CH$_3$ | H | 2-Cl | 1 O | O | 2-CH$_3$-c-Pr |
| 1344 | D2 | — | H | H | 1 | CH$_3$ | H | 2-CH$_3$ | 1 O | O | CH$_3$ |
| 1345 | D2 | 2-CH$_3$ | H | H | 1 | CH$_3$ | H | 2-CH$_3$ | 1 O | O | CH$_3$ |
| 1346 | D2 | 2-Et | H | H | 1 | CH$_3$ | H | 2-CH$_3$ | 1 O | O | CH$_3$ |
| 1347 | D2 | 2-CF$_3$ | H | H | 1 | CH$_3$ | H | 2-CH$_3$ | 1 O | O | CH$_3$ |
| 1348 | D2 | 2-F | H | H | 1 | CH$_3$ | H | 2-CH$_3$ | 1 O | O | CH$_3$ |
| 1349 | D2 | 2-Cl | H | H | 1 | CH$_3$ | H | 2-CH$_3$ | 1 O | O | CH$_3$ |
| 1350 | D2 | 2-OCH$_3$ | H | H | 1 | CH$_3$ | H | 2-CH$_3$ | 1 O | O | CH$_3$ |

TABLE 23-continued

| | | | | | | | | | | | |
|---|---|---|---|---|---|---|---|---|---|---|---|
| 1351 | D2 | 2-OEt | H | H | 1 | CH₃ | H | 2-CH₃ | 1 | O | O | CH₃ |
| 1352 | D2 | 2-OCF₃ | H | H | 1 | CH₃ | H | 2-CH₃ | 1 | O | O | CH₃ |
| 1353 | D2 | 5-CH₃ | H | H | 1 | CH₃ | H | 2-CH₃ | 1 | O | O | CH₃ |
| 1354 | D2 | 5-Et | H | H | 1 | CH₃ | H | 2-CH₃ | 1 | O | O | CH₃ |
| 1355 | D2 | 5-CF₃ | H | H | 1 | CH₃ | H | 2-CH₃ | 1 | O | O | CH₃ |
| 1356 | D2 | 5-F | H | H | 1 | CH₃ | H | 2-CH₃ | 1 | O | O | CH₃ |
| 1357 | D2 | 5-Cl | H | H | 1 | CH₃ | H | 2-CH₃ | 1 | O | O | CH₃ |
| 1358 | D2 | 5-OCH₃ | H | H | 1 | CH₃ | H | 2-CH₃ | 1 | O | O | CH₃ |
| 1359 | D2 | 5-OEt | H | H | 1 | CH₃ | H | 2-CH₃ | 1 | O | O | CH₃ |
| 1360 | D2 | 5-OCF₃ | H | H | 1 | CH₃ | H | 2-CH₃ | 1 | O | O | CH₃ |
| 1361 | D2 | 2,5-diCH₃ | H | H | 1 | CH₃ | H | 2-CH₃ | 1 | O | O | CH₃ |
| 1362 | D2 | 2-Et-5-CH₃ | H | H | 1 | CH₃ | H | 2-CH₃ | 1 | O | O | CH₃ |
| 1363 | D2 | 2-CF₃-5-F | H | H | 1 | CH₃ | H | 2-CH₃ | 1 | O | O | CH₃ |
| 1364 | D2 | 2,5-diF | H | H | 1 | CH₃ | H | 2-CH₃ | 1 | O | O | CH₃ |
| 1365 | D2 | 2-Cl-5-F | H | H | 1 | CH₃ | H | 2-CH₃ | 1 | O | O | CH₃ |
| 1366 | D2 | 2,5-diOCH₃ | H | H | 1 | CH₃ | H | 2-CH₃ | 1 | O | O | CH₃ |
| 1367 | D2 | 2-OEt-5-CH₃ | H | H | 1 | CH₃ | H | 2-CH₃ | 1 | O | O | CH₃ |
| 1368 | D2 | 2-OCF₃-5-F | H | H | 1 | CH₃ | H | 2-CH₃ | 1 | O | O | CH₃ |
| 1369 | D2 | 2-CH₃ | H | CH₃ | 1 | CH₃ | H | 2-CH₃ | 1 | O | O | CH₃ |
| 1370 | D2 | 2-Et | H | CH₃ | 1 | CH₃ | H | 2-CH₃ | 1 | O | O | CH₃ |
| 1371 | D2 | 2-CH₃ | H | Et | 1 | CH₃ | H | 2-CH₃ | 1 | O | O | CH₃ |
| 1372 | D2 | 2-CH₃ | H | i-Pr | 1 | CH₃ | H | 2-CH₃ | 1 | O | O | CH₃ |
| 1373 | D2 | 2-CH₃ | CH₃ | Et | 1 | CH₃ | H | 2-CH₃ | 1 | O | O | CH₃ |
| 1374 | D2 | 2-CH₃ | H | F | 1 | CH₃ | H | 2-CH₃ | 1 | O | O | CH₃ |
| 1375 | D2 | 2-CH₃ | F | F | 1 | CH₃ | H | 2-CH₃ | 1 | O | O | CH₃ |
| 1376 | D2 | 2-CH₃ | H | CF₃ | 1 | CH₃ | H | 2-CH₃ | 1 | O | O | CH₃ |
| 1377 | D2 | 2-CH₃ | H | c-Pr | 1 | CH₃ | H | 2-CH₃ | 1 | O | O | CH₃ |
| 1378 | D2 | 2-CH₃ | —CH2CH2— | | 1 | CH₃ | H | 2-CH₃ | 1 | O | O | CH₃ |
| 1379 | D2 | 2-CH₃ | —CH2CH2CH2— | | 1 | CH₃ | H | 2-CH₃ | 1 | O | O | CH₃ |
| 1380 | D2 | 2-CH₃ | —CH2CH(CH3)— | | 1 | CH₃ | H | 2-CH₃ | 1 | O | O | CH₃ |
| 1381 | D2 | 2-CH₃ | —CH2C(CH3)2— | | 1 | CH₃ | H | 2-CH₃ | 1 | O | O | CH₃ |
| 1382 | D2 | 2-CH₃ | H | H | 1 | H | H | 2-CH₃ | 1 | O | O | CH₃ |
| 1383 | D2 | 2-CH₃ | H | H | 1 | Et | H | 2-CH₃ | 1 | O | O | CH₃ |
| 1384 | D2 | 2-CH₃ | H | H | 1 | c-Pr | H | 2-CH₃ | 1 | O | O | CH₃ |
| 1385 | D2 | 2-CH₃ | H | H | 1 | CH=CH₂ | H | 2-CH₃ | 1 | O | O | CH₃ |
| 1386 | D2 | 2-CH₃ | H | H | 1 | CH₂CH=CH₂ | H | 2-CH₃ | 1 | O | O | CH₃ |
| 1387 | D2 | 2-CH₃ | H | H | 1 | ethynyl | H | 2-CH₃ | 1 | O | O | CH₃ |
| 1388 | D2 | 2-CH₃ | H | H | 1 | Propargyl | H | 2-CH₃ | 1 | O | O | CH₃ |
| 1389 | D2 | 2-CH₃ | H | H | 1 | CF₃ | H | 2-CH₃ | 1 | O | O | CH₃ |
| 1390 | D2 | 2-CH₃ | H | H | 1 | CH=CHCl | H | 2-CH₃ | 1 | O | O | CH₃ |
| 1391 | D2 | 2-CH₃ | H | H | 1 | 3,3,2-tri-Iodo-allyl | H | 2-CH₃ | 1 | O | O | CH₃ |
| 1392 | D2 | 2-CH₃ | H | H | 1 | 3-Iodopropargyl | H | 2-CH₃ | 1 | O | O | CH₃ |
| 1393 | D2 | 2-CH₃ | H | H | 1 | CN | H | 2-CH₃ | 1 | O | O | CH₃ |
| 1394 | D2 | 2-CF₃ | H | H | 1 | CN | H | 2-CH₃ | 1 | O | O | CH₃ |
| 1395 | D2 | 2-CH₃ | H | H | 1 | NO₂ | H | 2-CH₃ | 1 | O | O | CH₃ |
| 1396 | D2 | 2-CH₃ | H | H | 1 | NH₂ | H | 2-CH₃ | 1 | O | O | CH₃ |
| 1397 | D2 | 2-CH₃ | H | H | 1 | NHCH₃ | H | 2-CH₃ | 1 | O | O | CH₃ |
| 1398 | D2 | 2-CH₃ | H | H | 1 | N(CH₃)₂ | H | 2-CH₃ | 1 | O | O | CH₃ |
| 1399 | D2 | 2-CH₃ | H | H | 1 | CH₃ | CH₃ | 2-CH₃ | 1 | O | O | CH₃ |
| 1400 | D2 | 2-CH₃ | H | H | 1 | CH₃ | Et | 2-CH₃ | 1 | O | O | CH₃ |

TABLE 24

| | | | | | | | | | | | |
|---|---|---|---|---|---|---|---|---|---|---|---|
| 1401 | D2 | 2-CH₃ | H | H | 1 CH₃ | CH₃CO | 2-CH₃ | 1 | O | O | CH₃ |
| 1402 | D2 | 2-CH₃ | H | H | 1 CH₃ | CH₃CH₂CO | 2-CH₃ | 1 | O | O | CH₃ |
| 1403 | D2 | 2-CH₃ | H | H | 1 CH₃ | PhCO | 2-CH₃ | 1 | O | O | CH₃ |
| 1404 | D2 | 2-CH₃ | H | H | 1 CH₃ | 4-Cl-PhCO | 2-CH₃ | 1 | O | O | CH₃ |
| 1405 | D2 | 2-CH₃ | H | H | 1 CH₃ | PhCH₂CO | 2-CH₃ | 1 | O | O | CH₃ |
| 1406 | D2 | 2-CH₃ | H | H | 1 CH₃ | CHO | 2-CH₃ | 1 | O | O | CH₃ |
| 1407 | D2 | 2-CH₃ | H | H | 1 CH₃ | CH₃OCH₂ | 2-CH₃ | 1 | O | O | CH₃ |
| 1408 | D2 | 2-CH₃ | H | H | 1 CH₃ | CH₃CH(OCH₃) | 2-CH₃ | 1 | O | O | CH₃ |
| 1409 | D2 | 2-CH₃ | H | H | 1 CH₃ | CH₃SO₂ | 2-CH₃ | 1 | O | O | CH₃ |
| 1410 | D2 | 2-CH₃ | H | H | 1 CH₃ | PhSO₂ | 2-CH₃ | 1 | O | O | CH₃ |
| 1411 | D2 | 2-CH₃ | H | H | 1 CH₃ | 4-CH₃-PhSO₂ | 2-CH₃ | 1 | O | O | CH₃ |
| 1412 | D2 | 2-CH₃ | H | H | 1 CH₃ | H | 2-CH₃ | 1 | S | O | CH₃ |
| 1413 | D2 | 2-CH₃ | H | H | 1 CH₃ | H | 2-CH₃ | 1 | O | S | CH₃ |
| 1414 | D2 | 2-CH₃ | H | H | 1 CH₃ | H | 2-CH₃ | 1 | O | — | CH₃ |
| 1415 | D2 | 2-CH₃ | H | H | 1 CH₃ | H | 2-CH₃ | 1 | O | NH | CH₃ |
| 1416 | D2 | 2-CH₃ | H | H | 1 CH₃ | H | 2-CH₃ | 1 | O | NCH₃ | CH₃ |
| 1417 | D2 | 2-CH₃ | H | H | 1 CH₃ | H | 2-CH₃ | 1 | O | O | H |
| 1418 | D2 | 2-CH₃ | H | H | 1 CH₃ | H | 2-CH₃ | 1 | O | O | Et |
| 1419 | D2 | 2-CH₃ | H | H | 1 CH₃ | H | 2-CH₃ | 1 | O | O | n-Pr |
| 1420 | D2 | 2-CH₃ | H | H | 1 CH₃ | H | 2-CH₃ | 1 | O | O | CH₂CH=CH₂ |
| 1421 | D2 | 2-CH₃ | H | H | 1 CH₃ | H | 2-CH₃ | 1 | O | O | CH=CH₂ |
| 1422 | D2 | 2-CH₃ | H | H | 1 CH₃ | H | 2-CH₃ | 1 | O | O | Propargyl |
| 1423 | D2 | 2-CH₃ | H | H | 1 CH₃ | H | 2-CH₃ | 1 | O | O | ethynyl |
| 1424 | D2 | 2-CH₃ | H | H | 1 CH₃ | H | 2-CH₃ | 1 | O | O | CF₃ |

TABLE 24-continued

| | | | | | | | | | | | |
|---|---|---|---|---|---|---|---|---|---|---|---|
| 1425 | D2 | 2-CH₃ | H | H | 1 CH₃ | H | 2-CH₃ | 1 | O | O | CH₂CF₃ |
| 1426 | D2 | 2-CH₃ | H | H | 1 CH₃ | H | 2-CH₃ | 1 | O | O | CF₂CF₃ |
| 1427 | D2 | 2-CH₃ | H | H | 1 CH₃ | H | 2-CH₃ | 1 | O | O | CF₂CF₂H |
| 1428 | D2 | 2-CH₃ | H | H | 1 CH₃ | H | 2-CH₃ | 1 | O | O | CH₂CH=CHCl |
| 1429 | D2 | 2-CH₃ | H | H | 1 CH₃ | H | 2-CH₃ | 1 | O | O | 3-Iodo-propargyl |
| 1430 | D2 | 2-CH₃ | H | H | 1 CH₃ | H | 2-CH₃ | 1 | O | O | c-Pr |
| 1431 | D2 | 2-CH₃ | H | H | 1 CH₃ | H | 2-CH₃ | 1 | O | O | c-Hex |
| 1432 | D2 | 2-CH₃ | H | H | 1 CH₃ | H | 2-CH₃ | 1 | O | O | 2-CH₃-c-Pr |
| 1433 | E1 | — | H | H | 1 CH₃ | H | — | 0 | O | O | CH₃ |
| 1434 | E1 | — | H | H | 1 CH₃ | H | 2-Cl | 1 | O | O | CH₃ |
| 1435 | E1 | 3-CH₃ | H | H | 1 CH₃ | H | 2-Cl | 1 | O | O | CH₃ |
| 1436 | E1 | 3-Et | H | H | 1 CH₃ | H | 2-Cl | 1 | O | O | CH₃ |
| 1437 | E1 | 3-CF₃ | H | H | 1 CH₃ | H | 2-Cl | 1 | O | O | CH₃ |
| 1438 | E1 | 4-CF₃ | H | H | 1 CH₃ | H | 2-Cl | 1 | O | O | CH₃ |
| 1439 | E1 | 3-F | H | H | 1 CH₃ | H | 2-Cl | 1 | O | O | CH₃ |
| 1440 | E1 | 3-Cl | H | H | 1 CH₃ | H | 2-Cl | 1 | O | O | CH₃ |
| 1441 | E1 | 3-OCH₃ | H | H | 1 CH₃ | H | 2-Cl | 1 | O | O | CH₃ |
| 1442 | E1 | 3-OEt | H | H | 1 CH3 | H | 2-Cl | 1 | O | O | CH₃ |
| 1443 | E1 | 3-OCF₃ | H | H | 1 CH₃ | H | 2-Cl | 1 | O | O | CH₃ |
| 1444 | E1 | 6-CH₃ | H | H | 1 CH₃ | H | 2-Cl | 1 | O | O | CH₃ |
| 1445 | E1 | 6-Et | H | H | 1 CH₃ | H | 2-Cl | 1 | O | O | CH₃ |
| 1446 | E1 | 6-CF₃ | H | H | 1 CH₃ | H | 2-Cl | 1 | O | O | CH₃ |
| 1447 | E1 | 6-F | H | H | 1 CH₃ | H | 2-Cl | 1 | O | O | CH₃ |
| 1448 | E1 | 6-Cl | H | H | 1 CH₃ | H | 2-Cl | 1 | O | O | CH₃ |
| 1449 | E1 | 6-OCH₃ | H | H | 1 CH₃ | H | 2-Cl | 1 | O | O | CH₃ |
| 1450 | E1 | 6-OEt | H | H | 1 CH₃ | H | 2-Cl | 1 | O | O | CH₃ |
| 1451 | E1 | 6-OCF₃ | H | H | 1 CH₃ | H | 2-Cl | 1 | O | O | CH₃ |
| 1452 | E1 | 3,6-diCH₃ | H | H | 1 CH₃ | H | 2-Cl | 1 | O | O | CH₃ |
| 1453 | E1 | 3-Et-6-CH₃ | H | H | 1 CH₃ | H | 2-Cl | 1 | O | O | CH₃ |
| 1454 | E1 | 3-CF₃-6-F | H | H | 1 CH₃ | H | 2-Cl | 1 | O | O | CH₃ |
| 1455 | E1 | 3,6-diF | H | H | 1 CH₃ | H | 2-Cl | 1 | O | O | CH₃ |
| 1456 | E1 | 3-Cl-6-F | H | H | 1 CH₃ | H | 2-Cl | 1 | O | O | CH₃ |
| 1457 | E1 | 3,6-diOCH₃ | H | H | 1 CH₃ | H | 2-Cl | 1 | O | O | CH₃ |
| 1458 | E1 | 3-OEt-6-CH₃ | H | H | 1 CH₃ | H | 2-Cl | 1 | O | O | CH₃ |
| 1459 | E1 | 3-OCF₃-6-F | H | H | 1 CH₃ | H | 2-Cl | 1 | O | O | CH₃ |
| 1460 | E1 | 3-CH₃ | H | CH₃ | 1 CH₃ | H | 2-Cl | 1 | O | O | CH₃ |
| 1461 | E1 | 3-Et | H | CH₃ | 1 CH₃ | H | 2-Cl | 1 | O | O | CH₃ |
| 1462 | E1 | 6-Et | H | CH₃ | 1 CH₃ | H | 2-Cl | 1 | O | O | CH₃ |

TABLE 25

| | | | | | | | | | | | |
|---|---|---|---|---|---|---|---|---|---|---|---|
| 1463 | E1 | 6-Cl | H | CH₃ | 1 CH₃ | H | 2-Cl | 1 | O | O | CH₃ |
| 1464 | E1 | 6-Cl | H | Et | 1 CH₃ | H | 2-Cl | 1 | O | O | CH₃ |
| 1465 | E1 | 6-Cl | H | i-Pr | 1 CH₃ | H | 2-Cl | 1 | O | O | CH₃ |
| 1466 | E1 | 3-CH₃ | H | Et | 1 CH₃ | H | 2-Cl | 1 | O | O | CH₃ |
| 1467 | E1 | 3-CH₃ | H | i-Pr | 1 CH₃ | H | 2-Cl | 1 | O | O | CH₃ |
| 1468 | E1 | 3-CH₃ | CH₃ | Et | 1 CH₃ | H | 2-Cl | 1 | O | O | CH₃ |
| 1469 | E1 | 3-CH₃ | H | F | 1 CH₃ | H | 2-Cl | 1 | O | O | CH₃ |
| 1470 | E1 | 3-CH₃ | F | F | 1 CH₃ | H | 2-Cl | 1 | O | O | CH₃ |
| 1471 | E1 | 3-CH₃ | H | CF₃ | 1 CH₃ | H | 2-Cl | 1 | O | O | CH₃ |
| 1472 | E1 | 3-CH₃ | H | c-Pr | 1 CH₃ | H | 2-Cl | 1 | O | O | CH₃ |
| 1473 | E1 | 3-CH₃ | —CH2CH2— | | 1 CH₃ | H | 2-Cl | 1 | O | O | CH₃ |
| 1474 | E1 | 3-CH₃ | —CH2CH2CH2— | | 1 CH₃ | 1-1 | 2-Cl | 1 | O | O | CH₃ |
| 1475 | E1 | 3-CH₃ | —CH2CH(CH3)— | | 1 CH₃ | H | 2-Cl | 1 | O | O | CH₃ |
| 1476 | E1 | 3-CH₃ | —CH2C(CH3)2— | | 1 CH₃ | H | 2-Cl | 1 | O | O | CH₃ |
| 1477 | E1 | 3-CH₃ | H | H | 1 H | H | 2-Cl | 1 | O | O | CH₃ |
| 1478 | E1 | 3-CH₃ | H | H | 1 Et | H | 2-Cl | 1 | O | O | CH₃ |
| 1479 | E1 | 3-CH₃ | H | H | 1 c-Pr | H | 2-Cl | 1 | O | O | CH₃ |
| 1480 | E1 | 3-CH₃ | H | H | 1 CH=CH₂ | H | 2-Cl | 1 | O | O | CH₃ |
| 1481 | E1 | 3-CH₃ | H | H | 1 CH₂CH=CH₂ | H | 2-Cl | 1 | O | O | CH₃ |
| 1482 | E1 | 3-CH₃ | H | H | 1 ethynyl | H | 2-Cl | 1 | O | O | CH₃ |
| 1483 | E1 | 3-CH₃ | H | H | 1 Propargyl | H | 2-Cl | 1 | O | O | CH₃ |
| 1484 | E1 | 3-CH₃ | H | H | 1 CF₃ | H | 2-Cl | 1 | O | O | CH₃ |
| 1485 | E1 | 3-CH₃ | H | H | 1 CH=CHCl | H | 2-Cl | 1 | O | O | CH₃ |
| 1486 | E1 | 3-CH₃ | H | H | 1 3,3,2-tri-Indo-allyl | H | 2-Cl | 1 | O | O | CH₃ |
| 1487 | E1 | 3-CH₃ | H | H | 1 3-Iodopropargyl | H | 2-Cl | 1 | O | O | CH₃ |
| 1488 | E1 | 3-CH₃ | H | H | 1 CN | H | 2-Cl | 1 | O | O | CH₃ |
| 1489 | E1 | 3-CF₃ | H | H | 1 CN | H | 2-Cl | 1 | O | O | CH₃ |
| 1490 | E1 | 3-CH₃ | H | H | 1 NO₂ | H | 2-Cl | 1 | O | O | CH₃ |
| 1491 | E1 | 3-CH₃ | H | H | 1 NH₂ | H | 2-Cl | 1 | O | O | CH₃ |
| 1492 | E1 | 3-CH₃ | H | H | 1 NHCH₃ | H | 2-Cl | 1 | O | O | CH₃ |
| 1493 | E1 | 3-CH₃ | H | H | 1 N(CH₃)₂ | H | 2-Cl | 1 | O | O | CH₃ |
| 1494 | E1 | 3-CH₃ | H | H | 1 CH₃ | CH₃ | 2-Cl | 1 | O | O | CH₃ |
| 1495 | E1 | 3-CH₃ | H | H | 1 CH₃ | Et | 2-Cl | 1 | O | O | CH₃ |
| 1496 | E1 | 3-CH₃ | H | H | 1 CH₃ | CH₃CO | 2-Cl | 1 | O | O | CH₃ |
| 1497 | E1 | 3-CH₃ | H | H | 1 CH₃ | CH₃CH₂CO | 2-Cl | 1 | O | O | CH₃ |
| 1498 | E1 | 3-CH₃ | H | H | 1 CH₃ | PhCO | 2-Cl | 1 | O | O | CH₃ |

TABLE 25-continued

| No. | Type | | | | | | | | | | | |
|---|---|---|---|---|---|---|---|---|---|---|---|---|
| 1499 | E1 | 3-CH₃ | H | H | 1 | CH₃ | 4-Cl-PhCO | 2-Cl | 1 | O | O | CH₃ |
| 1500 | E1 | 3-CH₃ | H | H | 1 | CH₃ | PhCH₂CO | 2-Cl | 1 | O | O | CH₃ |
| 1501 | E1 | 3-CH₃ | H | H | 1 | CH₃ | CHO | 2-Cl | 1 | O | O | CH₃ |
| 1502 | E1 | 3-CH₃ | H | H | 1 | CH₃ | CH₃OCH₂ | 2-Cl | 1 | O | O | CH₃ |
| 1503 | E1 | 3-CH₃ | H | H | 1 | CH₃ | CH₃CH(OCH₃) | 2-Cl | 1 | O | O | CH₃ |
| 1504 | E1 | 3-CH₃ | H | H | 1 | CH₃ | CH₃SO₂ | 2-Cl | 1 | O | O | CH₃ |
| 1505 | E1 | 3-CH₃ | H | H | 1 | CH₃ | PhSO₂ | 2-Cl | 1 | O | O | CH₃ |
| 1506 | E1 | 3-CH₃ | H | H | 1 | CH₃ | 4-CH₃-PhSO₂ | 2-Cl | 1 | O | O | CH₃ |
| 1507 | E1 | 3-CH₃ | H | H | 1 | CH₃ | H | 2-Cl | 1 | S | O | CH₃ |
| 1508 | E1 | 3-CH₃ | H | H | 1 | CH₃ | H | 2-Cl | 1 | O | S | CH₃ |
| 1509 | E1 | 3-CH₃ | H | H | 1 | CH₃ | H | 2-Cl | 1 | O | — | CH₃ |
| 1510 | E1 | 3-CH₃ | H | H | 1 | CH₃ | H | 2-Cl | 1 | O | NH | CH₃ |
| 1511 | E1 | 3-CH₃ | H | H | 1 | CH₃ | H | 2-Cl | 1 | O | NCH₃ | CH₃ |
| 1512 | E1 | 3-CH₃ | H | H | 1 | CH₃ | H | 2-Cl | 1 | O | O | H |
| 1513 | E1 | 3-CH₃ | H | H | 1 | CH₃ | H | 2-Cl | 1 | O | O | Et |
| 1514 | E1 | 3-CH₃ | H | H | 1 | CH₃ | H | 2-Cl | 1 | O | O | n-Pr |
| 1515 | E1 | 3-CH₃ | H | H | 1 | CH₃ | H | 2-Cl | 1 | O | O | CH₂CH=CH₂ |
| 1516 | E1 | 3-CH₃ | H | H | 1 | CH₃ | H | 2-Cl | 1 | O | O | CH=CH₂ |
| 1517 | E1 | 3-CH₃ | H | H | 1 | CH₃ | H | 2-Cl | 1 | O | O | Propargyl |
| 1518 | E1 | 3-CH₃ | H | H | 1 | CH₃ | H | 2-Cl | 1 | O | O | ethynyl |
| 1519 | E1 | 3-CH₃ | H | H | 1 | CH₃ | H | 2-Cl | 1 | O | O | CF₃ |
| 1520 | E1 | 3-CH₃ | H | H | 1 | CH₃ | H | 2-Cl | 1 | O | O | CH₂CF₃ |
| 1521 | E1 | 3-CH₃ | H | H | 1 | CH₃ | H | 2-Cl | 1 | O | O | CF₂CF₃ |
| 1522 | E1 | 3-CH₃ | H | H | 1 | CH₃ | H | 2-Cl | 1 | O | O | CF₂CF₂H |
| 1523 | E1 | 3-CH₃ | H | H | 1 | CH₃ | H | 2-Cl | 1 | O | O | CH₂CH=CHCl |
| 1524 | E1 | 3-CH₃ | H | H | 1 | CH₃ | H | 2-Cl | 1 | O | O | 3-Iodo-propargyl |

TABLE 26

| No. | Type | | | | | | | | | | | |
|---|---|---|---|---|---|---|---|---|---|---|---|---|
| 1525 | E1 | 3-CH₃ | H | H | 1 | CH₃ | H | 2-Cl | 1 | O | O | c-Pr |
| 1526 | E1 | 3-CH₃ | H | H | 1 | CH₃ | H | 2-Cl | 1 | O | O | c-Hex |
| 1527 | E1 | 3-CH₃ | H | H | 1 | CH₃ | H | 2-Cl | 1 | O | O | 2-CH₃-c-Pr |
| 1528 | E1 | — | H | H | 1 | CH₃ | H | 2-CH₃ | 1 | O | O | CH₃ |
| 1529 | E1 | 3-CH₃ | H | H | 1 | CH₃ | H | 2-CH₃ | 1 | O | O | CH₃ |
| 1530 | E1 | 3-Et | H | H | 1 | CH₃ | H | 2-CH₃ | 1 | O | O | CH₃ |
| 1531 | E1 | 3-CF₃ | H | H | 1 | CH₃ | H | 2-CH₃ | 1 | O | O | CH₃ |
| 1532 | E1 | 3-F | H | H | 1 | CH₃ | H | 2-CH₃ | 1 | O | O | CH₃ |
| 1533 | E1 | 3-Cl | H | H | 1 | CH₃ | H | 2-CH₃ | 1 | O | O | CH₃ |
| 1534 | E1 | 3-OCH₃ | H | H | 1 | CH₃ | H | 2-CH₃ | 1 | O | O | CH₃ |
| 1535 | E1 | 3-OEt | H | H | 1 | CH₃ | H | 2-CH₃ | 1 | O | O | CH₃ |
| 1536 | E1 | 3-OCF₃ | H | H | 1 | CH₃ | H | 2-CH₃ | 1 | O | O | CH₃ |
| 1537 | E1 | 6-CH₃ | H | H | 1 | CH₃ | H | 2-CH₃ | 1 | O | O | CH₃ |
| 1538 | E1 | 6-Et | H | H | 1 | CH₃ | H | 2-CH₃ | 1 | O | O | CH₃ |
| 1539 | E1 | 6-CF₃ | H | H | 1 | CH₃ | H | 2-CH₃ | 1 | O | O | CH₃ |
| 1540 | E1 | 6-F | H | H | 1 | CH₃ | H | 2-CH₃ | 1 | O | O | CH₃ |
| 1541 | E1 | 6-Cl | H | H | 1 | CH₃ | H | 2-CH₃ | 1 | O | O | CH₃ |
| 1542 | E1 | 6-OCH₃ | H | H | 1 | CH₃ | 11 | 2-CH₃ | 1 | O | O | CH₃ |
| 1543 | E1 | 6-OEt | H | H | 1 | CH₃ | H | 2-CH₃ | 1 | O | O | CH₃ |
| 1544 | E1 | 6-OCF₃ | H | H | 1 | CH₃ | H | 2-CH₃ | 1 | O | O | CH₃ |
| 1545 | E1 | 3,6-diCH₃ | H | H | 1 | CH₃ | H | 2-CH₃ | 1 | O | O | CH₃ |
| 1546 | E1 | 3-Et-6-CH₃ | H | H | 1 | CH₃ | H | 2-CH₃ | 1 | O | O | CH₃ |
| 1547 | E1 | 3-CF₃-6-F | H | H | 1 | CH₃ | H | 2-CH₃ | 1 | O | O | CH₃ |
| 1548 | E1 | 3,6-diF | H | H | 1 | CH₃ | H | 2-CH₃ | 1 | O | O | CH₃ |
| 1549 | E1 | 3-Cl-6-F | H | H | 1 | CH₃ | H | 2-CH₃ | 1 | O | O | CH₃ |
| 1550 | E1 | 3,6-diOCH₃ | H | H | 1 | CH₃ | H | 2-CH₃ | 1 | O | O | CH₃ |
| 1551 | E1 | 3-OEt-6-CH₃ | H | H | 1 | CH₃ | H | 2-CH₃ | 1 | O | O | CH₃ |
| 1552 | E1 | 3-OCF₃-6-F | H | H | 1 | CH₃ | H | 2-CH₃ | 1 | O | O | CH₃ |
| 1553 | E1 | 3-CH₃ | H | CH₃ | 1 | CH₃ | H | 2-CH₃ | 1 | O | O | CH₃ |
| 1554 | E1 | 3-Et | H | CH₃ | 1 | CH₃ | H | 2-CH₃ | 1 | O | O | CH₃ |
| 1555 | E1 | 6-Et | H | CH₃ | 1 | CH₃ | H | 2-CH₃ | 1 | O | O | CH₃ |
| 1556 | E1 | 3-CH₃ | H | Et | 1 | CH₃ | H | 2-CH₃ | 1 | O | O | CH₃ |
| 1557 | E1 | 3-CH₃ | H | i-Pr | 1 | CH₃ | H | 2-CH₃ | 1 | O | O | CH₃ |
| 1558 | E1 | 3-CH₃ | CH₃ | Et | 1 | CH₃ | H | 2-CH₃ | 1 | O | O | CH₃ |
| 1559 | E1 | 3-CH₃ | H | F | 1 | CH₃ | H | 2-CH₃ | 1 | O | O | CH₃ |
| 1560 | E1 | 3-CH₃ | F | F | 1 | CH₃ | H | 2-CH₃ | 1 | O | O | CH₃ |
| 1561 | E1 | 3-CH₃ | H | CF₃ | 1 | CH₃ | H | 2-CH₃ | 1 | O | O | CH₃ |
| 1562 | E1 | 3-CH₃ | H | c-Pr | 1 | CH₃ | H | 2-CH₃ | 1 | O | O | CH₃ |
| 1563 | E1 | 3-CH₃ | —CH2CH2— | | 1 | CH₃ | H | 2-CH₃ | 1 | O | O | CH₃ |
| 1564 | E1 | 3-CH₃ | —CH2CH2OH2— | | 1 | CH₃ | H | 2-CH₃ | 1 | O | O | CH₃ |
| 1565 | E1 | 3-CH₃ | —CH2CH(CH3)— | | 1 | CH₃ | H | 2-CH₃ | 1 | O | O | CH₃ |
| 1566 | E1 | 3-CH₃ | —CH2C(CH3)2— | | 1 | CH₃ | H | 2-CH₃ | 1 | O | O | CH₃ |
| 1567 | E1 | 3-CH₃ | H | H | 1 | H | H | 2-CH₃ | 1 | O | O | CH₃ |
| 1568 | E1 | 3-CH₃ | H | H | 1 | Et | H | 2-CH₃ | 1 | O | O | CH₃ |
| 1569 | E1 | 3-CH₃ | H | H | 1 | c-Pr | H | 2-CH₃ | 1 | O | O | CH₃ |
| 1570 | E1 | 3-CH₃ | H | H | 1 | CH=CH₂ | H | 2-CH₃ | 1 | O | O | CH₃ |
| 1571 | E1 | 3-CH₃ | H | H | 1 | CH₂CH=CH₂ | H | 2-CH₃ | 1 | O | O | CH₃ |
| 1572 | E1 | 3-CH₃ | H | H | 1 | ethynyl | H | 2-CH₃ | 1 | O | O | CH₃ |

TABLE 26-continued

| | | | | | | | | | | | | |
|---|---|---|---|---|---|---|---|---|---|---|---|---|
| 1573 | E1 | 3-CH$_3$ | H | H | 1 | Propargyl | H | 2-CH$_3$ | 1 | O | O | CH$_3$ |
| 1574 | E1 | 3-CH$_3$ | H | H | 1 | CF$_3$ | H | 2-CH$_3$ | 1 | O | O | CH$_3$ |
| 1575 | E1 | 3-CH$_3$ | H | H | 1 | CH=CHCl | H | 2-CH$_3$ | 1 | O | O | CH$_3$ |
| 1576 | E1 | 3-CH$_3$ | H | H | 1 | 3,3,2-tri-Iodo-allyl | H | 2-CH$_3$ | 1 | O | O | CH$_3$ |
| 1577 | E1 | 3-CH$_3$ | H | H | 1 | 3-Iodopropargyl | H | 2-CH$_3$ | 1 | O | O | CH$_3$ |
| 1578 | E1 | 3-CH$_3$ | H | H | 1 | CN | H | 2-CH$_3$ | 1 | O | O | CH$_3$ |
| 1579 | E1 | 3-CH$_3$ | H | H | 1 | CN | H | 2-CH$_3$ | 1 | O | O | CH$_3$ |
| 1580 | E1 | 3-CH$_3$ | H | H | 1 | NO$_2$ | H | 2-CH$_3$ | 1 | O | O | CH$_3$ |
| 1581 | E1 | 3-CH$_3$ | H | H | 1 | NH$_2$ | H | 2-CH$_3$ | 1 | O | O | CH$_3$ |
| 1582 | E1 | 3-CH$_3$ | H | H | 1 | NHCH$_3$ | H | 2-CH$_3$ | 1 | O | O | CH$_3$ |
| 1583 | E1 | 3-CH$_3$ | H | H | 1 | N(CH$_3$)$_2$ | H | 2-CH$_3$ | 1 | O | O | CH$_3$ |
| 1584 | E1 | 3-CH$_3$ | H | H | 1 | CH$_3$ | CH$_3$ | 2-CH$_3$ | 1 | O | O | CH$_3$ |
| 1585 | E1 | 3-CH$_3$ | H | H | 1 | CH$_3$ | Et | 2-CH$_3$ | 1 | O | O | CH$_3$ |
| 1586 | E1 | 3-CH$_3$ | H | H | 1 | CH$_3$ | CH$_3$CO | 2-CH$_3$ | 1 | O | O | CH$_3$ |

TABLE 27

| | | | | | | | | | | | | |
|---|---|---|---|---|---|---|---|---|---|---|---|---|
| 1587 | E1 | 3-CH$_3$ | H | H | 1 | CH$_3$ | CH$_3$CH$_2$CO | 2-CH$_3$ | 1 | O | O | CH$_3$ |
| 1588 | E1 | 3-CH$_3$ | H | H | 1 | CH$_3$ | PhCO | 2-CH$_3$ | 1 | O | O | CH$_3$ |
| 1589 | E1 | 3-CH$_3$ | H | H | 1 | CH$_3$ | 4-Cl-PhCO | 2-CH$_3$ | 1 | O | O | CH$_3$ |
| 1590 | E1 | 3-CH$_3$ | H | H | 1 | CH$_3$ | PhCH$_2$CO | 2-CH$_3$ | 1 | O | O | CH$_3$ |
| 1591 | E1 | 3-CH$_3$ | H | H | 1 | CH$_3$ | CHO | 2-CH$_3$ | 1 | O | O | CH$_3$ |
| 1592 | E1 | 3-CH$_3$ | H | H | 1 | CH$_3$ | CH$_3$OCH$_2$ | 2-CH$_3$ | 1 | O | O | CH$_3$ |
| 1593 | E1 | 3-CH$_3$ | H | H | 1 | CH$_3$ | CH$_3$CH(OCH$_3$) | 2-CH$_3$ | 1 | O | O | CH$_3$ |
| 1594 | E1 | 3-CH$_3$ | H | H | 1 | CH$_3$ | CH$_3$SO$_2$ | 2-CH$_3$ | 1 | O | O | CH$_3$ |
| 1595 | E1 | 3-CH$_3$ | H | H | 1 | CH$_3$ | PhSO$_2$ | 2-CH$_3$ | 1 | O | O | CH$_3$ |
| 1596 | E1 | 3-CH$_3$ | H | H | 1 | CH$_3$ | 4-CH$_3$-PhSO$_2$ | 2-CH$_3$ | 1 | O | O | CH$_3$ |
| 1597 | E1 | 3-CH$_3$ | H | H | 1 | CH$_3$ | H | 2-CH$_3$ | 1 | S | O | CH$_3$ |
| 1598 | E1 | 3-CH$_3$ | H | H | 1 | CH$_3$ | H | 2-CH$_3$ | 1 | O | S | CH$_3$ |
| 1599 | E1 | 3-CH$_3$ | H | H | 1 | CH$_3$ | H | 2-CH$_3$ | 1 | O | — | CH$_3$ |
| 1600 | E1 | 3-CH$_3$ | H | H | 1 | CH$_3$ | H | 2-CH$_3$ | 1 | O | NH | CH$_3$ |
| 1601 | E1 | 3-CH$_3$ | H | H | 1 | CH$_3$ | H | 2-CH$_3$ | 1 | O | NCH$_3$ | CH$_3$ |
| 1602 | E1 | 3-CH$_3$ | H | H | 1 | CH$_3$ | H | 2-CH$_3$ | 1 | O | O | H |
| 1603 | E1 | 3-CH$_3$ | H | H | 1 | CH$_3$ | H | 2-CH$_3$ | 1 | O | O | Et |
| 1604 | E1 | 3-CH$_3$ | H | H | 1 | CH$_3$ | H | 2-CH$_3$ | 1 | O | O | n-Pr |
| 1605 | E1 | 3-CH$_3$ | H | H | 1 | CH$_3$ | H | 2-CH$_3$ | 1 | O | O | CH$_2$CH=CH$_2$ |
| 1606 | E1 | 3-CH$_3$ | H | H | 1 | CH$_3$ | H | 2-CH$_3$ | 1 | O | O | CH=CH$_2$ |
| 1607 | E1 | 3-CH$_3$ | H | H | 1 | CH$_3$ | H | 2-CH$_3$ | 1 | O | O | Propargyl |
| 1608 | E1 | 3-CH$_3$ | H | H | 1 | CH$_3$ | H | 2-CH$_3$ | 1 | O | O | ethynyl |
| 1609 | E1 | 3-CH$_3$ | H | H | 1 | CH$_3$ | H | 2-CH$_3$ | 1 | O | O | CF$_3$ |
| 1610 | E1 | 3-CH$_3$ | H | H | 1 | CH$_3$ | H | 2-CH$_3$ | 1 | O | O | CH$_2$CF$_3$ |
| 1611 | E1 | 3-CH$_3$ | H | H | 1 | CH$_3$ | H | 2-CH$_3$ | 1 | O | O | CF$_2$CF$_3$ |
| 1612 | E1 | 3-CH$_3$ | H | H | 1 | CH$_3$ | H | 2-CH$_3$ | 1 | O | O | CF$_2$CF$_2$H |
| 1613 | E1 | 3-CH$_3$ | H | H | 1 | CH$_3$ | H | 2-CH$_3$ | 1 | O | O | CH$_2$CH=CHCl |
| 1614 | E1 | 3-CH$_3$ | H | H | 1 | CH$_3$ | H | 2-CH$_3$ | 1 | O | O | 3-Iodo-propargyl |
| 1615 | E1 | 3-CH$_3$ | H | H | 1 | CH$_3$ | H | 2-CH$_3$ | 1 | O | O | c-Pr |
| 1616 | E1 | 3-CH$_3$ | H | H | 1 | CH$_3$ | H | 2-CH$_3$ | 1 | O | O | c-Hex |
| 1617 | E1 | 3-CH$_3$ | H | H | 1 | CH$_3$ | H | 2-CH$_3$ | 1 | O | O | 2-CH$_3$-c-Pr |
| 1618 | E2 | — | H | H | 1 | CH$_3$ | H | — | 0 | O | O | CH$_3$ |
| 1619 | E2 | — | H | H | 1 | CH$_3$ | H | 2-Cl | 1 | O | O | CH$_3$ |
| 1620 | E2 | 4-CH$_3$ | H | H | 1 | CH$_3$ | H | 2-Cl | 1 | O | O | CH$_3$ |
| 1621 | E2 | 4-Et | H | H | 1 | CH$_3$ | H | 2-Cl | 1 | O | O | CH$_3$ |
| 1622 | E2 | 4-CF$_3$ | H | H | 1 | CH$_3$ | H | 2-Cl | 1 | O | O | CH$_3$ |
| 1623 | E2 | 4-F | H | H | 1 | CH$_3$ | H | 2-Cl | 1 | O | O | CH$_3$ |
| 1624 | E2 | 4-Cl | H | H | 1 | CH$_3$ | H | 2-Cl | 1 | O | O | CH$_3$ |
| 1625 | E2 | 4-OCH$_3$ | H | H | 1 | CH$_3$ | H | 2-Cl | 1 | O | O | CH$_3$ |
| 1626 | E2 | 4-OEt | H | H | 1 | CH$_3$ | H | 2-Cl | 1 | O | O | CH$_3$ |
| 1627 | E2 | 4-OCF$_3$ | H | H | 1 | CH$_3$ | H | 2-Cl | 1 | O | O | CH$_3$ |
| 1628 | E2 | 6-CH$_3$ | H | H | 1 | CH$_3$ | H | 2-Cl | 1 | O | O | CH$_3$ |
| 1629 | E2 | 6-Et | H | H | 1 | CH$_3$ | H | 2-Cl | 1 | O | O | CH$_3$ |
| 1630 | E2 | 6-CF$_3$ | H | H | 1 | CH$_3$ | H | 2-Cl | 1 | O | O | CH$_3$ |
| 1631 | E2 | 6-F | H | H | 1 | CH$_3$ | H | 2-Cl | 1 | O | O | CH$_3$ |
| 1632 | E2 | 6-Cl | H | H | 1 | CH$_3$ | H | 2-Cl | 1 | O | O | CH$_3$ |
| 1633 | E2 | 6-OCH$_3$ | H | H | 1 | CH$_3$ | H | 2-Cl | 1 | O | O | CH$_3$ |
| 1634 | E2 | 6-OEt | H | H | 1 | CH$_3$ | H | 2-Cl | 1 | O | O | CH$_3$ |
| 1635 | E2 | 6-OCF$_3$ | H | H | 1 | CH$_3$ | H | 2-Cl | 1 | O | O | CH$_3$ |
| 1636 | E2 | 4,6-diCH$_3$ | H | H | 1 | CH$_3$ | H | 2-Cl | 1 | O | O | CH$_3$ |
| 1637 | E2 | 4-Et-6-CH$_3$ | H | H | 1 | CH$_3$ | H | 2-Cl | 1 | O | O | CH$_3$ |
| 1638 | E2 | 4-CF$_3$-6-F | 14 | H | 1 | CH$_3$ | H | 2-Cl | 1 | O | O | CH$_3$ |
| 1639 | E2 | 4,6-diF | H | H | 1 | CH$_3$ | H | 2-Cl | 1 | O | O | CH$_3$ |
| 1640 | E2 | 4-Cl-6-F | H | H | 1 | CH$_3$ | H | 2-Cl | 1 | O | O | CH$_3$ |
| 1641 | E2 | 4,6-diOCH$_3$ | H | H | 1 | CH$_3$ | H | 2-Cl | 1 | O | O | CH$_3$ |
| 1642 | E2 | 4-OEt-6-CH$_3$ | H | H | 1 | CH$_3$ | H | 2-Cl | 1 | O | O | CH$_3$ |
| 1643 | E2 | 4-OCF$_3$-6-F | H | H | 1 | CH$_3$ | H | 2-Cl | 1 | O | O | CH$_3$ |
| 1644 | E2 | 4-CH$_3$ | H | CH$_3$ | 1 | CH$_3$ | H | 2-Cl | 1 | O | O | CH$_3$ |
| 1645 | E2 | 4-Et | H | CH$_3$ | 1 | CH$_3$ | H | 2-Cl | 1 | O | O | CH$_3$ |
| 1646 | E2 | 6-Et | H | CH$_3$ | 1 | CH$_3$ | H | 2-Cl | 1 | O | O | CH$_3$ |

TABLE 27-continued

| | | | | | | | | | | | |
|---|---|---|---|---|---|---|---|---|---|---|---|
| 1647 | E2 | 6-Cl | H | CH₃ | 1 CH₃ | H | 2-Cl | 1 | O | O | CH₃ |
| 1648 | E2 | 6-Cl | H | Et | 1 CH₃ | H | 2-Cl | 1 | O | O | CH₃ |

TABLE 28

| | | | | | | | | | | | |
|---|---|---|---|---|---|---|---|---|---|---|---|
| 1649 | E2 | 6-Cl | H | i-Pr | 1 CH₃ | H | 2-Cl | 1 | O | O | CH₃ |
| 1650 | E2 | 4-CH₃ | H | Et | 1 CH₃ | H | 2-Cl | 1 | O | O | CH₃ |
| 1651 | E2 | 4-CH₃ | H | i-Pr | 1 CH₃ | H | 2-Cl | 1 | O | O | CH₃ |
| 1652 | E2 | 4-CH₃ | CH₃ | Et | 1 CH₃ | H | 2-Cl | 1 | O | O | CH₃ |
| 1653 | E2 | 4-CH₃ | H | F | 1 CH₃ | H | 2-Cl | 1 | O | O | CH₃ |
| 1654 | E2 | 4-CH₃ | F | F | 1 CH₃ | H | 2-Cl | 1 | O | O | CH₃ |
| 1655 | E2 | 4-CH₃ | H | CF₃ | 1 CH₃ | H | 2-Cl | 1 | O | O | CH₃ |
| 1656 | E2 | 4-CH₃ | H | c-Pr | 1 CH₃ | H | 2-Cl | 1 | O | O | CH₃ |
| 1657 | E2 | 4-CH₃ | —CH2CH2— | | 1 CH₃ | H | 2-Cl | 1 | O | O | CH₃ |
| 1658 | E2 | 4-CH₃ | —CH2CH2CH2— | | 1 CH₃ | H | 2-Cl | 1 | O | O | CH₃ |
| 1659 | E2 | 4-CH₃ | —CH2CH(CH3)— | | 1 CH₃ | H | 2-Cl | 1 | O | O | CH₃ |
| 1660 | E2 | 4-CH₃ | —CH2C(CH3)2— | | 1 CH₃ | H | 2-Cl | 1 | O | O | CH₃ |
| 1661 | E2 | 4-CH₃ | H | H | 1 H | H | 2-Cl | 1 | O | O | CH₃ |
| 1662 | E2 | 4-CH₃ | H | H | 1 Et | H | 2-Cl | 1 | O | O | CH₃ |
| 1663 | E2 | 4-CH₃ | H | H | 1 c-Pr | H | 2-Cl | 1 | O | O | CH₃ |
| 1664 | E2 | 4-CH₃ | H | H | 1 CH=CH₂ | H | 2-Cl | 1 | O | O | CH₃ |
| 1665 | E2 | 4-CH₃ | H | H | 1 CH₂CH=CH₂ | H | 2-Cl | 1 | O | O | CH₃ |
| 1666 | E2 | 4-CH₃ | H | H | 1 ethynyl | H | 2-Cl | 1 | O | O | CH₃ |
| 1667 | E2 | 4-CH₃ | H | H | 1 Propargyl | H | 2-Cl | 1 | O | O | CH₃ |
| 1668 | E2 | 4-CH₃ | H | H | 1 CF₃ | H | 2-Cl | 1 | O | O | CH₃ |
| 1669 | E2 | 4-CH₃ | H | H | 1 CH=CHCl | H | 2-Cl | 1 | O | O | CH₃ |
| 1670 | E2 | 4-CH₃ | H | H | 1 3,3,2-tri-Iodo-allyl | H | 2-Cl | 1 | O | O | CH₃ |
| 1671 | E2 | 4-CH₃ | H | H | 1 3-Iodopropargyl | H | 2-Cl | 1 | O | O | CH₃ |
| 1672 | E2 | 4-CH₃ | H | H | 1 CN | H | 2-Cl | 1 | O | O | CH₃ |
| 1673 | E2 | 4-CF₃ | H | H | 1 CN | H | 2-Cl | 1 | O | O | CH₃ |
| 1674 | E2 | 4-CH₃ | H | H | 1 NO₂ | H | 2-Cl | 1 | O | O | CH₃ |
| 1675 | E2 | 4-CH₃ | H | H | 1 NH₂ | H | 2-Cl | 1 | O | O | CH₃ |
| 1676 | E2 | 4-CH₃ | H | H | 1 NHCH₃ | H | 2-Cl | 1 | O | O | CH₃ |
| 1677 | E2 | 4-CH₃ | H | H | 1 N(CH₃)₂ | H | 2-Cl | 1 | O | O | CH₃ |
| 1678 | E2 | 4-CH₃ | H | H | 1 CH₃ | CH₃ | 2-Cl | 1 | O | O | CH₃ |
| 1679 | E2 | 4-CH₃ | H | H | 1 CH₃ | Et | 2-Cl | 1 | O | O | CH₃ |
| 1680 | E2 | 4-CH₃ | H | H | 1 CH₃ | CH₃CO | 2-Cl | 1 | O | O | CH₃ |
| 1681 | E2 | 4-CH₃ | H | H | 1 CH₃ | CH₃CH₂CO | 2-Cl | 1 | O | O | CH₃ |
| 1682 | E2 | 4-CH₃ | H | H | 1 CH₃ | PhCO | 2-Cl | 1 | O | O | CH₃ |
| 1683 | E2 | 4-CH₃ | H | H | 1 CH₃ | 4-Cl-PhCO | 2-Cl | 1 | O | O | CH₃ |
| 1684 | E2 | 4-CH₃ | H | H | 1 CH₃ | PhCH₂CO | 2-Cl | 1 | O | O | CH₃ |
| 1685 | E2 | 4-CH₃ | H | H | 1 CH₃ | CHO | 2-Cl | 1 | O | O | CH₃ |
| 1686 | E2 | 4-CH₃ | H | H | 1 CH₃ | CH₃OCH₂ | 2-Cl | 1 | O | O | CH₃ |
| 1687 | E2 | 4-CH₃ | H | H | 1 CH₃ | CH₃CH(OCH₃) | 2-Cl | 1 | O | O | CH₃ |
| 1688 | E2 | 4-CH₃ | H | H | 1 CH₃ | CH₃SO₂ | 2-Cl | 1 | O | O | CH₃ |
| 1689 | E2 | 4-CH₃ | H | H | 1 CH₃ | PhSO₂ | 2-Cl | 1 | O | O | CH₃ |
| 1690 | E2 | 4-CH₃ | H | H | 1 CH₃ | 4-CH₃-PhSO₂ | 2-Cl | 1 | O | O | CH₃ |
| 1691 | E2 | 4-CH₃ | H | H | 1 CH₃ | H | 2-Cl | 1 | S | O | CH₃ |
| 1692 | E2 | 4-CH₃ | H | H | 1 CH₃ | H | 2-Cl | 1 | O | S | CH₃ |
| 1693 | E2 | 4-CH₃ | H | H | 1 CH₃ | H | 2-Cl | 1 | O | — | CH₃ |
| 1694 | E2 | 4-CH₃ | H | H | 1 CH₃ | H | 2-Cl | 1 | O | NH | CH₃ |
| 1695 | E2 | 4-CH₃ | H | H | 1 CH₃ | H | 2-Cl | 1 | O | NCH₃ | CH₃ |
| 1696 | E2 | 4-CH₃ | H | H | 1 CH₃ | H | 2-Cl | 1 | O | O | H |
| 1697 | E2 | 4-CH₃ | H | H | 1 CH₃ | H | 2-Cl | 1 | O | O | Et |
| 1698 | E2 | 4-CH₃ | H | H | 1 CH₃ | H | 2-Cl | 1 | O | O | n-Pr |
| 1699 | E2 | 4-CH₃ | H | H | 1 CH₃ | H | 2-Cl | 1 | O | O | CH₂CH=CH₂ |
| 1700 | E2 | 4-CH₃ | H | H | 1 CH₃ | H | 2-Cl | 1 | O | O | CH=CH₂ |
| 1701 | E2 | 4-CH₃ | H | H | 1 CH₃ | H | 2-Cl | 1 | O | O | Propargyl |
| 1702 | E2 | 4-CH₃ | H | H | 1 CH₃ | H | 2-Cl | 1 | O | O | ethynyl |
| 1703 | E2 | 4-CH₃ | H | H | 1 CH₃ | H | 2-Cl | 1 | O | O | CF₃ |
| 1704 | E2 | 4-CH₃ | H | H | 1 CH₃ | H | 2-Cl | 1 | O | O | CH₂CF₃ |
| 1705 | E2 | 4-CH₃ | H | H | 1 CH₃ | H | 2-Cl | 1 | O | O | CF₂CF₃ |
| 1706 | E2 | 4-CH₃ | H | H | 1 CH₃ | H | 2-Cl | 1 | O | O | CF₂CF₂H |
| 1707 | E2 | 4-CH₃ | H | H | 1 CH₃ | H | 2-Cl | 1 | O | O | CH₂CH=CHCl |
| 1708 | E2 | 4-CH₃ | H | H | 1 CH₃ | H | 2-Cl | 1 | O | O | 3-Iodo-propargyl |
| 1709 | E2 | 4-CH₃ | H | H | 1 CH₃ | H | 2-Cl | 1 | O | O | c-Pr |
| 1710 | E2 | 4-CH₃ | H | H | 1 CH₃ | H | 2-Cl | 1 | O | O | c-Hex |

TABLE 29

| | | | | | | | | | | | |
|---|---|---|---|---|---|---|---|---|---|---|---|
| 1711 | E2 | 4-CH₃ | H | H | 1 CH₃ | H | 2-Cl | 1 | O | O | 2-CH₃-c-Pr |
| 1712 | E2 | — | H | H | 1 CH₃ | H | 2-CH₃ | 1 | O | O | CH₃ |
| 1713 | E2 | 4-CH₃ | H | H | 1 CH₃ | H | 2-CH₃ | 1 | O | O | CH₃ |
| 1714 | E2 | 4-Et | H | H | 1 CH₃ | H | 2-CH₃ | 1 | O | O | CH₃ |
| 1715 | E2 | 4-CF₃ | H | H | 1 CH₃ | H | 2-CH₃ | 1 | O | O | CH₃ |

TABLE 29-continued

| No. | Type | | | | | | | | | | |
|---|---|---|---|---|---|---|---|---|---|---|---|
| 1716 | E2 | 4-F | H | H | 1 | CH₃ | H | 2-CH₃ | 1 | O | O | CH₃ |
| 1717 | E2 | 4-Cl | H | H | 1 | CH₃ | H | 2-CH₃ | 1 | O | O | CH₃ |
| 1718 | E2 | 4-OCH₃ | H | H | 1 | CH₃ | H | 2-CH₃ | 1 | O | O | CH₃ |
| 1719 | E2 | 4-OEt | H | H | 1 | CH₃ | H | 2-CH₃ | 1 | O | O | CH₃ |
| 1720 | E2 | 4-OCF₃ | H | H | 1 | CH₃ | H | 2-CH₃ | 1 | O | O | CH₃ |
| 1721 | E2 | 6-CH₃ | H | H | 1 | CH₃ | H | 2-CH₃ | 1 | O | O | CH₃ |
| 1722 | E2 | 6-Et | H | H | 1 | CH₃ | H | 2-CH₃ | 1 | O | O | CH₃ |
| 1723 | E2 | 6-CF₃ | H | H | 1 | CH₃ | H | 2-CH₃ | 1 | O | O | CH₃ |
| 1724 | E2 | 6-F | H | H | 1 | CH₃ | H | 2-CH₃ | 1 | O | O | CH₃ |
| 1725 | E2 | 6-Cl | H | H | 1 | CH₃ | H | 2-CH₃ | 1 | O | O | CH₃ |
| 1726 | E2 | 6-OCH₃ | H | H | 1 | CH₃ | H | 2-CH₃ | 1 | O | O | CH₃ |
| 1727 | E2 | 6-OEt | H | H | 1 | CH₃ | H | 2-CH₃ | 1 | O | O | CH₃ |
| 1728 | E2 | 6-OCF₃ | H | H | 1 | CH₃ | H | 2-CH₃ | 1 | O | O | CH₃ |
| 1729 | E2 | 4,6-diCH₃ | H | H | 1 | CH₃ | H | 2-CH₃ | 1 | O | O | CH₃ |
| 1730 | E2 | 4-Et-6-CH₃ | H | H | 1 | CH₃ | H | 2-CH₃ | 1 | O | O | CH₃ |
| 1731 | E2 | 4-CF₃-6-F | H | H | 1 | CH₃ | H | 2-CH₃ | 1 | O | O | CH₃ |
| 1732 | E2 | 4,6-diF | H | H | 1 | CH₃ | H | 2-CH₃ | 1 | O | O | CH₃ |
| 1733 | E2 | 4-Cl-6-F | H | H | 1 | CH₃ | H | 2-CH₃ | 1 | O | O | CH₃ |
| 1734 | E2 | 4,6-diOCH₃ | H | H | 1 | CH₃ | H | 2-CH₃ | 1 | O | O | CH₃ |
| 1735 | E2 | 4-OEt-6-CH₃ | H | H | 1 | CH₃ | H | 2-CH₃ | 1 | O | O | CH₃ |
| 1736 | E2 | 4-OCF₃-6-F | H | H | 1 | CH₃ | H | 2-CH₃ | 1 | O | O | CH₃ |
| 1737 | E2 | 4-CH₃ | H | CH₃ | 1 | CH₃ | H | 2-CH₃ | 1 | O | O | CH₃ |
| 1738 | E2 | 4-Et | H | CH₃ | 1 | CH₃ | H | 2-CH₃ | 1 | O | O | CH₃ |
| 1739 | E2 | 6-Et | H | CH₃ | 1 | CH₃ | H | 2-CH₃ | 1 | O | O | CH₃ |
| 1740 | E2 | 4-CH₃ | H | Et | 1 | CH₃ | H | 2-CH₃ | 1 | O | O | CH₃ |
| 1741 | E2 | 4-CH₃ | H | i-Pr | 1 | CH₃ | H | 2-CH₃ | 1 | O | O | CH₃ |
| 1742 | E2 | 4-CH₃ | CH₃ | Et | 1 | CH₃ | H | 2-CH₃ | 1 | O | O | CH₃ |
| 1743 | E2 | 4-CH₃ | H | F | 1 | CH₃ | H | 2-CH₃ | 1 | O | O | CH₃ |
| 1744 | E2 | 4-CH₃ | F | F | 1 | CH₃ | H | 2-CH₃ | 1 | O | O | CH₃ |
| 1745 | E2 | 4-CH₃ | H | CF₃ | 1 | CH₃ | H | 2-CH₃ | 1 | O | O | CH₃ |
| 1746 | E2 | 4-CH₃ | H | c-Pr | 1 | CH₃ | H | 2-CH₃ | 1 | O | O | CH₃ |
| 1747 | E2 | 4-CH₃ | —CH2CH2— | | 1 | CH₃ | H | 2-CH₃ | 1 | O | O | CH₃ |
| 1748 | E2 | 4-CH₃ | —CH2CH2CH2— | | 1 | CH₃ | H | 2-CH₃ | 1 | O | O | CH₃ |
| 1749 | E2 | 4-CH₃ | —CH2CH(CH3)— | | 1 | CH₃ | H | 2-CH₃ | 1 | O | O | CH₃ |
| 1750 | E2 | 4-CH₃ | —CH2C(CH3)2— | | 1 | CH₃ | H | 2-CH₃ | 1 | O | O | CH₃ |
| 1751 | E2 | 4-CH₃ | H | H | 1 | H | H | 2-CH₃ | 1 | O | O | CH₃ |
| 1752 | E2 | 4-CH₃ | H | H | 1 | Et | H | 2-CH₃ | 1 | O | O | CH₃ |
| 1753 | E2 | 4-CH₃ | H | H | 1 | c-Pr | H | 2-CH₃ | 1 | O | O | CH₃ |
| 1754 | E2 | 4-CH₃ | H | H | 1 | CH=CH₂ | H | 2-CH₃ | 1 | O | O | CH₃ |
| 1755 | E2 | 4-CH₃ | H | H | 1 | CH₂CH=CH₂ | H | 2-CH₃ | 1 | O | O | CH₃ |
| 1756 | E2 | 4-CH₃ | H | H | 1 | ethynyl | H | 2-CH₃ | 1 | O | O | CH₃ |
| 1757 | E2 | 4-CH₃ | H | H | 1 | Propargyl | H | 2-CH₃ | 1 | O | O | CH₃ |
| 1758 | E2 | 4-CH₃ | H | H | 1 | CF₃ | H | 2-CH₃ | 1 | O | O | CH₃ |
| 1759 | E2 | 4-CH₃ | H | H | 1 | CH=CHCl | H | 2-CH₃ | 1 | O | O | CH₃ |
| 1760 | E2 | 4-CH₃ | H | H | 1 | 3,3,2-tri-Iodo-allyl | H | 2-CH₃ | 1 | O | O | CH₃ |
| 1761 | E2 | 4-CH₃ | H | H | 1 | 3-Iodopropargyl | H | 2-CH₃ | 1 | O | O | CH₃ |
| 1762 | E2 | 4-CH₃ | H | H | 1 | CN | H | 2-CH₃ | 1 | O | O | CH₃ |
| 1763 | E2 | 4-CH₃ | H | H | 1 | CN | H | 2-CH₃ | 1 | O | O | CH₃ |
| 1764 | E2 | 4-CH₃ | H | H | 1 | NO₂ | H | 2-CH₃ | 1 | O | O | CH₃ |
| 1765 | E2 | 4-CH₃ | H | H | 1 | NH₂ | H | 2-CH₃ | 1 | O | O | CH₃ |
| 1766 | E2 | 4-CH₃ | H | H | 1 | NHCH₃ | H | 2-CH₃ | 1 | O | O | CH₃ |
| 1767 | E2 | 4-CH₃ | H | H | 1 | N(CH₃)₂ | H | 2-CH₃ | 1 | O | O | CH₃ |
| 1768 | E2 | 4-CH₃ | H | H | 1 | CH₃ | CH₃ | 2-CH₃ | 1 | O | O | CH₃ |
| 1769 | E2 | 4-CH₃ | H | H | 1 | CH₃ | Et | 2-CH₃ | 1 | O | O | CH₃ |
| 1770 | E2 | 4-CH₃ | H | H | 1 | CH₃ | CH₃CO | 2-CH₃ | 1 | O | O | CH₃ |
| 1771 | E2 | 4-CH₃ | H | H | 1 | CH₃ | CH₃CH₂CO | 2-CH₃ | 1 | O | O | CH₃ |
| 1772 | E2 | 4-CH₃ | H | H | 1 | CH₃ | PhCO | 2-CH₃ | 1 | O | O | CH₃ |

TABLE 30

| No. | Type | | | | | | | | | | |
|---|---|---|---|---|---|---|---|---|---|---|---|
| 1773 | E2 | 4-CH₃ | H | H | 1 | CH₃ | 4-Cl-PhCO | 2-CH₃ | 1 | O | O | CH₃ |
| 1774 | E2 | 4-CH₃ | H | H | 1 | CH₃ | PhCH₂CO | 2-CH₃ | 1 | O | O | CH₃ |
| 1775 | E2 | 4-CH₃ | H | H | 1 | CH₃ | CHO | 2-CH₃ | 1 | O | O | CH₃ |
| 1776 | E2 | 4-CH₃ | H | H | 1 | CH₃ | CH₃OCH₂ | 2-CH₃ | 1 | O | O | CH₃ |
| 1777 | E2 | 4-CH₃ | H | H | 1 | CH₃ | CH₃CH(OCH₃) | 2-CH₃ | 1 | O | O | CH₃ |
| 1778 | E2 | 4-CH₃ | H | H | 1 | CH₃ | CH₃SO₂ | 2-CH₃ | 1 | O | O | CH₃ |
| 1779 | E2 | 4-CH₃ | H | H | 1 | CH₃ | PhSO₂ | 2-CH₃ | 1 | O | O | CH₃ |
| 1780 | E2 | 4-CH₃ | H | H | 1 | CH₃ | 4-CH₃-PhSO₂ | 2-CH₃ | 1 | O | O | CH₃ |
| 1781 | E2 | 4-CH₃ | H | H | 1 | CH₃ | H | 2-CH₃ | 1 | S | O | CH₃ |
| 1782 | E2 | 4-CH₃ | H | H | 1 | CH₃ | H | 2-CH₃ | 1 | O | S | CH₃ |
| 1783 | E2 | 4-CH₃ | H | H | 1 | CH₃ | H | 2-CH₃ | 1 | O | — | CH₃ |
| 1784 | E2 | 4-CH₃ | H | H | 1 | CH₃ | H | 2-CH₃ | 1 | O | NH | CH₃ |
| 1785 | E2 | 4-CH₃ | H | H | 1 | CH₃ | H | 2-CH₃ | 1 | O | NCH₃ | CH₃ |
| 1786 | E2 | 4-CH₃ | H | H | 1 | CH₃ | H | 2-CH₃ | 1 | O | O | H |
| 1787 | E2 | 4-CH₃ | H | H | 1 | CH₃ | H | 2-CH₃ | 1 | O | O | Et |
| 1788 | E2 | 4-CH₃ | H | H | 1 | CH₃ | H | 2-CH₃ | 1 | O | O | n-Pr |
| 1789 | E2 | 4-CH₃ | H | H | 1 | CH₃ | H | 2-CH₃ | 1 | O | O | CH₂CH=CH₂ |

TABLE 30-continued

| | | | | | | | | | | | |
|---|---|---|---|---|---|---|---|---|---|---|---|
| 1790 | E2 | 4-CH₃ | H | H | 1 CH₃ | H | 2-CH₃ | 1 | O | O | CH=CH₂ |
| 1791 | E2 | 4-CH₃ | H | H | 1 CH₃ | H | 2-CH₃ | 1 | O | O | Propargyl |
| 1792 | E2 | 4-CH₃ | H | H | 1 CH₃ | H | 2-CH₃ | 1 | O | O | ethynyl |
| 1793 | E2 | 4-CH₃ | H | H | 1 CH₃ | H | 2-CH₃ | 1 | O | O | CF₃ |
| 1794 | E2 | 4-CH₃ | H | H | 1 CH₃ | H | 2-CH₃ | 1 | O | O | CH₂CF₃ |
| 1795 | E2 | 4-CH₃ | H | H | 1 CH₃ | H | 2-CH₃ | 1 | O | O | CF₂CF₃ |
| 1796 | E2 | 4-CH₃ | H | H | 1 CH₃ | H | 2-CH₃ | 1 | O | O | CF₂CF₂H |
| 1797 | E2 | 4-CH₃ | H | H | 1 CH₃ | H | 2-CH₃ | 1 | O | O | CH₂CH=CHCl |
| 1798 | E2 | 4-CH₃ | H | H | 1 CH₃ | H | 2-CH₃ | 1 | O | O | 3-Iodo-propargyl |
| 1799 | E2 | 4-CH₃ | H | H | 1 CH₃ | H | 2-CH₃ | 1 | O | O | c-Pr |
| 1800 | E2 | 4-CH₃ | H | H | 1 CH₃ | H | 2-CH₃ | 1 | O | O | c-Hex |
| 1801 | E2 | 4-CH₃ | H | H | 1 CH₃ | H | 2-CH₃ | 1 | O | O | 2-CH₃-c-Pr |
| 1802 | E3 | — | H | H | 1 CH₃ | H | — | 0 | O | O | CH₃ |
| 1803 | E3 | — | H | H | 1 CH₃ | H | 2-Cl | 1 | O | O | CH₃ |
| 1804 | E3 | 3-CH₃ | H | H | 1 CH₃ | H | 2-Cl | 1 | O | O | CH₃ |
| 1805 | E3 | 3-Et | H | H | 1 CH₃ | H | 2-Cl | 1 | O | O | CH₃ |
| 1806 | E3 | 3-CF₃ | H | H | 1 CH₃ | H | 2-Cl | 1 | O | O | CH₃ |
| 1807 | E3 | 3-F | H | H | 1 CH₃ | H | 2-Cl | 1 | O | O | CH₃ |
| 1808 | E3 | 3-Cl | H | H | 1 CH₃ | H | 2-Cl | 1 | O | O | CH₃ |
| 1809 | E3 | 3-OCH₃ | H | H | 1 CH₃ | H | 2-Cl | 1 | O | O | CH₃ |
| 1810 | E3 | 3-OEt | H | H | 1 CH₃ | H | 2-Cl | 1 | O | O | CH₃ |
| 1811 | E3 | 3-OCF₃ | H | H | 1 CH₃ | H | 2-Cl | 1 | O | O | CH₃ |
| 1812 | E3 | 6-CH₃ | H | H | 1 CH₃ | H | 2-Cl | 1 | O | O | CH₃ |
| 1813 | E3 | 6-Et | H | H | 1 CH₃ | H | 2-Cl | 1 | O | O | CH₃ |
| 1814 | E3 | 6-CF₃ | H | H | 1 CH₃ | H | 2-Cl | 1 | O | O | CH₃ |
| 1815 | E3 | 6-F | H | H | 1 CH₃ | H | 2-Cl | 1 | O | O | CH₃ |
| 1816 | E3 | 6-Cl | H | H | 1 CH₃ | H | 2-Cl | 1 | O | O | CH₃ |
| 1817 | E3 | 6-OCH₃ | H | H | 1 CH₃ | H | 2-Cl | 1 | O | O | CH₃ |
| 1818 | E3 | 6-OEt | H | H | 1 CH₃ | H | 2-Cl | 1 | O | O | CH₃ |
| 1819 | E3 | 6-OCF₃ | H | H | 1 CH₃ | H | 2-Cl | 1 | O | O | CH₃ |
| 1820 | E3 | 3,6-diCH₃ | H | H | 1 CH₃ | H | 2-Cl | 1 | O | O | CH₃ |
| 1821 | E3 | 3-Et-6-CH₃ | H | H | 1 CH₃ | H | 2-Cl | 1 | O | O | CH₃ |
| 1822 | E3 | 3-CF₃-6-F | H | H | 1 CH₃ | H | 2-Cl | 1 | O | O | CH₃ |
| 1823 | E3 | 3,6-diF | H | H | 1 CH₃ | H | 2-Cl | 1 | O | O | CH₃ |
| 1824 | E3 | 3-Cl-6-F | H | H | 1 CH₃ | H | 2-Cl | 1 | O | O | CH₃ |
| 1825 | E3 | 3,6-diOCH₃ | H | H | 1 CH₃ | H | 2-Cl | 1 | O | O | CH₃ |
| 1826 | E3 | 3-OEt-6-CH₃ | H | H | 1 CH₃ | H | 2-Cl | 1 | O | O | CH₃ |
| 1827 | E3 | 3-OCF₃-6-F | H | H | 1 CH₃ | H | 2-Cl | 1 | O | O | CH₃ |
| 1828 | E3 | 3-CH₃ | H | CH₃ | 1 CH₃ | H | 2-Cl | 1 | O | O | CH₃ |
| 1829 | E3 | 3-Et | H | CH₃ | 1 CH₃ | H | 2-Cl | 1 | O | O | CH₃ |
| 1830 | E3 | 6-Et | H | CH₃ | 1 CH₃ | H | 2-Cl | 1 | O | O | CH₃ |
| 1831 | E3 | 6-Cl | H | CH₃ | 1 CH₃ | H | 2-Cl | 1 | O | O | CH₃ |
| 1832 | E3 | 6-Cl | H | Et | 1 CH₃ | H | 2-Cl | 1 | O | O | CH₃ |
| 1833 | E3 | 6-Cl | H | i-Pr | 1 CH₃ | H | 2-Cl | 1 | O | O | CH₃ |
| 1834 | E3 | 3-CH₃ | H | Et | 1 CH₃ | H | 2-Cl | 1 | O | O | CH₃ |

TABLE 31

| | | | | | | | | | | | |
|---|---|---|---|---|---|---|---|---|---|---|---|
| 1835 | E3 | 3-CH₃ | H | i-Pr | 1 CH₃ | H | 2-Cl | 1 | O | O | CH₃ |
| 1836 | E3 | 3-CH₃ | CH₃ | Et | 1 CH₃ | H | 2-Cl | 1 | O | O | CH₃ |
| 1837 | E3 | 3-CH₃ | H | F | 1 CH₃ | H | 2-Cl | 1 | O | O | CH₃ |
| 1838 | E3 | 3-CH₃ | F | F | 1 CH₃ | H | 2-Cl | 1 | O | O | CH₃ |
| 1839 | E3 | 3-CH₃ | H | CF₃ | 1 CH₃ | H | 2-Cl | 1 | O | O | CH₃ |
| 1840 | E3 | 3-CH₃ | H | c-Pr | 1 CH₃ | H | 2-Cl | 1 | O | O | CH₃ |
| 1841 | E3 | 3-CH₃ | —CH2CH2— | | 1 CH₃ | H | 2-Cl | 1 | O | O | CH₃ |
| 1842 | E3 | 3-CH₃ | —CH2CH2CH2— | | 1 CH₃ | H | 2-Cl | 1 | O | O | CH₃ |
| 1843 | E3 | 3-CH₃ | —CH2CH(CH3)— | | 1 CH₃ | H | 2-Cl | 1 | O | O | CH₃ |
| 1844 | E3 | 3-CH₃ | —CH2C(CH3)2— | | 1 CH₃ | H | 2-Cl | 1 | O | O | CH₃ |
| 1845 | E3 | 3-CH₃ | H | H | 1 H | H | 2-Cl | 1 | O | O | CH₃ |
| 1846 | E3 | 3-CH₃ | H | H | 1 Et | H | 2-Cl | 1 | O | O | CH₃ |
| 1847 | E3 | 3-CH₃ | H | H | 1 c-Pr | H | 2-Cl | 1 | O | O | CH₃ |
| 1848 | E3 | 3-CH₃ | H | H | 1 CH=CH₂ | H | 2-Cl | 1 | O | O | CH₃ |
| 1849 | E3 | 3-CH₃ | H | H | 1 CH₂CH=CH₂ | H | 2-Cl | 1 | O | O | CH₃ |
| 1850 | E3 | 3-CH₃ | H | H | 1 ethynyl | H | 2-Cl | 1 | O | O | CH₃ |
| 1851 | E3 | 3-CH₃ | H | H | 1 Propargyl | H | 2-Cl | 1 | O | O | CH₃ |
| 1852 | E3 | 3-CH₃ | H | H | 1 CF₃ | H | 2-Cl | 1 | O | O | CH₃ |
| 1853 | E3 | 3-CH₃ | H | H | 1 CH=CHCl | H | 2-Cl | 1 | O | O | CH₃ |
| 1854 | E3 | 3-CH₃ | H | H | 1 3,3,2-tri-Iodo-allyl | H | 2-Cl | 1 | O | O | CH₃ |
| 1855 | E3 | 3-CH₃ | H | H | 1 3-Iodopropargyl | H | 2-Cl | 1 | O | O | CH₃ |
| 1856 | E3 | 3-CH₃ | H | H | 1 CN | H | 2-Cl | 1 | O | O | CH₃ |
| 1857 | E3 | 3-CF₃ | H | H | 1 CN | H | 2-Cl | 1 | O | O | CH₃ |
| 1858 | E3 | 3-CH₃ | H | H | 1 NO₂ | H | 2-Cl | 1 | O | O | CH₃ |
| 1859 | E3 | 3-CH₃ | H | H | 1 NH₂ | H | 2-Cl | 1 | O | O | CH₃ |
| 1860 | E3 | 3-CH₃ | H | H | 1 NHCH₃ | H | 2-Cl | 1 | O | O | CH₃ |
| 1861 | E3 | 3-CH₃ | H | H | 1 N(CH₃)₂ | H | 2-Cl | 1 | O | O | CH₃ |
| 1862 | E3 | 3-CH₃ | H | H | 1 CH₃ | CH₃ | 2-Cl | 1 | O | O | CH₃ |
| 1863 | E3 | 3-CH₃ | H | H | 1 CH₃ | Et | 2-Cl | 1 | O | O | CH₃ |

TABLE 31-continued

| | | | | | | | | | | | |
|---|---|---|---|---|---|---|---|---|---|---|---|
| 1864 | E3 | 3-CH₃ | H | H | 1 CH₃ | CH₃CO | 2-Cl | 1 | O | O | CH₃ |
| 1865 | E3 | 3-CH₃ | H | H | 1 CH₃ | CH₃CH₂CO | 2-Cl | 1 | O | O | CH₃ |
| 1866 | E3 | 3-CH₃ | H | H | 1 CH₃ | PhCO | 2-Cl | 1 | O | O | CH₃ |
| 1867 | E3 | 3-CH₃ | H | H | 1 CH₃ | 4-Cl-PhCO | 2-Cl | 1 | O | O | CH₃ |
| 1868 | E3 | 3-CH₃ | H | H | 1 CH₃ | PhCH₂CO | 2-Cl | 1 | O | O | CH₃ |
| 1869 | E3 | 3-CH₃ | H | H | 1 CH₃ | CHO | 2-Cl | 1 | O | O | CH₃ |
| 1870 | E3 | 3-CH₃ | H | H | 1 CH₃ | CH₃OCH₂ | 2-Cl | 1 | O | O | CH₃ |
| 1871 | E3 | 3-CH₃ | H | H | 1 CH₃ | CH₃CH(OCH₃) | 2-Cl | 1 | O | O | CH₃ |
| 1872 | E3 | 3-CH₃ | H | H | 1 CH₃ | CH₃SO₂ | 2-Cl | 1 | O | O | CH₃ |
| 1873 | E3 | 3-CH₃ | H | H | 1 CH₃ | PhSO₂ | 2-Cl | 1 | O | O | CH₃ |
| 1874 | E3 | 3-CH₃ | H | H | 1 CH₃ | 4-CH₃-PhSO₂ | 2-Cl | 1 | O | O | CH₃ |
| 1875 | E3 | 3-CH₃ | H | H | 1 CH₃ | H | 2-Cl | 1 | S | O | CH₃ |
| 1876 | E3 | 3-CH₃ | H | H | 1 CH₃ | H | 2-Cl | 1 | O | S | CH₃ |
| 1877 | E3 | 3-CH₃ | H | H | 1 CH₃ | H | 2-Cl | 1 | O | — | CH₃ |
| 1878 | E3 | 3-CH₃ | H | H | 1 CH₃ | H | 2-Cl | 1 | O | NH | CH₃ |
| 1879 | E3 | 3-CH₃ | H | H | 1 CH₃ | H | 2-Cl | 1 | O | NCH₃ | CH₃ |
| 1880 | E3 | 3-CH₃ | H | H | 1 CH₃ | H | 2-Cl | 1 | O | O | H |
| 1881 | E3 | 3-CH₃ | H | H | 1 CH₃ | H | 2-Cl | 1 | O | O | Et |
| 1882 | E3 | 3-CH₃ | H | H | 1 CH₃ | H | 2-Cl | 1 | O | O | n-Pr |
| 1883 | E3 | 3-CH₃ | H | H | 1 CH₃ | H | 2-Cl | 1 | O | O | CH₂CH=CH₂ |
| 1884 | E3 | 3-CH₃ | H | H | 1 CH₃ | H | 2-Cl | 1 | O | O | CH=CH₂ |
| 1885 | E3 | 3-CH₃ | H | H | 1 CH₃ | H | 2-Cl | 1 | O | O | Propargyl |
| 1886 | E3 | 3-CH₃ | H | H | 1 CH₃ | H | 2-Cl | 1 | O | O | ethynyl |
| 1887 | E3 | 3-CH₃ | H | H | 1 CH₃ | H | 2-Cl | 1 | O | O | CF₃ |
| 1888 | E3 | 3-CH₃ | H | H | 1 CH₃ | H | 2-Cl | 1 | O | O | CH₂CF₃ |
| 1889 | E3 | 3-CH₃ | H | H | 1 CH₃ | H | 2-Cl | 1 | O | O | CF₂CF₃ |
| 1890 | E3 | 3-CH₃ | H | H | 1 CH₃ | H | 2-Cl | 1 | O | O | CF₂CF₂H |
| 1891 | E3 | 3-CH₃ | H | H | 1 CH₃ | H | 2-Cl | 1 | O | O | CH₂CH=CHCl |
| 1892 | E3 | 3-CH₃ | H | H | 1 CH₃ | H | 2-Cl | 1 | O | O | 3-Iodo-propargyl |
| 1893 | E3 | 3-CH₃ | H | H | 1 CH₃ | H | 2-Cl | 1 | O | O | c-Pr |
| 1894 | E3 | 3-CH₃ | H | H | 1 CH₃ | H | 2-Cl | 1 | O | O | c-Hex |
| 1895 | E3 | 3-CH₃ | H | H | 1 CH₃ | H | 2-Cl | 1 | O | O | 2-CH₃-c-Pr |
| 1896 | E3 | — | H | H | 1 CH₃ | H | 2-CH₃ | 1 | O | O | CH₃ |

TABLE 32

| | | | | | | | | | | | |
|---|---|---|---|---|---|---|---|---|---|---|---|
| 1897 | E3 | 3-CH₃ | H | H | 1 CH₃ | H | 2-CH₃ | 1 | O | O | CH₃ |
| 1898 | E3 | 3-Et | H | H | 1 CH₃ | H | 2-CH₃ | 1 | O | O | CH₃ |
| 1899 | E3 | 3-CF₃ | H | H | 1 CH₃ | H | 2-CH₃ | 1 | O | O | CH₃ |
| 1900 | E3 | 3-F | H | H | 1 CH₃ | H | 2-CH₃ | 1 | O | O | CH₃ |
| 1901 | E3 | 3-Cl | H | H | 1 CH₃ | H | 2-CH₃ | 1 | O | O | CH₃ |
| 1902 | E3 | 3-OCH₃ | H | H | 1 CH₃ | H | 2-CH₃ | 1 | O | O | CH₃ |
| 1903 | E3 | 3-OEt | H | H | 1 CH₃ | H | 2-CH₃ | 1 | O | O | CH₃ |
| 1904 | E3 | 3-OCF₃ | H | H | 1 CH₃ | H | 2-CH₃ | 1 | O | O | CH₃ |
| 1905 | E3 | 6-CH₃ | H | H | 1 CH₃ | H | 2-CH₃ | 1 | O | O | CH₃ |
| 1906 | E3 | 6-Et | H | H | 1 CH₃ | H | 2-CH₃ | 1 | O | O | CH₃ |
| 1907 | E3 | 6-CF₃ | H | H | 1 CH₃ | H | 2-CH₃ | 1 | O | O | CH₃ |
| 1908 | E3 | 6-F | H | H | 1 CH₃ | H | 2-CH₃ | 1 | O | O | CH₃ |
| 1909 | E3 | 6-Cl | H | H | 1 CH₃ | H | 2-CH₃ | 1 | O | O | CH₃ |
| 1910 | E3 | 6-OCH₃ | H | H | 1 CH₃ | H | 2-CH₃ | 1 | O | O | CH₃ |
| 1911 | E3 | 6-OEt | H | H | 1 CH₃ | H | 2-CH₃ | 1 | O | O | CH₃ |
| 1912 | E3 | 6-OCF₃ | H | H | 1 CH₃ | H | 2-CH₃ | 1 | O | O | CH₃ |
| 1913 | E3 | 3,6-diCH₃ | H | H | 1 CH₃ | H | 2-CH₃ | 1 | O | O | CH₃ |
| 1914 | E3 | 3-Et-6-CH₃ | H | H | 1 CH₃ | H | 2-CH₃ | 1 | O | O | CH₃ |
| 1915 | E3 | 3-CF₃-6-F | H | H | 1 CH₃ | H | 2-CH₃ | 1 | O | O | CH₃ |
| 1916 | E3 | 3,6-diF | H | H | 1 CH₃ | H | 2-CH₃ | 1 | O | O | CH₃ |
| 1917 | E3 | 3-Cl-6-F | H | H | 1 CH₃ | H | 2-CH₃ | 1 | O | O | CH₃ |
| 1918 | E3 | 3,6-diOCH₃ | H | H | 1 CH₃ | H | 2-CH₃ | 1 | O | O | CH₃ |
| 1919 | E3 | 3-OEt-6-CH₃ | H | H | 1 CH₃ | H | 2-CH₃ | 1 | O | O | CH₃ |
| 1920 | E3 | 3-OCF₃-6-F | H | H | 1 CH₃ | H | 2-CH₃ | 1 | O | O | CH₃ |
| 1921 | E3 | 3-CH₃ | H | CH₃ | 1 CH₃ | H | 2-CH₃ | 1 | O | O | CH₃ |
| 1922 | E3 | 3-Et | H | CH₃ | 1 CH₃ | H | 2-CH₃ | 1 | O | O | CH₃ |
| 1923 | E3 | 6-Et | H | CH₃ | 1 CH₃ | H | 2-CH₃ | 1 | O | O | CH₃ |
| 1924 | E3 | 3-CH₃ | H | Et | 1 CH₃ | H | 2-CH₃ | 1 | O | O | CH₃ |
| 1925 | E3 | 3-CH₃ | H | i-Pr | 1 CH₃ | H | 2-CH₃ | 1 | O | O | CH₃ |
| 1926 | E3 | 3-CH₃ | CH₃ | Et | 1 CH₃ | H | 2-CH₃ | 1 | O | O | CH₃ |
| 1927 | E3 | 3-CH₃ | H | F | 1 CH₃ | H | 2-CH₃ | 1 | O | O | CH₃ |
| 1928 | E3 | 3-CH₃ | F | F | 1 CH₃ | H | 2-CH₃ | 1 | O | O | CH₃ |
| 1929 | E3 | 3-CH₃ | H | CF₃ | 1 CH₃ | H | 2-CH₃ | 1 | O | O | CH₃ |

TABLE 32-continued

| | | | | | | | | | | |
|---|---|---|---|---|---|---|---|---|---|---|
| 1930 | E3 | 3-CH$_3$ | H | c-Pr | 1 CH$_3$ | H | 2-CH$_3$ | 1 O | O | CH$_3$ |
| 1931 | E3 | 3-CH$_3$ | | —CH2CH2— | 1 CH$_3$ | H | 2-CH$_3$ | 1 O | O | CH$_3$ |
| 1932 | E3 | 3-CH$_3$ | | —CH2CH2CH2— | 1 CH$_3$ | H | 2-CH$_3$ | 1 O | O | CH$_3$ |
| 1933 | E3 | 3-CH$_3$ | | —CH2CH(CH3)— | 1 CH$_3$ | H | 2-CH$_3$ | 1 O | O | CH$_3$ |
| 1934 | E3 | 3-CH$_3$ | | —CH2C(CH3)2— | 1 CH$_3$ | H | 2-CH$_3$ | 1 O | O | CH$_3$ |
| 1935 | E3 | 3-CH$_3$ | H | H | 1 H | H | 2-CH$_3$ | 1 O | O | CH$_3$ |
| 1936 | E3 | 3-CH$_3$ | H | H | 1 Et | H | 2-CH$_3$ | 1 O | O | CH$_3$ |
| 1937 | E3 | 3-CH$_3$ | H | H | 1 c-Pr | H | 2-CH$_3$ | 1 O | O | CH$_3$ |
| 1938 | E3 | 3-CH$_3$ | H | H | 1 CH=CH$_2$ | H | 2-CH$_3$ | 1 O | O | CH$_3$ |
| 1939 | E3 | 3-CH$_3$ | H | H | 1 CH$_2$CH=CH$_2$ | H | 2-CH$_3$ | 1 O | O | CH$_3$ |
| 1940 | E3 | 3-CH$_3$ | H | H | 1 ethynyl | H | 2-CH$_3$ | 1 O | O | CH$_3$ |
| 1941 | E3 | 3-CH$_3$ | H | H | 1 Propargyl | H | 2-CH$_3$ | 1 O | O | CH$_3$ |
| 1942 | E3 | 3-CH$_3$ | H | H | 1 CF$_3$ | H | 2-CH$_3$ | 1 O | O | CH$_3$ |
| 1943 | E3 | 3-CH$_3$ | H | H | 1 CH=CHCl | H | 2-CH$_3$ | 1 O | O | CH$_3$ |
| 1944 | E3 | 3-CH$_3$ | H | H | 1 3,3,2-tri-Iodo-allyl | H | 2-CH$_3$ | 1 O | O | CH$_3$ |
| 1945 | E3 | 3-CH$_3$ | H | H | 1 3-Iodopropargyl | H | 2-CH$_3$ | 1 O | O | CH$_3$ |
| 1946 | E3 | 3-CH$_3$ | H | H | 1 CN | H | 2-CH$_3$ | 1 O | O | CH$_3$ |
| 1947 | E3 | 3-CH$_3$ | H | H | 1 CN | H | 2-CH$_3$ | 1 O | O | CH$_3$ |
| 1948 | E3 | 3-CH$_3$ | H | H | 1 NO$_2$ | H | 2-CH$_3$ | 1 O | O | CH$_3$ |
| 1949 | E3 | 3-CH$_3$ | H | H | 1 NH$_2$ | H | 2-CH$_3$ | 1 O | O | CH$_3$ |
| 1950 | E3 | 3-CH$_3$ | H | H | 1 NHCH$_3$ | H | 2-CH$_3$ | 1 O | O | CH$_3$ |
| 1951 | E3 | 3-CH$_3$ | H | H | 1 N(CH$_3$)$_2$ | H | 2-CH$_3$ | 1 O | O | CH$_3$ |
| 1952 | E3 | 3-CH$_3$ | H | H | 1 CH$_3$ | CH$_3$ | 2-CH$_3$ | 1 O | O | CH$_3$ |
| 1953 | E3 | 3-CH$_3$ | H | H | 1 CH$_3$ | Et | 2-CH$_3$ | 1 O | O | CH$_3$ |
| 1954 | E3 | 3-CH$_3$ | H | H | 1 CH$_3$ | CH$_3$CO | 2-CH$_3$ | 1 O | O | CH$_3$ |
| 1955 | E3 | 3-CH$_3$ | H | H | 1 CH$_3$ | CH$_3$CH$_2$CO | 2-CH$_3$ | 1 O | O | CH$_3$ |
| 1956 | E3 | 3-CH$_3$ | H | H | 1 CH$_3$ | PhCO | 2-CH$_3$ | 1 O | O | CH$_3$ |
| 1957 | E3 | 3-CH$_3$ | H | H | 1 CH$_3$ | 4-Cl-PhCO | 2-CH$_3$ | 1 O | O | CH$_3$ |
| 1958 | E3 | 3-CH$_3$ | H | H | 1 CH$_3$ | PhCH$_2$CO | 2-CH$_3$ | 1 O | O | CH$_3$ |

TABLE 33

| | | | | | | | | | | |
|---|---|---|---|---|---|---|---|---|---|---|
| 1959 | E3 | 3-CH$_3$ | H | H | 1 CH$_3$ | CHO | 2-CH$_3$ | 1 O | O | CH$_3$ |
| 1960 | E3 | 3-CH$_3$ | H | H | 1 CH$_3$ | CH$_3$OCH$_2$ | 2-CH$_3$ | 1 O | O | CH$_3$ |
| 1961 | E3 | 3-CH$_3$ | H | H | 1 CH$_3$ | CH$_3$CH(OCH$_3$) | 2-CH$_3$ | 1 O | O | CH$_3$ |
| 1962 | E3 | 3-CH$_3$ | H | H | 1 CH$_3$ | CH$_3$SO$_2$ | 2-CH$_3$ | 1 O | O | CH$_3$ |
| 1963 | E3 | 3-CH$_3$ | H | H | 1 CH$_3$ | PhSO$_2$ | 2-CH$_3$ | 1 O | O | CH$_3$ |
| 1964 | E3 | 3-CH$_3$ | H | H | 1 CH$_3$ | 4-CH$_3$-PhSO$_2$ | 2-CH$_3$ | 1 O | O | CH$_3$ |
| 1965 | E3 | 3-CH$_3$ | H | H | 1 CH$_3$ | H | 2-CH$_3$ | 1 S | O | CH$_3$ |
| 1966 | E3 | 3-CH$_3$ | H | H | 1 CH$_3$ | H | 2-CH$_3$ | 1 O | S | CH$_3$ |
| 1967 | E3 | 3-CH$_3$ | H | H | 1 CH$_3$ | H | 2-CH$_3$ | 1 O | — | CH$_3$ |
| 1968 | E3 | 3-CH$_3$ | H | H | 1 CH$_3$ | H | 2-CH$_3$ | 1 O | NH | CH$_3$ |
| 1969 | E3 | 3-CH$_3$ | H | H | 1 CH$_3$ | H | 2-CH$_3$ | 1 O | NCH$_3$ | CH$_3$ |
| 1970 | E3 | 3-CH$_3$ | H | H | 1 CH$_3$ | H | 2-CH$_3$ | 1 O | O | H |
| 1971 | E3 | 3-CH$_3$ | H | H | 1 CH$_3$ | H | 2-CH$_3$ | 1 O | O | Et |
| 1972 | E3 | 3-CH$_3$ | H | H | 1 CH$_3$ | H | 2-CH$_3$ | 1 O | O | n-Pr |
| 1973 | E3 | 3-CH$_3$ | H | H | 1 CH$_3$ | H | 2-CH$_3$ | 1 O | O | CH$_2$CH=CH$_2$ |
| 1974 | E3 | 3-CH$_3$ | H | H | 1 CH$_3$ | H | 2-CH$_3$ | 1 O | O | CH=CH$_2$ |
| 1975 | E3 | 3-CH$_3$ | H | H | 1 CH$_3$ | H | 2-CH$_3$ | 1 O | O | Propargyl |
| 1976 | E3 | 3-CH$_3$ | H | H | 1 CH$_3$ | H | 2-CH$_3$ | 1 O | O | ethynyl |
| 1977 | E3 | 3-CH$_3$ | H | H | 1 CH$_3$ | H | 2-CH$_3$ | 1 O | O | CF$_3$ |
| 1978 | E3 | 3-CH$_3$ | H | H | 1 CH$_3$ | H | 2-CH$_3$ | 1 O | O | CH$_2$CF$_3$ |
| 1979 | E3 | 3-CH$_3$ | H | H | 1 CH$_3$ | H | 2-CH$_3$ | 1 O | O | CF$_2$CF$_3$ |
| 1980 | E3 | 3-CH$_3$ | H | H | 1 CH$_3$ | H | 2-CH$_3$ | 1 O | O | CF$_2$CF$_2$H |
| 1981 | E3 | 3-CH$_3$ | H | H | 1 CH$_3$ | H | 2-CH$_3$ | 1 O | O | CH$_2$CH=CHCl |
| 1982 | E3 | 3-CH$_3$ | H | H | 1 CH$_3$ | H | 2-CH$_3$ | 1 O | O | 3-Iodo-propargyl |
| 1983 | E3 | 3-CH$_3$ | H | H | 1 CH$_3$ | H | 2-CH$_3$ | 1 O | O | c-Pr |
| 1984 | E3 | 3-CH$_3$ | H | H | 1 CH$_3$ | H | 2-CH$_3$ | 1 O | O | c-Hex |
| 1985 | E3 | 3-CH$_3$ | H | H | 1 CH$_3$ | H | 2-CH$_3$ | 1 O | O | 2-CH$_3$-c-Pr |
| 1986 | A1 | — | H | H | 2 CH$_3$ | H | 2-Cl | 1 O | O | CH$_3$ |
| 1987 | A1 | — | H | H | 2 CH$_3$ | H | 2-CH$_3$ | 1 O | O | CH$_3$ |

In addition, specific examples of the ketone derivative represented by the aforementioned formula (II), which is an important key intermediate in the production of the oxime ether derivative of the present invention, are shown in the second tables (Tables 34 to 38).

(Second Tables)

TABLE 34

(II-1)

$R^4-C(=O)-C_6H_3(X)_n-O-N(R^5)-C(=Y)-Z-R^3$

| No | $R^4$ | X | n | $R^5$ | Y | Z | $R^3$ |
|---|---|---|---|---|---|---|---|
| II-1 | $CH_3$ | — | 0 | H | O | O | $CH_3$ |
| II-2 | H | 2-Cl | 1 | H | O | O | $CH_3$ |
| II-3 | Et | 2-Cl | 1 | H | O | O | $CH_3$ |
| II-4 | $CH_3$ | 2-Cl | 1 | H | O | O | $CH_3$ |
| II-5 | $CH=CH_2$ | 2-Cl | 1 | H | O | O | $CH_3$ |
| II-6 | $CH_2CH=CH_2$ | 2-Cl | 1 | H | O | O | $CH_3$ |
| II-7 | ethynyl | 2-Cl | 1 | H | O | O | $CH_3$ |
| II-8 | Propargyl | 2-Cl | 1 | H | O | O | $CH_3$ |
| II-9 | $CF_3$ | 2-Cl | 1 | H | O | O | $CH_3$ |
| II-10 | $CH=CHCl$ | 2-Cl | 1 | H | O | O | $CH_3$ |
| II-11 | 3,3,2-tri-Iodo-allyl | 2-Cl | 1 | H | O | O | $CH_3$ |
| II-12 | 3-Iodopropargyl | 2-Cl | 1 | H | O | O | $CH_3$ |
| II-13 | CN | 2-Cl | 1 | H | O | O | $CH_3$ |
| II-14 | $NO_2$ | 2-Cl | 1 | H | O | O | $CH_3$ |
| II-15 | $NH_2$ | 2-Cl | 1 | H | O | O | $CH_3$ |
| II-16 | $NHCH_3$ | 2-Cl | 1 | H | O | O | $CH_3$ |
| II-17 | $N(CH_3)_2$ | 2-Cl | 1 | H | O | O | $CH_3$ |
| II-18 | $CH_3$ | 2-Cl | 1 | $CH_3$ | O | O | $CH_3$ |
| II-19 | $CH_3$ | 2-Cl | 1 | Et | O | O | $CH_3$ |
| II-20 | $CH_3$ | 2-Cl | 1 | $CH_3CO$ | O | O | $CH_3$ |
| II-21 | $CH_3$ | 2-Cl | 1 | $CH_3CH_2CO$ | O | O | $CH_3$ |
| II-22 | $CH_3$ | 2-Cl | 1 | PhCO | O | O | $CH_3$ |

TABLE 35

| No | $R^4$ | X | n | $R^5$ | Y | Z | $R^3$ |
|---|---|---|---|---|---|---|---|
| II-23 | $CH_3$ | 2-Cl | 1 | 4-Cl-PhCO | O | O | $CH_3$ |
| II-24 | $CH_3$ | 2-Cl | 1 | $PhCH_2CO$ | O | O | $CH_3$ |
| II-25 | $CH_3$ | 2-Cl | 1 | CHO | O | O | $CH_3$ |
| II-26 | $CH_3$ | 2-Cl | 1 | $CH_3OCH_2$ | O | O | $CH_3$ |
| II-27 | $CH_3$ | 2-Cl | 1 | $CH_3CH(OCH_3)$ | O | O | $CH_3$ |
| II-28 | $CH_3$ | 2-Cl | 1 | $CH_3SO_2$ | O | O | $CH_3$ |
| II-29 | $CH_3$ | 2-Cl | 1 | $PhSO_2$ | O | O | $CH_3$ |
| II-30 | $CH_3$ | 2-Cl | 1 | 4-$CH_3$-$PhSO_2$ | O | O | $CH_3$ |
| II-31 | $CH_3$ | 2-Cl | 1 | H | S | O | $CH_3$ |
| II-32 | $CH_3$ | 2-Cl | 1 | H | O | — | $CH_3$ |
| II-33 | $CH_3$ | 2-Cl | 1 | H | O | S | $CH_3$ |
| II-34 | $CH_3$ | 2-Cl | 1 | H | O | NH | $CH_3$ |
| II-35 | $CH_3$ | 2-Cl | 1 | H | O | $NCH_3$ | $CH_3$ |
| II-36 | $CH_3$ | 2-Cl | 1 | H | O | O | H |
| II-37 | $CH_3$ | 2-Cl | 1 | H | O | O | Et |
| II-38 | $CH_3$ | 2-Cl | 1 | H | O | O | n-Pr |
| II-39 | $CH_3$ | 2-Cl | 1 | H | O | O | $CH_2CH=CH_2$ |
| II-40 | $CH_3$ | 2-Cl | 1 | H | O | O | $CH=CH_2$ |
| II-41 | $CH_3$ | 2-Cl | 1 | H | O | O | Propargyl |
| II-42 | $CH_3$ | 2-Cl | 1 | H | O | O | ethynyl |
| II-43 | $CH_3$ | 2-Cl | 1 | H | O | O | $CF_3$ |
| II-44 | $CH_3$ | 2-Cl | 1 | H | O | O | $CH_2CF_3$ |
| II-45 | $CH_3$ | 2-Cl | 1 | H | O | O | $CF_2CF_3$ |
| II-46 | $CH_3$ | 2-Cl | 1 | H | O | O | $CF_2CF_2H$ |
| II-47 | $CH_3$ | 2-Cl | 1 | H | O | O | $CH_2CH=CHCl$ |
| II-48 | $CH_3$ | 2-Cl | 1 | H | O | O | 3-Iodo-propargyl |
| II-49 | $CH_3$ | 2-Cl | 1 | H | O | O | c-Pr |
| II-50 | $CH_3$ | 2-Cl | 1 | H | O | O | c-Hex |
| II-51 | $CH_3$ | 2-Cl | 1 | H | O | O | 2-$CH_3$-c-Pr |

TABLE 36

| No | $R^4$ | X | n | $R^5$ | Y | Z | $R^3$ |
|---|---|---|---|---|---|---|---|
| II-52 | H | 2-$CH_3$ | 1 | H | O | O | $CH_3$ |
| II-53 | Et | 2-$CH_3$ | 1 | H | O | O | $CH_3$ |
| II-54 | $CH_3$ | 2-$CH_3$ | 1 | H | O | O | $CH_3$ |
| II-55 | $CH=CH_2$ | 2-$CH_3$ | 1 | H | O | O | $CH_3$ |
| II-56 | $CH_2CH=CH_2$ | 2-$CH_3$ | 1 | H | O | O | $CH_3$ |
| II-57 | ethynyl | 2-$CH_3$ | 1 | H | O | O | $CH_3$ |
| II-58 | Propargyl | 2-$CH_3$ | 1 | H | O | O | $CH_3$ |
| II-59 | $CF_3$ | 2-$CH_3$ | 1 | H | O | O | $CH_3$ |
| II-60 | $CH=CHCl$ | 2-$CH_3$ | 1 | H | O | O | $CH_3$ |
| II-61 | 3,3,2-tri-Iodo-allyl | 2-$CH_3$ | 1 | H | O | O | $CH_3$ |
| II-62 | 3-Iodopropargyl | 2-$CH_3$ | 1 | H | O | O | $CH_3$ |
| II-63 | CN | 2-$CH_3$ | 1 | H | O | O | $CH_3$ |
| II-64 | $NO_2$ | 2-$CH_3$ | 1 | H | O | O | $CH_3$ |
| II-65 | $NH_2$ | 2-$CH_3$ | 1 | H | O | O | $CH_3$ |
| II-66 | $NHCH_3$ | 2-$CH_3$ | 1 | H | O | O | $CH_3$ |
| II-67 | $N(CH_3)_2$ | 2-$CH_3$ | 1 | H | O | O | $CH_3$ |
| II-68 | $CH_3$ | 2-$CH_3$ | 1 | $CH_3$ | O | O | $CH_3$ |
| II-69 | $CH_3$ | 2-$CH_3$ | 1 | Et | O | O | $CH_3$ |
| II-70 | $CH_3$ | 2-$CH_3$ | 1 | $CH_3CO$ | O | O | $CH_3$ |
| II-71 | $CH_3$ | 2-$CH_3$ | 1 | $CH_3CH_2CO$ | O | O | $CH_3$ |
| II-72 | $CH_3$ | 2-$CH_3$ | 1 | PhCO | O | O | $CH_3$ |
| II-73 | $CH_3$ | 2-$CH_3$ | 1 | 4-Cl-PhCO | O | O | $CH_3$ |
| II-74 | $CH_3$ | 2-$CH_3$ | 1 | $PhCH_2CO$ | O | O | $CH_3$ |
| II-75 | $CH_3$ | 2-$CH_3$ | 1 | CHO | O | O | $CH_3$ |
| II-76 | $CH_3$ | 2-$CH_3$ | 1 | $CH_3OCH_2$ | O | O | $CH_3$ |
| II-77 | $CH_3$ | 2-$CH_3$ | 1 | $CH_3CH(OCH_3)$ | O | O | $CH_3$ |
| II-78 | $CH_3$ | 2-$CH_3$ | 1 | $CH_3SO_2$ | O | O | $CH_3$ |
| II-79 | $CH_3$ | 2-$CH_3$ | 1 | $PhSO_2$ | O | O | $CH_3$ |
| II-80 | $CH_3$ | 2-$CH_3$ | 1 | 4-$CH_3$-$PhSO_2$ | O | O | $CH_3$ |

TABLE 37

| No | $R^4$ | X | n | $R^5$ | Y | Z | $R^3$ |
|---|---|---|---|---|---|---|---|
| II-81 | $CH_3$ | 2-$CH_3$ | 1 | H | S | O | $CH_3$ |
| II-82 | $CH_3$ | 2-$CH_3$ | 1 | H | O | — | $CH_3$ |
| II-83 | $CH_3$ | 2-$CH_3$ | 1 | H | O | S | $CH_3$ |
| II-84 | $CH_3$ | 2-$CH_3$ | 1 | H | O | NH | $CH_3$ |
| II-85 | $CH_3$ | 2-$CH_3$ | 1 | H | O | $NCH_3$ | $CH_3$ |
| II-86 | $CH_3$ | 2-$CH_3$ | 1 | H | O | O | H |
| II-87 | $CH_3$ | 2-$CH_3$ | 1 | H | O | O | Et |
| II-88 | $CH_3$ | 2-$CH_3$ | 1 | H | O | O | n-Pr |
| II-89 | $CH_3$ | 2-$CH_3$ | 1 | H | O | O | $CH_2CH=CH_2$ |
| II-90 | $CH_3$ | 2-$CH_3$ | 1 | H | O | O | $CH=CH_2$ |
| II-91 | $CH_3$ | 2-$CH_3$ | 1 | H | O | O | Propargyl |
| II-92 | $CH_3$ | 2-$CH_3$ | 1 | H | O | O | ethynyl |
| II-93 | $CH_3$ | 2-$CH_3$ | 1 | H | O | O | $CF_3$ |
| II-94 | $CH_3$ | 2-$CH_3$ | 1 | H | O | O | $CH_2CF_3$ |
| II-95 | $CH_3$ | 2-$CH_3$ | 1 | H | O | O | $CF_2CF_3$ |
| II-96 | $CH_3$ | 2-$CH_3$ | 1 | H | O | O | $CF_2CF_2H$ |
| II-97 | $CH_3$ | 2-$CH_3$ | 1 | H | O | O | $CH_2CH=CHCl$ |
| II-98 | $CH_3$ | 2-$CH_3$ | 1 | H | O | O | 3-Iodo-propargyl |
| II-99 | $CH_3$ | 2-$CH_3$ | 1 | H | O | O | c-Pr |
| II-100 | $CH_3$ | 2-$CH_3$ | 1 | H | O | O | c-Hex |
| II-101 | $CH_3$ | 2-$CH_3$ | 1 | H | O | O | 2-$CH_3$-c-Pr |
| II-102 | H | 2-Cl | 1 | H | O | O | t-Bu |
| II-103 | $CH_3$ | 2-Cl | 1 | H | O | O | t-Bu |
| II-104 | $CF_3$ | 2-Cl | 1 | H | O | O | t-Bu |
| II-105 | $CHF_2$ | 2-Cl | 1 | H | O | O | $CH_3$ |
| II-106 | $CHF_2$ | 2-Cl | 1 | H | O | O | t-Bu |
| II-107 | $CH_3$ | 2-F | 1 | H | O | O | $CH_3$ |
| II-108 | $CH_3$ | 2-F | 1 | H | O | O | t-Bu |
| II-109 | $CH_3$ | 2-Br | 1 | H | O | O | t-Bu |

TABLE 38

| No | $R^4$ | X | n | $R^5$ | Y | Z | $R^3$ |
|---|---|---|---|---|---|---|---|
| II-110 | $CH_3$ | 2-$CHF_2$ | 1 | H | O | O | $CH_3$ |
| II-111 | $CH_3$ | 2-$CHF_2$ | 1 | H | O | O | t-Bu |
| II-112 | $CH_3$ | 2-Cl-3-F | 2 | H | O | O | $CH_3$ |
| II-113 | $CH_3$ | 2-Cl-3-F | 2 | H | O | O | t-Bu |

A compound of the present invention (oxime ether derivative represented by formula (I), or salt thereof) demonstrates superior bactericidal action against a wide range of types of fungi, such as fungi belonging to Oomycetes, Ascomycetes Deuteromycetes and Basidiomycetes. Thus, as will be described later, oxime ether derivative compounds of the present invention are useful as active ingredients of fungicides for agricultural and horticultural use.

2) Fungicide for Agricultural and Horticultural Use

A second aspect of the present invention is a fungicide for agricultural and horticultural use containing at least one of an oxime ether derivative of the present invention represented by formula (I), or a salt thereof (to be referred to as the "fungicide of the present invention").

The fungicide of the present invention contains an oxime ether derivative of the present invention or salt thereof as an active ingredient thereof, and has superior bactericidal action against a wide range of types of fungi, such as fungi belonging to Oomycetes, Ascomycetes Deuteromycetes and Basidiomycetes.

The fungicide of the present invention can be used to control various plant diseases occurring during cultivation of agricultural and horticultural crops such as flowering plants, lawn grasses and pasture grasses by seed treatment, foliar spraying, soil application or water surface application and the like.

Examples of crops in which plant diseases can be controlled along with their plant diseases and causative organisms include:

Sugar Beets:
Cercospora leaf spot (*Cercospora beticola*)
Peanuts:
Brown leaf spot (*Mycosphaerella arachidis*)
Black leaf blight (*Mycosphaerella berkeleyi*)
Cucumbers:
Powdery mildew (*Sphaerotheca fuliginea*)
Gummy stem blight (*Mycosphaerella melonis*)
Sclerotinia rot (*Sclerotinia sclerotiorum*)
Gray mold (*Botrytis cinerea*)
Scab (*Cladosporium cucumerinum*)
Corynespora leaf spot (*Corynespora cassicola*)
Damping-off (*Pythium debaryanum, Rhizoctonia solani* Kuhn)
Bacterial spot (*Pseudomonas syringae* pv. *Lecrymans*)
Tomatoes:
Gray mold (*Botrytis cinerea*)
Leaf mold (*Cladosporium fulvum*)
Eggplants:
Gray mold (*Botrytis cinerea*)
Black rot (*Corynespora malongenae*)
Powdery mildew (*Erysiphe cichoracearum*)
Leaf mold (*Mycovellosiella nattrassii*)
Strawberries:
Gray mold (*Botrytis cinerea*)
Powdery mildew (*Sphaerotheca humuli*)
Anthracnose (*Colletotrichum acutatum, Colletotrichum fragariae*)
Onions:
Neck rot (*Botrytis allii*)
Gray mold (*Botrytis cinerea*)
Leaf blight (*Botrytis squamosa*)
Cabbage:
Clubroot (*Plasmodiophora brassicae*)
Bacterial soft rot (*Erwinia carotovora*)
Kidney beans:
Stem rot (*Sclerotinia sclerotiorum*)
Gray mold (*Botrytis cinerea*)
Apples:
Powdery mildew (*Podosphaera leucotricha*)
Scab (*Venturia inaequalis*)
Blossom blight (*Monilinia mali*)
Valsa canker (*Valsa mali*)
Alternaria blotch (*Alternaria mali*)
Rust (*Gymnosporangium yamadae*)
Ring rot (*Botryosphaeria berengeriana*)
Anthracnose (*Coletotrichum gloeosprioides*)
Blotch (*Diplocarpon mali*)
Persimmons:
Powdery mildew (*Phyllactinia kakicola*)
Anthracnose (*Gloeosporium kaki*)
Angular leaf spot (*Cercospora kaki*)
Peaches and cherries:
Brown rot (*Monilinia fructicola*)
Grapes:
Gray mold (*Botrytis cinerea*)
Powdery mildew (*Uncinula necator*)
Ripe rot (*Glomerella cingulata*)
Pears:
Scab (*Venturia nashicola*)
Rust (*Gymnosporangium asiaticum*)
Black spot (*Alternaria kikuchiana*)
Tea:
Gray blight (*Pestalotia theae*)
Anthracnose (*Collectotrichum theae-sinensis*)
Citrus:
Scab (*Elsinoe fawcette*)
Blue mold (*Penicillium italicum*)
Common green mold (*Penicillium digitatum*)
Gray mold (*Botrytis cinerea*)
Melanose (*Diaporthe citri*)
Canker (*Xanthomonas campestris* pv. *Citri*)
Wheat:
Powdery mildew (*Erysiphe graminis* f. sp. *tritici*)
Fusarium blight (*Gibberella zeae*)
Leaf rust (*Puccinia recondita*)
Browning root rot (*Pythium iwayamai*)
Snow mold (*Monographella nivalis*)
Eye spot (*Pseudocercosporella herpotrichoides*)
Speckled leaf blotch (*Septoria tritici*)
Glume blotch (*Leptosphaeria nodorum*)
Typhula snow blight (*Typhula incarnata*)
Sclerotinia snow blight (*Myriosclerotinia borealis*)
Take-all (*Gaeumanomyces graminis*)
Barley:
Stripe (*Pyrenophora graminea*)
Leaf blotch (*Rhynchosporium secalis*)
Loose smut (*Ustilago tritici, U. nuda*)
Rice:
Blast (*Pyricularia oryzae*)
Sheath blight (*Rhizoctonia solani*)
Bakanae disease (*Gibberella fujikuroi*)
Brown spot (*Cochliobolus niyabeanus*)
Tobacco:
Sclerotinia stem-rot (*Sclerotinia sclerotiorum*)
Powdery mildew (*Erysiphe cichoracearum*)
Tulips:
Gray mold (*Botrytis cinerea*)
Bent grass:
Sclerotinia snow blight (*Sclerotinia borealis*)
Orchard grass:
Powdery mildew (*Erysiphe graminis*)
Soybeans:
Purple stain (*Cercospora kikuchii*)
Potatoes, tomatoes:

Late blight (*Phytophthora infestans*)
Cucumbers:
Downy mildew (*Pseudoperonospora cubensis*)
Grapes:
Downy mildew (*Plasmopara viticola*)

In addition, various pathogens have recently developed resistance to benzimidazole fungicides and dicarboximide fungicides resulting in inadequate efficacy of these drugs, thereby creating the need for effective drugs against resistant organisms as well. The fungicide of the present invention also has superior bactericidal effects against resistant organisms in addition to pathogens that are sensitive to these drugs.

For example, the fungicide of the present invention is effective against gray mold (*Botrytis cinerea*), sugar beet *cercospora* leaf spot (*Cercospora beticola*) and apple scab (*Venturia inaequalis*), pear scab (*Venturia nashicola*), which exhibit resistance to benzimidazole fungicides such as thiophanate-methyl, benomyl, carbendazim and thiabendazole, in the same manner as sensitive organisms.

Moreover, the fungicide of the present invention is effective against gray mold (*Botrytis cinerea*), which exhibits resistance to dicarboximide fungicides (such as vinclozoline, procymidone and iprodione) in the same manner as sensitive organisms.

Examples of diseases for which application of the fungicide of the present invention is more preferable include sugar beet *cercospora* leaf spot, wheat powdery mildew, rice blast, apple scab, cucumber gray mold and peanut brown leaf spot.

In addition, the fungicide of the present invention causes little chemical damage, exhibits low toxicity to fish and warm-blooded animals, and has a high degree of safety.

During actual use of the fungicide of the present invention, the oxime ether derivative compound of the present invention may be used in pure form without adding other components, or may be used in the form able to be adopted by an ordinary agricultural chemical for the purpose of using as an agricultural chemical, namely in the form of an agricultural chemical preparation such as a wettable powder, granules, powder, emulsion, aqueous solution, suspension or water-dispersible granules.

Examples of additives and carriers able to be added to the agricultural chemical preparation used for the purpose of solid formulations include vegetable powders such as soybean powder or wheat powder, mineral fine powders such as diatomaceous earth, apatite, gypsum, talc, bentonite, pyrophyllite or clay, and organic and inorganic compounds such as sodium benzoate, urea or sodium sulfate.

In addition, in the case of using for the purpose of liquid formulations, kerosene, xylene and petroleum-based aromatic hydrocarbons, cyclohexane, cyclohexanone, dimethylformamide, dimethylsulfoxide, alcohol, acetone, trichloroethylene, methyl isobutyl ketone, mineral oil, vegetable oil and water, for example, can be used as solvents.

Moreover, a surfactant can be added to these preparations as necessary to obtain a uniform and stable form.

There are no particular limitations on surfactants that can be added, and examples include nonionic surfactants such as polyoxyethylene-alkyl phenyl ethers, polyoxyethylene-alkyl ethers, polyoxyethylene-higher fatty acid esters, polyoxyethylene-sorbitan fatty acid esters or polyoxyethylene-tristyryl phenyl ether, and sulfuric acid ester salts of polyoxyethylene-alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates and isobutylene-maleic anhydrate copolymers.

Wettable powders, emulsions, flowable agents, aqueous solutions and water-dispersible granules are used in the form of solutions, suspensions or emulsions by diluting to a prescribed concentration with water, while powders and granules are used by spraying directly onto plants.

Normally, the amount of active ingredient in the fungicide of the present invention is preferably 0.01 to 90% by weight and more preferably 0.05 to 85% by weight based on the total weight of the composition (preparation).

Although the applied amount of the fungicide of the present invention varies according to weather conditions, preparation form, application time, application method, applied location, target control disease, target crop and the like, it is normally 1 to 1,000 g and preferably 10 to 100 g as the amount of active ingredient compound per hectare.

In the case of applying by diluting a wettable powder, emulsion, suspension, aqueous solutions and water-dispersible granules with water, the applied concentration is 1 to 1000 ppm and preferably 10 to 250 ppm.

In addition to the oxime ether derivative compound of the present invention, the fungicide of the present invention can also be mixed with one or two or more of various fungicides, insecticides, miticides or synergists.

Typical examples of fungicides, insecticides, miticides and plant growth regulators able to be used by mixing with the oxime ether derivative compound of the present invention are indicated below.

Fungicides:
captan, folpet, thiuram, ziram, zineb, maneb, mancozeb, propineb, polycarbamate, chlorothalonil, quintozene, captafol, iprodione, procymidone, vinclozolin, fluoroimide, cymoxanil, mepronil, flutolanil, pencycuron, oxycarboxin, fosetyl-aluminum, propamocarb, triadimefon, triadimenol, propiconazole, diclobutorazol, bitertanol, hexaconazol, miclobutanil, flusilazole, metconazole, etaconazole, fluotrimazole, cyproconazole, epoxyconazole, flutriafen, penconazole, diniconazole, cyproconazole, fenarimol, triflumizole, prochloraz, imazalil, pefurazoate, tridemorph, fenpropimorph, triforine, buthiobate, pyrifenox, anilazine, polyoxin, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentin acetate, triphenyltin hydroxide, diethofencarb, methasulfocarb, qinomethionate, binapacryl, lecithin, sodium bicarbonate, dithianon, dinocap, fenaminosulf, diclomezine, guazatine, dodine, IBP, edifenphos, mepanipyrim, ferimzone, trichlamide, methasulfocarb, fluazinam, ethoqinolac, dimethomorph, pyroquilon, tecloftalam, fthalide, phenazine oxide, thiabendazole, tricyclazole, vinclozolin, cymoxanil, cyclobutanil, guazatine, propamocarb hydrochloride, oxolinic acid, hydroxyisoxazole, iminoctadine acetate, and the like.

Insecticides/Miticides:
Organic phosphorous and carbamate-based insecticides:
fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemetone methyl, ethion, salithion, cyanophos, isoxathion, pyridafenthion, phosalone, methidathion, sulprofos, chlorfenvinphos, tetrachlorovinphos, dimethylvinphos, propaphos, isofenphos, ethyl thiometon, profenofos, pyraclofos, monocrotophos, azinphos-methyl, aldicarb, methomyl, thiodicarb, carbofuran, carbosulphan, benfu-

EXAMPLES

Although the following provides a more detailed explanation of the present invention through examples thereof, the present invention is not limited to the following examples.

Example 1

(1) Production of t-Butyl N-(5-bromo-2-chlorophenoxy) Carbamate

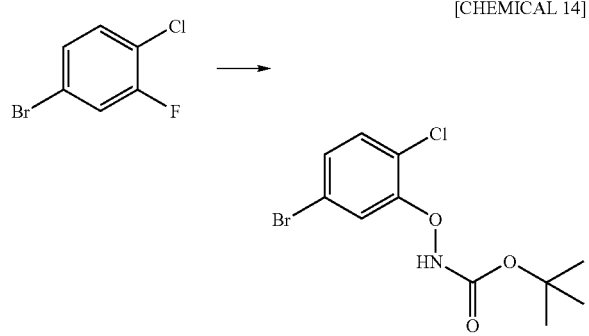

[CHEMICAL 14]

12.34 g of potassium hydroxide were added to a solution in which 5.00 g of 4-bromo-1-chloro-3-fluorobenzene and 4.14 g of N-(t-butoxycarbonyl) hydroxylamine were dissolved in 50 ml of dimethylsulfoxide at room temperature followed by stirring for 2 hours at 60° C. After cooling to room temperature, the reaction solution was poured into ice water and extracted with ethyl acetate. The ethyl acetate layer was washed three times with water followed by drying by addition of anhydrous magnesium sulfate, filtering and distilling off the solvent from the filtrate under reduced pressure. The resulting residue was purified by silica gel column chromatography (developing solvent; n-hexane:ethyl acetate=5:1 (volume ratio)) to obtain 7.39 g of the target compound of t-butyl N-(5-bromo-2-chlorophenoxy) carbamate (yield: 96%).

[$^1$H-NMR Data of t-Butyl N-(5-bromo-2-chlorophenoxy) Carbamate]

$^1$H-NMR (CDCl$_3$/TMS, δ ppm): 7.60 (bs, 1H), 7.47 (d, 1H), 7.20 (d, 1H), 7.10 (dd, 1H), 1.52 (s, 9H)

(2) Production of t-Butyl N-(5-acetyl-2-chlorophenoxy) Carbamate

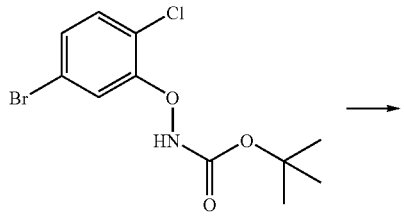

[CHEMICAL 15]

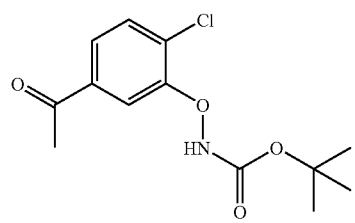

500 ml of THF were cooled to −78° C. in a nitrogen atmosphere followed by the addition of 198 ml of n-butyllithium (2.77 mol/L). A solution containing 67.43 g of t-butyl N-(5-bromo-2-chlorophenoxy) carbamate dissolved in 170 ml of THF was dropped therein followed by stirring for 10 minutes at −78° C. following completion of dropping. Next, 54.63 g of N,N-dimethylacetamide were dropped in followed by stirring for 1 hour at −78° C. following completion of dropping. Following completion of the reaction, an aqueous ammonium chloride solution was added at −78° C. to terminate the reaction followed by extraction with ethyl acetate. After drying the ethyl acetate layer by addition of anhydrous magnesium sulfate and filtering, the solvent was distilled off from the filtrate under reduced pressure. The resulting residue was purified by silica gel column chromatography (developing solvent; n-hexane:ethyl acetate=3:1 (volume ratio)) to obtain 29.18 g of the target compound of t-butyl N-(5-acetyl-2-chlorophenoxy) carbamate in the form of crystals (yield: 49%).

Melting point: 120 to 123° C.

(3) Production of Methyl N-(5-acetyl-2-chlorophenoxy) Carbamate

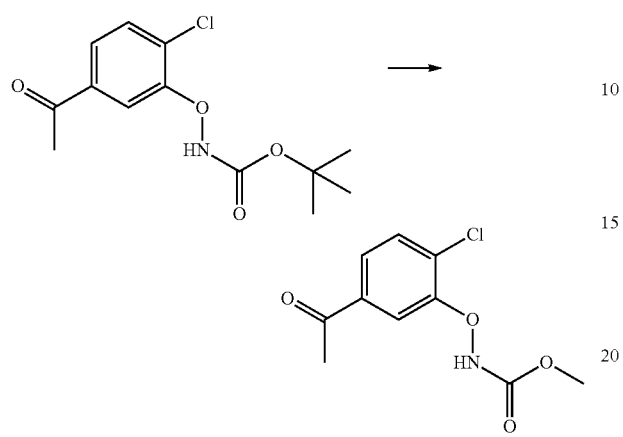

[CHEMICAL 16]

15.37 g of triethylamine were added to a solution containing 28.93 g of t-butyl N-(5-acetyl-2-chlorophenoxy) carbamate dissolved in 380 ml of methylene chloride while cooling with ice. Next, 12.44 g of methyl chloroformate were dropped into this mixture followed by stirring for 1 hour at room temperature following completion of dropping. Following completion of the reaction, water was added to the reaction liquid while cooling with ice to separate the methylene chloride layer. After drying the methylene chloride layer by addition of anhydrous magnesium sulfate and filtering, the solvent was distilled off from the filtrate under reduced pressure.

250 ml of methylene chloride were added to the resulting residue and 64 ml of trifluoroacetic acid were dropped in while cooling with ice followed by stirring for 1.5 hours at room temperature following completion of dropping. Following completion of the reaction, the reaction liquid was transferred to a saturated aqueous sodium bicarbonate solution and extracted with methylene chloride. After drying the methylene chloride layer by addition of anhydrous magnesium sulfate and filtering, the solvent was distilled off from the filtrate under reduced pressure to obtain a crude product. The resulting crude product was then washed with n-hexane to obtain 23.28 g of the target compound of methyl N-(5-acetyl-2-chlorophenoxy) carbamate in the form of crystals (yield: 94%).

Melting point: 154 to 155° C.

(4) Production of (6-Trifluoromethylpyridin-2-yl) Methanol

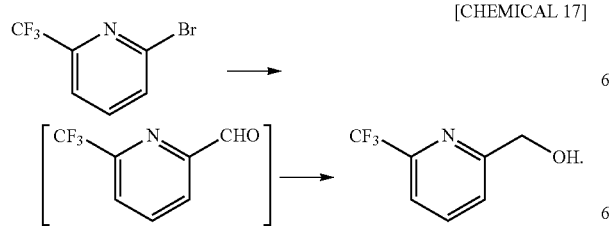

[CHEMICAL 17]

A solution containing 2.00 g of 2-bromo-6-trifluoromethylpyridine dissolved in 50 ml of toluene was cooled to −78° C. followed by dropping in 4.0 ml of n-butyllithium (2.77 mol/L) and stirring for 10 minutes at −78° C. 0.96 g of N,N-dimethylformamide were dropped therein followed by further stirring for 10 minutes at −78° C. following completion of the reaction. 0.67 g of sodium borohydride and 5 ml of methanol were added to the resulting reaction mixture followed by heating to room temperature and stirring for 1 hour at room temperature. Following completion of the reaction, aqueous ammonium chloride solution was added to the reaction liquid followed by extraction with ethyl acetate. The ethyl acetate layer was dried by addition of anhydrous magnesium sulfate followed by filtering and distilling off the solvent from the filtrate under reduced pressure to obtain 1.70 g of a crude product in the form of (6-trifluoromethylpyridin-2-yl) methanol.

[$^1$H-NMR Data of (6-Trifluoromethylpyridin-2-yl) Methanol]

$^1$H-NMR (CDCl$_3$/TMS, δ ppm): 7.88 (dd, 1H), 7.60 (d, 1H), 7.50 (d, 1H), 4.85 (s, 2H), 3.36 (bs, 1H)

(5) Production of t-Butyl N-[(6-trifluoromethylpyridin-2-yl)methoxy] Carbamate

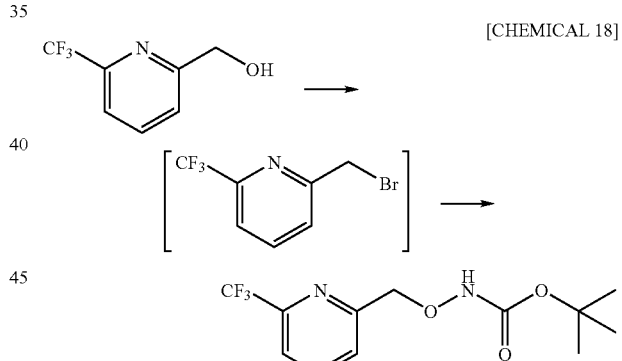

[CHEMICAL 18]

3.78 g of carbon tetrabromide and 2.78 g of triphenylphosphine were added to a solution containing 1.70 g of the (6-trifluoromethylpyridin-2-yl) methanol obtained in (4) dissolved in 30 ml of methylene chloride followed by stirring for 1 hour at room temperature. 30 ml of acetonitrile, 1.52 g of N-(t-butoxycarbonyl) hydroxylamine and 1.74 g of 1,8-diazabicyclo[5.4.0]-7-undecene (DBU) were added to this reaction solution followed by stirring for 3 hours at room temperature. Following completion of the reaction, aqueous ammonium chloride solution was added to the reaction mixture followed by extraction with ethyl acetate. The ethyl acetate layer was dried by addition of anhydrous magnesium sulfate followed by filtration and distilling off the solvent from the filtrate under reduced pressure. The resulting residue was purified by silica gel column chromatography (developing solvent; n-hexane:ethyl acetate=3:1 (volume ratio)) to obtain 1.54 g of the target compound of t-butyl N-[(6-trifluoromethylpyridin-2-yl)methyloxy] carbamate (yield: 59%).

[¹H-NMR Data of t-Butyl N-[(6-trifluoromethylpyridin-2-yl)methyloxy] Carbamate

¹H-NMR (CDCl₃/TMS, δ ppm): 7.90 (dd, 1H), 7.73 (d, 1H), 7.62 (d, 1H), 7.44 (bs, 1H), 1.48 (s, 9H)

(6) Production of Methyl N-(2-chloro-5-{1-[6-fluoromethyl-pyridin-2-ylmethoxyimino]ethyl}phenoxy) Carbamate

[CHEMICAL 19]

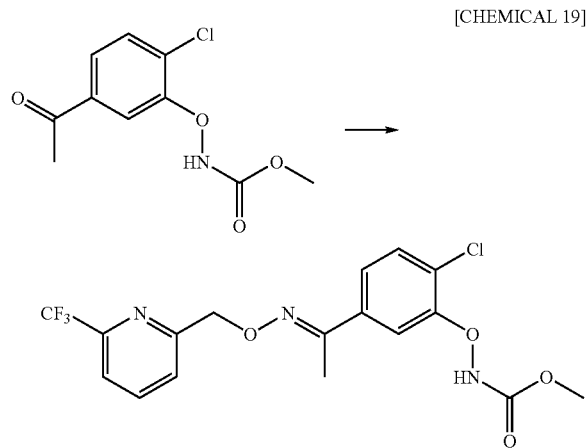

A mixture of 0.30 g of methyl N-(5-acetyl-2-chlorophenoxy) carbamate and 0.47 g of t-butyl N-[(6-trifluoromethylpyridin-2-yl)methyloxy] carbamate was dissolved in 15 ml of dichloroethane. 1 ml of trifluoroacetic acid was added to this solution followed by stirring for 1 hour at 50° C. Following completion of the reaction, ethyl acetate was added to the reaction mixture followed by washing with saturated aqueous sodium bicarbonate solution to separate the organic layer. The resulting organic layer was dried by addition of anhydrous magnesium sulfate followed by filtering and distilling off the solvent from the filtrate under reduced pressure. The resulting residue was purified by silica gel column chromatography (developing solvent; n-hexane:ethyl acetate=3:1 (volume ratio)) to obtain 0.44 g of the target compound of methyl N-(2-chloro-5-{1-[6-trifluoromethylpyridin-2-yl-methoxyimino]ethyl}phenoxy) carbamate in the form of crystals (yield: 86%)

Melting point: 100 to 101° C.

Melting point, refractive index and NMR data for oxime ether derivative compounds of the present invention produced in the same manner as Example 1 are shown in the following third tables (Tables 39 and 40). In the tables, No. indicates the compound number shown in the first table, while NMR indicates values measured in chloroform-d using TMS for the standard.

(Third Tables)

TABLE 39

| No. | Melting Point (° C.) | NMR |
|---|---|---|
| 3 | 100-102 | |
| 4 | | 7.87 (s, 1H), 7.66 (d, 1H), 7.35 (d, 1H), 7.29 (dd, 1H), 6.87 (s, 1H), 5.46 (s, 2H), 3.85 (s, 3H), 2.82 (q, 2H), 2.26 (s, 3H), 1.30 (t, 3H) |
| 5 | 108-109 | |
| 28 | 101-103 | |
| 52 | 141-143 | |
| 93 | | 7.81 (bs, 1H), 7.52 (d, 1H), 7.23 (dd, 1H), 7.12 (d, 1H), 6.86 (s, 1H), 5.46 (s, 2H), 3.82 (s, 3H), 2.64 (q, 2H), 2.27 (s, 3H), 2.26 (s, 3H), 1.28 (t, 3H) |
| 94 | 65-67 | |
| 727 | 108-109 | |
| 1434 | 109-111 | |
| 1434 | 130-132 | |
| 1437 | 98-99 | |
| 1438 | 87-89 | |
| 1444 | 143-145 | |
| 1445 | 120-122 | |
| 1446 | 100-101 | |
| 1448 | 130-131 | |

TABLE 40

| No. | Melting Point (° C.) | Refractive Index | NMR |
|---|---|---|---|
| 1462 | | | 7.75 (s, 1H), 7.55-7.60 (m, 2H), 7.25-7.31 (m, 2H), 7.14 (d, 1H), 7.04 (d, 1H), 5.44 (q, 1H), 3.83 (s, 3H), 2.82 (q, 2H), 2.30 (s, 3H), 1.63 (d, 3H), 1.30 (t, 3H), 1.63 (d, 3H) |
| 1463 | | | 7.76 (s, 1H), 7.63 (dd, 1H), 7.55 (d, 1H), 7.20-7.32 (m, 4H), 5.42 (q, 1H), 3.83 (s, 3H), 2.30 (s, 3H), 1.63 (d, 3H) |
| 1464 | | nD1.5241 (22.9° C.) | |
| 1465 | | nD1.5426 (23° C.) | |
| 1539 | 82-84 | | |
| 1555 | | | 7.99 (bs, 1H), 7.56 (t, 1H), 7.42 (d, 1H), 7.18-7.14 (m, 2H), 7.06 (d, 1H), 7.02 (d, 1H), 5.44 (q, 1H), 3.79 (s, 3H), 2.81 (q, 2H), 2.29 (s, 3H), 2.24 (s, 3H), 1.62 (d, 3H), 1.29 (t, 3H) |
| 1619 | 118-120 | | |
| 1622 | 121-123 | | |

Physical properties or NMR data of ketone derivatives (compounds represented by formula (II)) produced in the same manner as Example 1 are shown in the following fourth table (Table 41).

TABLE 41

| No. | Physical Property (° C.) | NMR |
|---|---|---|
| II-4 | m.p. 154-155 | |
| II-9 | | $^1$H-NMR (CDCl$_3$)/TMS, δ (ppm): 8.01 (d, 1H), 7.95 (s, 1H), 7.69 (dd, 1H), 7.54 (d, 1H), 3.86 (s, 3H) |
| II-54 | | $^1$H-NMR (CDCl$_3$)/TMS, δ (ppm): 7.79 (d, 1H), 7.73 (s, 1H), 7.54 (dd, 1H), 7.21 (d, 1H), 3.84 (s, 3H), 2.57 (s, 3H), 2.32 (s, 3H) |
| II-102 | | $^1$H-NMR (CDCl$_3$)/TMS, δ (ppm): 9.95 (s, 1H), 7.84 (d, 1H), 7.66 (s, 1H), 7.55-7.48 (m, 2H), 1.52 (s, 9H) |
| II-103 | m.p. 120-123 | |
| II-104 | | $^1$H-NMR (CDCl$_3$)/TMS, δ (ppm): 8.00 (d, 1H), 7.74-7.66 (m, 2H), 7.53 (d, 1H), 1.52 (s, 9H) |
| II-105 | | $^1$H-NMR (CDCl$_3$)/TMS, δ (ppm): 8.00 (d, 1H), 7.88 (s, 1H), 7.73 (dd, 1H), 7.52 (d, 1H), 6.25 (t, 1H), 3.86 (s, 3H) |
| II-106 | | $^1$H-NMR (CDCl$_3$)/TMS, δ (ppm): 8.00 (d, 1H), 7.72-7.69 (m, 2H), 7.51 (d, 1H), 6.25 (t, 1H), 1.52 (s, 9H) |
| II-107 | | $^1$H-NMR (CDCl$_3$)/TMS, δ (ppm): 7.95 (dd, 1H), 7.85 (s, 1H), 7.67-7.62 (m, 1H), 7.17 (dd, 1H), 3.86 (s, 3H), 2.58 (s, 3H) |
| II-108 | | $^1$H-NMR (CDCl$_3$)/TMS, δ (ppm): 7.95 (dd, 1H), 7.68 (s, 1H), 7.65-7.60 (m, 1H), 7.16 (dd, 1H), 2.58 (s, 3H), 1.51 (s, 9H) |
| II-109 | | $^1$H-NMR (CDCl$_3$)/TMS, δ (ppm): 7.86 (d, 1H), 7.86 (s, 1H), 7.61 (d, 1H), 7.48 (dd, 1H), 2.59 (s, 3H), 1.52 (s, 9H) |
| II-110 | | $^1$H-NMR (CDCl$_3$)/TMS, δ (ppm): 7.91 (s, 1H), 7.86 (s, 1H), 7.69 (s, 2H), 7.01 (t, 1H), 3.84 (s, 3H), 2.62 (s, 3H) |
| II-111 | | $^1$H-NMR (CDCl$_3$)/TMS, δ (ppm): 7.91 (bs, 2H), 7.68 (bs, 2H), 7.04 (t, 1H), 2.62 (s, 3H), 1.52 (s, 9H) |
| II-112 | | $^1$H-NMR (CDCl$_3$)/TMS, δ (ppm): 7.89 (s, 1H), 7.72 (dd, 1H), 7.44 (dd, 1H), 3.86 (s, 3H), 2.58 (s, 3H) |
| II-113 | | $^1$H-NMR (CDCl$_3$)/TMS, δ (ppm): 7.72 (d, 1H), 7.69 (s, 1H), 7.42 (dd, 1H), 2.58 (s, 3H), 1.52 (s, 9H) |

Although the following indicates some examples of the fungicide of the present invention, the additives and addition ratios are not limited to those indicated in the examples and can be varied over a wide range. In addition, the term "parts" in the preparation examples indicates parts by weight.

Preparation Example 1

Wettable Powder

| | |
|---|---|
| Oxime ether derivative compound of present invention | 40 parts |
| Clay | 48 parts |
| Sodium dioctylsulfosuccinate | 4 parts |
| Sodium lignin sulfonate | 8 parts |

The above components are uniformly mixed and finely crushed to obtain a wettable powder containing 40% of the active ingredient.

Preparation Example 2

Emulsion

| | |
|---|---|
| Oxime ether derivative compound of present invention | 10 parts |
| Solvesso 200 | 53 parts |
| Cylohexanone | 26 parts |
| Calcium dodecylbenzenesulfonate | 1 part |
| Polyoxyethylene alkyl allyl ether | 10 parts |

The above components are mixed and dissolved to obtain an emulsion containing 10% of the active ingredient.

Preparation Example 3

Powder

| | |
|---|---|
| Oxime ether derivative compound of present invention | 10 parts |
| Clay | 90 parts |

The above components are uniformly mixed and finely crushed to obtain a powder containing 10% of the active ingredient.

Preparation Example 4

Granules

| | |
|---|---|
| Oxime ether derivative compound of present invention | 5 parts |
| Clay | 73 parts |
| Bentonite | 20 parts |
| Sodium dioctylsulfosuccinate | 1 part |
| Potassium phosphate | 1 part |

The above components are finely crushed and mixed well followed by the addition of water, mixing well, granulating and drying to obtain granules containing 5% of the active ingredient.

Preparation Example 5

Suspension

| | |
|---|---|
| Oxime ether derivative compound of present invention | 10 parts |
| Polyoxyethylene alkyl allyl ether | 4 parts |
| Sodium polycarbonate | 2 parts |
| Glycerin | 10 parts |
| Xanthan gum | 0.2 parts |
| Water | 73.8 parts |

The above components are mixed followed by wet-crushing to a particle diameter of 3 microns or less to obtain a suspension containing 10% of the active ingredient.

Preparation Example 6

Water Dispersible Granules

| | |
|---|---|
| Oxime ether derivative compound of present invention | 40 parts |
| Clay | 36 parts |
| Potassium chloride | 10 parts |
| Sodium alkylbenzenesulfonate | 1 part |
| Sodium lignin sulfonate | 8 parts |
| Formaldehyde condensation product of sodium alkylbenzenesulfonate | 5 parts |

The above components are uniformly mixed and finely crushed followed by adding a suitable amount of water and mixing to form a clay-like mixture. The clay-like mixture is granulated and dried to obtain water dispersible granules containing 40% of the active ingredient.

The following indicates test examples of fungicides of the present invention obtained in the manner described above.

Test Example 1

Apple Scab Control Test

Emulsions of oxime ether derivative compounds of the present invention were sprayed at an active ingredient concentration of 100 ppm onto apple seedlings (variety: Ralls Janet, leaf stage: 3 to 4) cultivated in unglazed pots. After allowing to air-dry at room temperature, the seedlings were inoculated with conidiospores of apple scab pathogen (*Venturia inaequalis*) followed by holding for 2 weeks indoors at 20° C. and high humidity using a 12 hour light/dark cycle. The appearance of lesions on the leaves was compared with untreated seedlings to determine control effects.

As a result, the following compounds demonstrated superior control values of 75% or more:

compound numbers (compound numbers correspond to compound numbers listed in the above-mentioned first tables, and to apply similarly hereinafter): 3, 4, 5, 28, 52, 93, 94, 727, 1434, 1437, 1438, 1444, 1445, 1446, 1448, 1462, 1463, 1464, 1465, 1539, 1555, 1619, 1622, 1803.

Test Example 2

Wheat Powdery Mildew Control Test

Wettable powders of oxime ether derivative compounds of the present invention were sprayed at a concentration of 100 ppm onto wheat seedlings (variety: Chihoku, leaf stage: 1.0 to 1.2) cultivated in unglazed pots. After allowing the leaves to air-dry, the leaves were shake-inoculated with conidiospores of wheat powdery mildew pathogen (*Erysiphe graminis* f. sp. *tritici*) and held for 7 days in a greenhouse at 22 to 25° C. The appearance of lesions on the leaves was compared with untreated seedlings to determine control effects.

As a result, the following compounds demonstrated superior control values of 75% or more:

compound numbers: 3, 4, 5, 28, 93, 94, 727, 1434, 1437, 1438, 1444, 1445, 1446, 1448, 1462, 1463, 1539, 1555.

Test Example 3

Wheat Leaf Rust Control Test

Wettable powders of oxime ether derivative compounds of the present invention were sprayed at a concentration of 100 ppm onto wheat seedlings (variety: Norin 61, leaf stage: 1.0 to 1.2) cultivated in unglazed pots. After allowing the leaves to air-dry, the leaves were shake-inoculated with urediospores of wheat rust pathogen (*Puccinia recondita*) and held for 10 days in a greenhouse at 22 to 25° C. The appearance of lesions on the leaves was compared with untreated seedlings to determine control effects.

As a result, the following compounds demonstrated superior control values of 75% or more:

compound numbers: 3, 4, 5, 28, 93, 94, 727, 1437, 1438, 1444, 1445, 1446, 1448, 1462, 1463, 1464, 1539, 1555, 1803.

The invention claimed is:

1. An oxime ether derivative represented by the following formula (I), or a salt thereof:

[CHEMICAL 1]

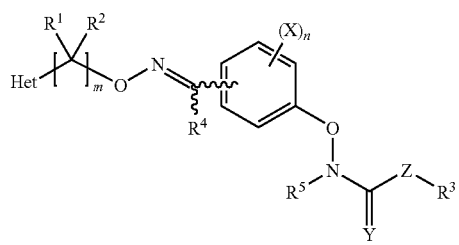

(I)

wherein, X represents a halogen atom, $C_{1-20}$ alkyl group, $C_{1-20}$ alkoxy group, $C_{1-20}$ haloalkyl group or $C_{1-20}$ haloalkoxy group, $R^1$ and $R^2$ each independently represent a hydrogen atom, halogen atom, $C_{1-20}$ alkyl group, $C_{1-20}$ haloalkyl group, optionally substituted $C_{3-10}$ cycloalkyl group, or $R^1$ and $R^2$ may bond together to form a ring, $R^3$ represents a hydrogen atom, $C_{1-20}$ alkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group or optionally substituted $C_{3-10}$ cycloalkyl group;

$R^4$ represents a hydrogen atom, $C_{1-20}$ alkyl group, optionally substituted $C_{3-10}$ cycloalkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group, cyano group, nitro group or optionally substituted amino group, $R^5$ represents a hydrogen atom, $C_{1-20}$ alkyl group, acyl group, formyl group, $C_{1-20}$ alkoxy-$C_{1-20}$ alkyl group, $C_{2-20}$ acyloxy-$C_{1-20}$ alkyl group, $C_{1-20}$ alkoxycarbonyl group, $C_{1-20}$ alkylsulfonyl group or optionally substituted phenylsulfonyl group, Y represents an oxygen atom or sulfur atom, Z represents a single bond, oxygen atom, sulfur atom or $NR^6$ (wherein, $R^6$ represents a hydrogen atom or $C_{1-30}$ alkyl group), Het represents an optionally substituted heterocyclic group, m represents an integer of 1 to 8, and $R^1$ and $R^2$ may be the same or different in the case m is 2 or more, and n represents an integer of 0 to 4, and X may be the same or different in the case n is 2 or more.

2. A fungicide for agricultural and horticultural use that contains at least one of the oxime ether derivative according to claim 1, or salt thereof, as an active ingredient thereof.

3. A ketone derivative represented by the following formula (II):

[CHEMICAL 2]

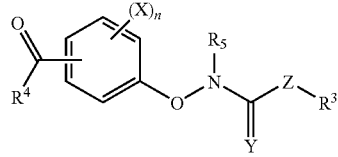

(II)

wherein, X represents a halogen atom, $C_{1-20}$ alkyl group, $C_{1-20}$ alkoxy group, $C_{1-20}$ haloalkyl group or $C_{1-20}$ haloalkoxy group, $R^3$ represents a hydrogen atom, $C_{1-20}$ alkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group or optionally substituted $C_{3-10}$ cycloalkyl group, $R^4$ represents a hydrogen atom, $C_{1-20}$ alkyl group, optionally substituted $C_{3-10}$ cycloalkyl group, $C_{2-20}$ alkenyl group, $C_{2-20}$ alkynyl group, $C_{1-20}$ haloalkyl group, $C_{2-20}$ haloalkenyl group, $C_{2-20}$ haloalkynyl group, cyano group, nitro group or optionally substituted amino group, $R^5$ represents a hydrogen atom, $C_{1-20}$ alkyl group, acyl group, formyl group, $C_{1-20}$ alkoxy-$C_{1-20}$ alkyl group, $C_{2-20}$ acyloxy-$C_{1-20}$ alkyl group, $C_{1-20}$ alkoxycarbonyl group, $C_{1-20}$ alkylsulfonyl group or optionally substituted phenylsulfonyl group, Y represents an oxygen atom or sulfur atom, Z represents a single bond, oxygen atom, sulfur atom or $NR^6$ (wherein, $R^6$ represents a hydrogen atom or $C_{1-30}$ alkyl group), and n represents an integer of 0 to 4, and X may be the same or different in the case n is 2 or more.

* * * * *